United States Patent
Kelly et al.

(10) Patent No.: US 11,013,734 B2
(45) Date of Patent: May 25, 2021

(54) TREATING PATIENTS HARBORING AN ISOCITRATE DEHYDROGENASE-1 (IDH-1) MUTATION

(71) Applicant: FORMA Therapeutics, Inc., Watertown, MA (US)

(72) Inventors: Patrick F. Kelly, Concord, MA (US); Alan Collis, Lexington, MA (US); Jeff Davis, Hingham, MA (US); Duncan Walker, Boulder, CO (US); Susan Ashwell, Carlisle, MA (US); Blythe Thomson, Cincinnati, OH (US); Wei Lu, Newton, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

(21) Appl. No.: 16/526,593

(22) Filed: Jul. 30, 2019

(65) Prior Publication Data

US 2019/0350922 A1 Nov. 21, 2019

Related U.S. Application Data

(63) Continuation-in-part of application No. 16/431,588, filed on Jun. 4, 2019, which is a continuation-in-part of application No. PCT/US2019/032742, filed on May 16, 2019, said application No. 16/431,588 is a continuation-in-part of application No. PCT/US2019/032747, filed on May 16, 2019, said application No. 16/431,588 is a continuation-in-part of application No. 16/414,505, filed on May 16, 2019, and a continuation-in-part of application No. 16/414,716, filed on May 16, 2019, now Pat. No. 10,532,047, application No. 16/526,593, filed on Jul. 30, 2019, which is a continuation-in-part of application No. PCT/US2019/032747, filed on May 16, 2019.

(60) Provisional application No. 62/692,591, filed on Jun. 29, 2018, provisional application No. 62/672,462, filed on May 16, 2018, provisional application No. 62/672,461, filed on May 16, 2018, provisional application No. 62/812,367, filed on Mar. 1, 2019, provisional application No. 62/798,677, filed on Jan. 30, 2019, provisional application No. 62/798,681, filed on Jan. 30, 2019, provisional application No. 62/798,684, filed on Jan. 30, 2019, provisional application No. 62/798,687, filed on Jan. 30, 2019, provisional application No. 62/798,690, filed on Jan. 30, 2019, provisional application No. 62/773,562, filed on Nov. 30, 2018, provisional application No. 62/692,598, filed on Jun. 29, 2018, provisional application No. 62/692,601, filed on Jun. 29, 2018, provisional application No. 62/692,604, filed on Jun. 29, 2018, provisional application No. 62/692,605, filed on Jun. 29, 2018, provisional application No. 62/680,566, filed on Jun. 4, 2018, provisional application No. 62/680,571, filed on Jun. 4, 2018, provisional application No. 62/680,560, filed on Jun. 4, 2018, provisional application No. 62/680,562, filed on Jun. 4, 2018, provisional application No. 62/712,160, filed on Jul. 30, 2018, provisional application No. 62/701,487, filed on Jul. 20, 2018.

(51) Int. Cl.
| | | |
|---|---|---|
| A61K 31/4709 | (2006.01) | |
| A61P 35/02 | (2006.01) | |
| C12Q 1/686 | (2018.01) | |
| C12Q 1/6886 | (2018.01) | |

(52) U.S. Cl.
CPC .......... *A61K 31/4709* (2013.01); *A61P 35/02* (2018.01); *C12Q 1/686* (2013.01); *C12Q 1/6886* (2013.01); *C12Q 2531/113* (2013.01); *C12Q 2561/113* (2013.01); *C12Q 2600/156* (2013.01)

(58) Field of Classification Search
CPC .................................................. A61K 31/4709
USPC ........................................................ 514/312
See application file for complete search history.

(56) References Cited

U.S. PATENT DOCUMENTS

| | | | |
|---|---|---|---|
| 5,262,564 A | 11/1993 | Kun et al. | |
| 5,984,882 A | 11/1999 | Rosenschein et al. | |
| 6,410,516 B1 | 6/2002 | Baltimore et al. | |
| 6,914,128 B1 | 7/2005 | Salfeld et al. | |
| 6,979,675 B2 | 12/2005 | Tidmarsh | |
| 7,217,286 B2 | 5/2007 | Falotico et al. | |
| 8,367,347 B2 | 2/2013 | Hartmann et al. | |
| 8,469,749 B2 | 6/2013 | Ladouceur et al. | |
| 8,685,660 B2 | 4/2014 | Vogelstein et al. | |
| 8,876,991 B2 | 11/2014 | Luebke | |
| 8,882,892 B2 | 11/2014 | Hoversten et al. | |
| 8,883,438 B2 | 11/2014 | Cantley et al. | |

(Continued)

FOREIGN PATENT DOCUMENTS

| | | |
|---|---|---|
| CN | 102558049 A | 7/2012 |
| CN | 103814020 A | 5/2014 |

(Continued)

OTHER PUBLICATIONS

U.S. Appl. No. 16/290,240, filed Mar. 1, 2019, Lin et al.

(Continued)

*Primary Examiner* — Taofiq A Solola
(74) *Attorney, Agent, or Firm* — Barnes & Thornburg LLP

(57) ABSTRACT

Methods of treating patients diagnosed with AML or MDS harboring mutant IDH-1 include detecting an IDH1 mutation and the therapeutic administration of an inhibitor of a mutant IDH-1 as a single agent, or in combination with azacitidine (AZA) or cytarabine.

24 Claims, 24 Drawing Sheets

(56) References Cited

U.S. PATENT DOCUMENTS

| | | | |
|---|---|---|---|
| 8,933,395 B2 | 1/2015 | Mueth et al. | |
| 9,073,941 B2 | 7/2015 | Wong et al. | |
| 9,335,332 B2 | 5/2016 | Kumaravel et al. | |
| 9,353,418 B2 | 5/2016 | Vogelstein et al. | |
| 9,624,175 B2 | 4/2017 | Lin et al. | |
| 9,624,216 B2 | 4/2017 | Lin et al. | |
| 9,771,349 B2 | 9/2017 | Lin et al. | |
| 9,815,817 B2 | 11/2017 | Lin et al. | |
| 9,834,539 B2 | 12/2017 | Lin et al. | |
| 10,005,734 B2 | 6/2018 | Lin et al. | |
| 10,253,015 B2 | 4/2019 | Lin et al. | |
| 10,266,495 B2 | 4/2019 | Lin et al. | |
| 10,280,150 B2 | 5/2019 | Lin et al. | |
| 10,414,752 B2 | 9/2019 | Lin et al. | |
| 10,532,047 B2 | 1/2020 | Luke | |
| 10,550,098 B2 | 2/2020 | Lin et al. | |
| 10,610,125 B2 | 4/2020 | Dang et al. | |
| 10,704,108 B2 | 7/2020 | Vogelstein et al. | |
| 10,837,064 B2 | 11/2020 | Vogelstein et al. | |
| 2003/0105124 A1 | 6/2003 | Sobolov-Jaynes | |
| 2004/0106645 A1 | 6/2004 | Blackburn et al. | |
| 2006/0281122 A1 | 12/2006 | Bryant et al. | |
| 2008/0300208 A1 | 12/2008 | Einat et al. | |
| 2012/0184548 A1 | 7/2012 | Dominique et al. | |
| 2012/0184562 A1 | 7/2012 | Luk | |
| 2014/0235620 A1 | 8/2014 | Caferro et al. | |
| 2016/0083349 A1 | 3/2016 | Lin et al. | |
| 2016/0083365 A1 | 3/2016 | Lin et al. | |
| 2016/0083366 A1* | 3/2016 | Lin | C07D 471/04 514/249 |
| 2016/0083367 A1 | 3/2016 | Lin et al. | |
| 2016/0311774 A1 | 10/2016 | Lin et al. | |
| 2016/0311818 A1 | 10/2016 | Lin et al. | |
| 2017/0081730 A1 | 3/2017 | Vogelstein et al. | |
| 2017/0157132 A1 | 6/2017 | Wu et al. | |
| 2017/0174658 A1 | 6/2017 | Lin et al. | |
| 2018/0086733 A1 | 3/2018 | Lin et al. | |
| 2018/0118732 A1 | 5/2018 | Lin et al. | |
| 2018/0134682 A1 | 5/2018 | Lin et al. | |
| 2018/0141910 A1 | 5/2018 | Lin et al. | |
| 2018/0312487 A1 | 11/2018 | Lin et al. | |
| 2018/0327361 A1 | 11/2018 | Lin et al. | |
| 2018/0327382 A1 | 11/2018 | Lin et al. | |
| 2019/0135781 A1 | 5/2019 | Lin et al. | |
| 2019/0263778 A1 | 8/2019 | Lin et al. | |
| 2019/0350919 A1 | 11/2019 | Kelly et al. | |
| 2019/0350920 A1 | 11/2019 | Luke et al. | |
| 2019/0350921 A1 | 11/2019 | Ashwell | |
| 2020/0085815 A1 | 3/2020 | Luke et al. | |
| 2020/0108060 A1 | 4/2020 | Kelly et al. | |
| 2020/0223822 A1 | 7/2020 | Lin et al. | |

FOREIGN PATENT DOCUMENTS

| | | |
|---|---|---|
| EP | 0481802 A1 | 4/1992 |
| RU | 2284325 C2 | 9/2006 |
| WO | WO-00/40749 A2 | 7/2000 |
| WO | WO-2006/054912 A1 | 5/2006 |
| WO | WO-2007/117778 A2 | 10/2007 |
| WO | WO-2008/010964 A1 | 1/2008 |
| WO | WO-2008/069242 A1 | 6/2008 |
| WO | WO-2010/028099 A1 | 3/2010 |
| WO | WO-2010/105243 A1 | 9/2010 |
| WO | WO-2011/020211 A1 | 4/2011 |
| WO | WO-2011/050210 A1 | 4/2011 |
| WO | WO-2011/072174 A1 | 6/2011 |
| WO | WO-2012/040332 A2 | 3/2012 |
| WO | WO-2012/054915 A2 | 4/2012 |
| WO | WO-2012/079532 A1 | 6/2012 |
| WO | WO-2012/129562 A2 | 9/2012 |
| WO | WO-2012/171337 A1 | 12/2012 |
| WO | WO-2012/171506 A1 | 12/2012 |
| WO | WO-2012/173682 A2 | 12/2012 |
| WO | WO-2013/046136 A1 | 4/2013 |
| WO | WO-2013/096820 A1 | 6/2013 |
| WO | WO-2013/102431 A1 | 7/2013 |
| WO | WO-2013/107291 A1 | 7/2013 |
| WO | WO-2013/107405 A1 | 7/2013 |
| WO | WO-2013/027997 A1 | 9/2013 |
| WO | WO-2014/141153 A1 | 9/2014 |
| WO | WO-2014/147586 A1 | 9/2014 |
| WO | WO-2014/184272 A2 | 11/2014 |
| WO | WO-2015/003146 A1 | 1/2015 |
| WO | WO-2015/121210 A1 | 8/2015 |
| WO | WO-2016/044781 A1 | 3/2016 |
| WO | WO-2016/044782 A1 | 3/2016 |
| WO | WO-2016/044787 A1 | 3/2016 |
| WO | WO-2016/044789 A1 | 3/2016 |
| WO | WO-2016/106331 A1 | 6/2016 |
| WO | WO-2016/108045 A2 | 7/2016 |
| WO | WO-2016/171755 A1 | 10/2016 |
| WO | WO-2016/171756 A1 | 10/2016 |
| WO | WO-2017/019429 A1 | 2/2017 |
| WO | WO-2017/146795 A1 | 8/2017 |
| WO | WO-2017/213910 A1 | 12/2017 |
| WO | WO-2017/223202 A1 | 12/2017 |
| WO | WO-2018/111707 A1 | 6/2018 |
| WO | WO-PCT/US19/32742 | 5/2019 |
| WO | WO-PCT/US19/32747 | 5/2019 |
| WO | WO-2019/222551 A1 | 11/2019 |
| WO | WO-2019/222553 A1 | 11/2019 |
| WO | WO-2020/232281 A1 | 11/2020 |

OTHER PUBLICATIONS

U.S. Appl. No. 16/414,505, filed May 16, 2019, Kelly et al.
U.S. Appl. No. 16/414,716, filed May 16, 2019, Luke et al.
U.S. Appl. No. 16/431,588, filed Jun. 4, 2019, Ashwell.
Abbas, S. et al., Acquired mutations in the genes encoding IDH1 and IDH2 both are recurrent aberrations in acute myeloid leukemia: prevalence and prognostic value, Blood, 116(12): 2122-2126 (2010).
Abbott RealTime IDH1 label, Reference No. 08N90-090, 31 pages (Jul. 2018); accessed on Jul. 29, 2019 from https://www.fda.gov/medical-devices/vitro-diagnostics/list-cleared-or-approved-companion-diagnostic-devices-vitro-and-imaging-tools.
Aghili, M. et al., Hydroxyglutaric aciduria and malignant brain tumor: a case report and literature review, J. Neurooncol., 91: 233-236 (2009).
Agios Pharmaceuticals, Press Release, Agios Announces Initiation of Phase 1/2 Frontline Combination Study of AG-221 or AG-120 with VIDAZA® (azacitidine for injection) in Newly Diagnosed Acute Myeloid Leukemia (AML) Patients Not Eligible for Intensive Chemotherapy, 4 pages (Cambridge, Mass, Mar. 30, 2016).
Agios Pharmaceuticals, Press Release, Agios Announces Phase 1 Data from Dose Expansion Cohorts of AG-120 in Patients with IDH1 Mutant Positive Glioma and Chondrosarcoma, 4 pages (Cambridge, Mass, Nov. 18, 2016).
Agios Pharmaceuticals, Press Release, Agios Pharmaceuticals to Present Clinical and Preclinical Data at the 2014 American Society of Hematology Annual Meeting, 7 pages (Cambridge, Mass., Nov. 6, 2014). URL: <http://investor.agios.com/news-releases/news-release-details/agios-pharmaceuticals-present-clinical-and-preclinical-data-2014> [Retrieved May 14, 2019].
Agios Pharmaceuticals, Press Release, Agios Presents Phase 1 Data from Dose-Escalation and Expansion Cohorts of AG-120 (Ivosidenib) in Patients with Previously Treated IDH1 Mutant Positive Cholangiocarcinoma, 4 pages (Chicago, Jun. 3, 2017).
Agios Pharmaceuticals, Press Release, Agios to Present New Data From Lead Programs at the 2015 Ash Annual Meeting, 6 pages (Cambridge, Mass., Nov. 5, 2014). URL: <http://investor.agios.com/news-releases/news-release-details/agios-present-new-data-lead-programs-2015-ash-annual-meeting> [Retrieved May 14, 2019].
Amary, M.F. et al., IDH1 and IDH2 mutations are frequent events in central chondrosarcoma and central and periosteal chondromas but not in other mesenchymal tumours, J Pathol, 224: 334-343 (2011).
Amary, M.F. et al., Ollier disease and Maffucci syndrome are caused by somatic mosaic mutations of IDH1 and IDH2, Nature Genetics, 43(12): 1262-1265 (2011).

(56) References Cited

OTHER PUBLICATIONS

Amidon, G.L. et al., A Theoretical Basis for a Biopharmaceutical Drug Classification: The Correlation of in Vitro Drug Product Dissolution and in Vivo Bioavailability, Pharmaceutical Research, 12(3): 413-420 (1995).

Androues, O.C. et al., Pharmacodynamics of mutant-IDH1 inhibitors in glioma patients probed by in vivo 3D MRS imaging of 2-hydroxyglutarate, Nature Communications, 9: 1474, 9 pages (2018).

Asteian, A. et al., Design, Synthesis, and Biological Evaluation of Indole Biphenylcarboxylic Acids as PPAR? Antagonists, ACS Med. Chem. Lett., 6: 998-1003 (2015).

Badr, M.Z.A. et al., Reaction of Quinoxaline Derivatives with Nucleophilic Reagents, , Bull Chem Soc Jpn, 56(1): 326-330 (1983).

Baer, M.R. et al., A Phase 1 Dose Escalation Study of the IDH1m Inhibitor, FT-2102, in Patients with Acute Myeloid Leukemia (AML) or Myelodysplastic Syndrome (MDS), Abstract for Congress of EHA, EHA-1757: 1 page (Jun. 2018).

Baer, M.R. et al., A Phase 1 Dose Escalation Study of the IDH1m Inhibitor, FT-2102, in Patients with Acute Myeloid Leukemia (AML) or Myelodysplastic Syndrome (MDS), Presented at the 2018 Congress of EHA, Poster PF236, Stockholm (Jun. 15, 2018).

Bai, H. et al., Integrated genomic characterization of IDH1-mutant glioma malignant progression, Nature Genetics, 48(1): 59-66 (2016).

Balss, J. et al., Analysis of the IDH1 codon 132 mutation in brain tumors, Acta Neuropathol, 116: 597-602 (2008).

Bertus, P. and Szymoniak, J., A direct synthesis of 1-aryl- and 1-alkenylcyclopropylamines from aryl and alkenyl Nitriles Journal of Organic Chemistry, 68(18): 7133-7136 (2003).

Birendra, K.C. and Dinardo, C.D., Evidence for clinical differentiation and differentiation syndrome in patients with acute myeloid leukemia and IDH1 mutations treated with the targeted mutant IDH1 inhibitor, AG-120, Clin Lymphoma Myeloma Leuk., 16(8): 460-465 (2016).

Bleeker, F.E. et al., Recent advances in the molecular understanding of glioblastoma, J. Neurooncol, 108: 11-27 (2012).

Boddu, P. and Borthakur, G., Therapeutic targeting of isocitrate dehydrogenase mutant AML, Expert Opinion on Investigational Drugs, 26(5): 525-529 (2017).

Borg, G. et al., One-pot asymmetric synthesis of tert-butanesulfinyl-protected amines from ketones by the in situ reduction of tert-butanesulfinyl ketimines, Tetrahedron Letters, 40: 6709-6712 (1999).

Borger, D.R. et al., Circulating Oncometabolite 2-Hydroxyglutarate is a Potential Surrogate Biomarker in Patients with Isocitrate Dehydrogenase-Mutant Intrahepatic Cholangiocarcinoma, Clin Cancer Res, 20(7): 1884-1890 (2014).

Borger, D.R., et al., Frequent mutation of isocitrate dehydrogenase (IDH)1 and IDH2 in cholangiocarcinoma identified through broad-based tumor genotyping, The Oncologist 17, 72-79 (2012).

Borodovsky, A. et al., 5-azacytidine reduces methylation, promotes differentiation and induces tumor regression in a patient-derived IDH1 mutant glioma xenograft, Oncotarget, 4(10): 1737-1747 (2013).

Brooks, E. et al., Identification and Characterization of Small-Molecule Inhibitors of the R132H/R132H Mutant Isocitrate Dehydrogenase 1 Homodimer and R132H/Wild-Type Heterodimer, Journal of Biomolecular Screening, 19(8): 1193-1200 (2014).

Bunse, L. et al., Suppression of antitumor T cell immunity by the oncometabolite (R)-2-hydroxyglutarate, Nature Medicine, 25 pages (2018).

Burris, H. et al., Abstract PL04-05: The first reported results of AG-120, a first-in-class, potent inhibitor of the IDH1 mutant protein, in a Phase I study of patients with advanced IDH1-mutant solid tumors, including gliomas, Mol. Cancer Ther., 14(12 Supplement 2): 5 pages (Dec. 2015).

Cairns, R.A. and Mak, T.W., Oncogenic Isocitrate Dehydrogenase Mutations: Mechanisms, Models, and Clinical Opportunities, Cancer Discover, 730-741 (2013).

Cancer Genome Atlas Research Network, Comprehensive, Integrative Genomic Analysis of Diffuse Lower-Grade Gliomas, N Engl J Med, 372: 2481-2498 (2015).

Center for Drug Evaluation and Research, Application No. 209606Orig11000, Multi-Discipline Review, Reference ID: 4131433, 190 pages (Submission date Dec. 30, 2016).

Center for Drug Evaluation and Research, Application No. 211192Orig1s000, Multi-Discipline Review, Reference ID: 4294809, 235 pages (Submission date Dec. 21, 2017).

Chaturvedi, A. et al., Mutant IDH1 promotes leukemogenesis in vivo and can be specifically targeted in human AML, Blood, 122(16): 2877-2887 (2013).

Chaturvedi, A. et al., Pan-mutant-IDH1 inhibitor BAY1436032 is highly effective against human IDH1 mutant acute myeloid leukemia in vivo, Leukemia, 31: 2020-2028 (2017).

Chiou, W.L., and Barve, A., Linear Correlation of the Fraction of Oral Dose Absorbed of 64 Drugs Between Humans and Rats, Pharmaceutical Research, 15(11): 1792-1795 (1998).

Cho, Y.S. et al., Discovery and Evaluation of Clinical Candidate IDH305, a Brain Penetrant Mutant IDH1 Inhibitor, ACS Med Chem Lett., 8(10): 1116-1121 (2017). Supporting Information, 31 pages.

Chowdhury, R. et al., The oncometabolite 2-hydroxyglutarate inhibits histone lysine demethylases, EMBO Reports, 12(5): 463-469 (2011).

Claus, E.B. et al., Survival and low grade glioma: the emergence of genetic Information, Neurosurg Focus, 38(1): E6, 19 pages (2015).

ClinicalTrials.gov Identifier: NCT02073994, Study of Orally Administered AG-120 in Subjects With Advanced Solid Tumors, Including Glioma, With an IDH1 Mutation, First Posted Feb. 28, 2014; Last Update Posted Jun. 4, 2019. https://clinicaltrials.gov/ct2/show/NCT02073994?term=NCT02073994&rank=1.

ClinicalTrials.gov Identifier: NCT02481154, Study of Orally Administered AG-881 in Patients With Advanced Solid Tumors, Including Gliomas, With an IDH1 and/or IDH2 Mutation, First Posted Jun. 25, 2015; Last Update Posted Jun. 6, 2019. https://clinicaltrials.gov/ct2/show/NCT02481154?term=NCT02481154&rank=1.

ClinicalTrials.gov Identifier: NCT02719574, "Open-label Study of FT-2102 With or Without Azacitidine or Cytarabine in Patients With AML or MDS With an IDH1 Mutation," (v1 dated Mar. 21, 2016, published Mar. 24, 2016, and first posted Mar. 25, 2016 at https://clinicaltrials.gov/ct2/history/NCT02719574?V_1=View#StudyPageTop).

ClinicalTrials.gov Identifier: NCT02719574, "Open-label Study of FT-2102 With or Without Azacitidine or Cytarabine in Patients With AML or MDS With an IDH1 Mutation," (v10 dated Nov. 6, 2017, published Nov. 7, 2017, and update posted Nov. 8, 2017 at https://clinicaltrials.gov/ct2/history/NCT02719574?V_10=View#StudyPageTop).

ClinicalTrials.gov Identifier: NCT02719574, "Open-label Study of FT-2102 With or Without Azacitidine or Cytarabine in Patients With AML or MDS With an IDH1 Mutation," (v11 dated Dec. 6, 2017, published Dec. 7, 2017, and update posted Dec. 8, 2017 at https://clinicaltrials.gov/ct2/history/NCT02719574?V_11=View#StudyPageTop).

ClinicalTrials.gov Identifier: NCT02719574, "Open-label Study of FT-2102 With or Without Azacitidine or Cytarabine in Patients With AML or MDS With an IDH1 Mutation," (v12 dated May 17, 2018, Published May 18, 2018, and update posted May 21, 2018 at https://clinicaltrials.gov/ct2/history/NCT02719574?V_12=View#StudyPageTop).

ClinicalTrials.gov Identifier: NCT02719574, "Open-label Study of FT-2102 With or Without Azacitidine or Cytarabine in Patients With AML or MDS With an IDH1 Mutation," (v13 dated Nov. 27, 2018, published Nov. 28, 2018, and update posted Nov. 29, 2018 at https://clinicaltrials.gov/ct2/history/NCT02719574?V_13=View#StudyPageTop).

ClinicalTrials.gov Identifier: NCT02719574, "Open-label Study of FT-2102 With or Without Azacitidine or Cytarabine in Patients With AML or MDS With an IDH1 Mutation," (v2 dated Apr. 21, 2016 published Apr. 21, 2016, and update posted Apr. 22, 2016 at https://clinicaltrials.gov/ct2/history/NCT02719574?V_2=View#StudyPageTop).

(56) References Cited

OTHER PUBLICATIONS

ClinicalTrials.gov Identifier: NCT02719574, "Open-label Study of FT-2102 With or Without Azacitidine or Cytarabine in Patients With AML or MDS With an IDH1 Mutation," (v3 dated Jun. 8, 2016, published Jun. 8, 2016, and update posted Jun. 9, 2016 at https://clinicaltrials.gov/ct2/history/NCT02719574?V_3=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v4 dated Jul. 1, 2016, published Jul. 1, 2016, and update posted Jul. 4, 2016 at https://clinicaltrials.gov/ct2/history/NCT02719574?V_4=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v5 dated Jul. 12, 2016, published Jul. 12, 2016, and update posted Jul. 13, 2016 at https://clinicaltrials.gov/ct2/history/NCT02719574?V_5=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v6 dated Aug. 17, 2016, published Aug. 18, 2016, and update posted Aug. 19, 2016 at https://clinicaltrials.gov/ct2/history/NCT02719574?V_6=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v7 dated Dec. 8, 2016, published Dec. 8, 2016, and update posted Dec. 9, 2016 at https://clinicaltrials.gov/ct2/history/NCT02719574?V_7=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v8 dated Feb. 15, 2017, published Feb. 16, 2017, and update posted Feb. 16, 2017 at https://clinicaltrials.gov/ct2/history/NCT02719574?V_8=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v9 dated May 5, 2017, published May 5, 2017, and update posted May 8, 2017 at https://clinicaltrials.gov/ct2/history/NCT02719574?V_9=View#StudyPageTop).
ClinicalTrials.gov Identifier: NCT02719574, "Open-label Study of FT-2102 With or Without Azacitidine or Cytarabine in Patients With AML or MDS With an IDH1 Mutation," Study Details, (First Posted May 18, 2018, Last Update Posted Nov. 29, 2018).
ClinicalTrials.gov Identifier: NCT03343197, Study of AG-120 and AG-881 in Subjects With Low Grade Glioma, First Posted Nov. 17, 2017; Last Update Posted Jul. 23, 2018. https://clinicaltrials.gov/ct2/show/NCT03343197?term=NCT03343197&rank=1.
ClinicalTrials.gov Identifier: NCT03684811, "A Study of FT-2102 in Participants with Advanced Solid Tumors and Gliomas With an IDH1 Mutation," (v1 dated Sep. 24, 2018; update published on Sep. 25, 2018, and posted on Sep. 26, 2018 https://clinicaltrials.gov/ct2/history/NCT03684811?V_1=View#StudyPageTop.
ClinicalTrials.gov Identifier: NCT03684811, "A Study of FT-2102 in Participants with Advanced Solid Tumors and Gliomas With an IDH1 Mutation," (v2 dated Nov. 12, 2018; update published on Nov. 13, 2018, and posted on Nov. 14, 2018 https://clinicaltrials.gov/ct2/history/NCT03684811?V_2=View#StudyPageTop.
ClinicalTrials.gov Identifier: NCT03684811, "A Study of FT-2102 in Participants with Advanced Solid Tumors and Gliomas With an IDH1 Mutation," (v3 dated Feb. 12, 2019; update published on Feb. 12, 2019 and posted on Feb. 15, 2019 https://clinicaltrials.gov/ct2/history/NCT03684811?V_3=View#StudyPageTop.
ClinicalTrials.gov Identifier: NCT03684811, "A Study of FT-2102 in Participants with Advanced Solid Tumors and Gliomas With an IDH1 Mutation," (v4 dated Feb. 15, 2019; update published on Feb. 18, 2019, and posted on Feb. 19, 2019 https://clinicaltrials.gov/ct2/history/NCT03684811?V_4=View#StudyPageTop.
ClinicalTrials.gov Identifier: NCT03684811, "A Study of FT-2102 in Participants with Advanced Solid Tumors and Gliomas With an IDH1 Mutation," (v5 dated Mar. 13, 2019; update published on Mar. 13, 2019, and posted on Mar. 14, 2019 https://clinicaltrials.gov/ct2/history/NCT03684811?V_5=View#StudyPageTop.
ClinicalTrials.gov Identifier: NCT03684811, "A Study of FT-2102 in Participants with Advanced Solid Tumors and Gliomas With an IDH1 Mutation," Study Details (First Posted Sep. 26, 2018, Last Update Posted May 1, 2019).
Cohen, A. et al., IDH1 and IDH2 Mutations in Gliomas, Curr Neurol Neurosci Rep., 13(5): 345, 13 pages (2013).
Cortes, J.E. et al., FT-2102, an IDH1m Inhibitor, Combined with Azacitidine in Patients with Acute Myeloid Leukemia (AML) or Myelodysplastic Syndrome (MDS): Results from A Phase 1 Study, Congress of EHA 2019 Abstract Submission, 4. Acute myeloid leukemia—Clinical, EHA-3328, 2 pages (submitted Mar. 1, 2019).
Cortes, J.E. et al., FT-2102, an IDH1m Inhibitor, Combined with Azacitidine in Patients with Acute Myeloid Leukemia (AML) or Myelodysplastic Syndrome (MDS): Results from a Phase 1 Study, Poster EHA-3328, Presented at the 24th Annual Congress of the European Hematology Association, Amsterdam, Netherlands, Jun. 14, 2019.
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, ASH abstract available on online meeting program, 9 pages (submitted Jul. 31, 2018, published Nov. 1, 2018).
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, Poster 1452, Presented at the 60th Annual Meeting of the American Society of Hematology, San Diego, CA (Dec. 1, 2018).
Cui, Z. et al., Structure and properties of N-heterocycle-containing benzotriazoles as UV absorbers, Journal of Molecular Structure, 1054: 94-99 (2013).
Cytosar-U, Sterile Cytarabine, USP; Drug Description, Pharmacia & Upjohn Company, Revised Sep. 1997, 6 page (Approved Oct. 15, 1998).
Dai, D. et al., Clinical pharmacokinetics/pharmacodynamics (PK/PD) of ivosidenib in patients with IDH1-mutant advanced hematologic malignancies from a phase 1 study, 2018 ASCO Annual Meeting, J Clin Oncol., 36 (Abstract 2581), 1 page (Jun. 4, 2018). URL: https://meetinglibrary.asco.org/record/158639/abstract [Retrieved Jun. 7, 2018].
Damato, S. et al., IDH1 mutations are not found in cartilaginous tumours other than central and periosteal chondrosarcomas and enchondromas, Histopathology, 60: 357-376 (2011).
Dang, L. et al., Cancer-associated IDH1 mutations produce 2-hydroxyglutarate, Nature, 462: 739-744 (2009).
Dang, L. et al., IDH mutations in cancer and progress toward development of targeted therapeutics, Annals of Oncology, 27: 599-608 (2016).
Dang, L. et al., IDH mutations in glioma and acute myeloid leukemia, Trends Mol. Med., 16(9): 387-397 (2010).
Database Caplus (Online) Chemical Abstracts Service, Columbus, Ohio, US; retrieved from STN Database accession No. 1987: 407040 abstract, Prostakov, N.S. et al., Synthesis of substituted 2-pyridones and 4-aza-3-fluorenones, Khimiya Geterotsiklicheskikh Soedinenii, 7: 939-942 (1986).
Database Registry (Online) Chemical Abstracts Service, Columbus, Ohio, US; Database accession No. 1434379-53-9 (Jun. 5, 2013).
Database Registry (Online) Chemical Abstracts Service, Columbus, Ohio, US; Database accession No. 1497653-96-9 (Dec. 18, 2013).
Database Registry (Online) Chemical Abstracts Service, Columbus, Ohio, US; Database accession No. 1567357-55-4 (Mar. 12, 2014).
Database Registry (Online) Chemical Abstracts Service, Columbus, Ohio, US; Database accession No. 1567456-94-3 (Mar. 12, 2014).
De Botton, S. et al., Clinical Safety and Activity of AG-120, a First-in-Class, Potent Inhibitor of the IDH1-Mutant Protein, in a

(56) References Cited

OTHER PUBLICATIONS

Phase 1 Study of Patients with Advanced IDH-Mutant Hematologic Malignancies. European Hematology Association Learning Center, P563 (2015).

De Botton, S. et al., FT-2102, An IDH1m Inhibitor, Induces Mutation Clearance in Patients With Acute Myeloid Leukemia (AML) or Myelodysplastic Syndrome (MDS) Treated in Phase 1 Dose Escalation and Expansion Study, Abstract Submission, 4. Acute myeloid leukemia—Clinical, EHA-3251, 2 pages (submitted Mar. 1, 2019).

De Botton, S. et al., FT-2102, an IDH1m Inhibitor, Induces Mutation Clearance in Patients with Acute Myeloid Leukemia (AML) or Myelodysplastic Syndrome (MDS) Treated in Phase 1 Dose Escalation and Expansion Study, Poster EHA-3251, Presented at the 24th Annual Congress of the European Hematology Association, Amsterdam, Netherlands, Jun. 15, 2019.

Deng, G. et al., Selective Inhibition of Mutant Isocitrate Dehydrogenase 1 (IDH1) via Disruption of a Metal Binding Network by an Allosteric Small Molecule, The Journal of Biological Chemistry, 290: 762-774 (2014).

Derissen, E.J.B. et al., ConciseDrug Review:Azacitidine andDecitabine, The Oncologist; 18: 619-624 (2013).

Diao, L. and Meibohm, B., Pharmacometric Applications and Challenges in the Development of Therapeutic Antibodies in Immuno-Oncology, Current Pharmacology Reports, 4: 285-291 (2018).

Dinardo, C., Highlights in Acute Myeloid Leukemia From the 2017 American Society of Hematology Annual Meeting and Exposition, Clinical Advance in Hematology & Oncology, 16(3): Suppl 8 (Mar. 2018), A Review of Selected Presentations From the 2017 American Society of Hematology Annual Meeting and Exposition, Atlanta, Georgia, 24 pages (Mar. 8, 2018).

Dinardo, C.D. and Cortes, J.E., Mutations in AML: prognostic and therapeutic implications, Hematology, 348-355 (2016).

Dinardo, C.D. et al., Characteristics, clinical outcome, and prognostic significance of IDH mutations in AML, Am J Hematol., 90(8): 732-736 (2015).

Dinardo, C.D. et al., Durable Remissions with Ivosidenib in IDH1-Mutated Relapsed or Refractory AML, N Engl J Med, 378: 2386-2398 (2018).

Dinardo, C.D. et al., Ivosidenib (AG-120) in Mutant IDH1 AML and Advanced Hematologic Malignancies: Results of a Phase 1 Dose Escalation and Expansion Study. Presented at: ASH Annual Meeting and Exposition, Atlanta, Georgia. Abstract 725, 3 pages (Dec. 13, 2017).

Dinardo, C.D. et al., Ivosidenib (AG-120) Induced Durable Remissions and Transfusion Independence in Patients with IDH1-Mutant Relapsed or Refractory Myelodysplastic Syndrome: Results from a Phase 1 Dose Escalation and Expansion Study, 2018 ASH Annual Meeting, Blood, 132: Abstract 1812 (2018).

Dinardo, C.D. et al., Ivosidenib (AG-120) Induced Durable Remissions and Transfusion Independence in Patients with IDH1-Mutant Relapsed or Refractory Myelodysplastic Syndrome: Results from a Phase 1 Dose Escalation and Expansion Study, 2018 ASH Annual Meeting, Poster, 132: Abstract 1812 (2018).

Dinardo, C.D. et al., Mutant IDH (mIDH) inhibitors, ivosidenib or enasidenib, with azacitidine (AZA) in patients with acute myeloid leukemia (AML), 2018 ASCO Annual Meeting, J Clin Oncol., 36 (Abstract 7042), 2 pages (Jun. 4, 2018). URL: https://meetinglibrary.asco.org/record/162432/abstract [Retrieved Jun. 7, 2018].

Dinardo, C.D. et al., Mutant IDH (MIDH) Inhibitors, Ivosidenib or Enasidenib, With Azacitidine (AZA) in Patients With Acute Myeloid Leukemia (AML), European Hematology Association, Abstract S1562, 2(S1): 719 (2018).

Dinardo, C.D. et al., Mutant Isocitrate Dehydrogenase (mIDH) Inhibitors, Enasidenib or Ivosidenib, in Combination with Azacitidine (AZA): Preliminary Results of a Phase 1b/2 Study in Patients with Newly Diagnosed Acute Myeloid Leukemia (AML), ASH Annual Meeting, Blood, 130: Abstract 639 (2017).

Dinardo, C.D. et al., Mutant Isocitrate Dehydrogenase (mIDH) Inhibitors, Enasidenib or Ivosidenib, in Combination with Azacitidine (AZA): Preliminary Results of a Phase 1b/2 Study in Patients with Newly Diagnosed Acute Myeloid Leukemia (AML), Presentation, ASH Annual Meeting, Abstract 639: 14 pages (2017).

Dinardo, C.D. et al., Serum 2-hydroxyglutarate levels predict isocitrate dehydrogenase mutations and clinical outcome in acute myeloid leukemia, Blood, 121(24): 4917-1924 (2013).

Dohner, H., Diagnosis and management of AML in adults: 2017 ELN recommendations from an international expert panel, Blood, 129: 424-447 (2017).

Eckmann, K.R. et al., Chemotherapy Outcomes for the Treatment of Unresectable Intrahepatic and Hilar Cholangiocarcinoma: A Retrospective Analysis, Gastrointest Cancer Res 4: 155-160 (2011).

El-Khoueiry, A.B. et al., Nivolumab in patients with advanced hepatocellular carcinoma (CheckMate 040): results of phase 1/2 dose escalation and expansion, USC Norris Comprehensive Cancer Center, 36 pages (2017).

Emadi, A. et al., Presence of isocitrate dehydrogenase mutations may predict clinical response to hypomethylating agents in patients with acute myeloid leukemia, Am. J. Hematol., 90: E77-E79, (2015).

Estekizadeh, A. et al., Increased cytomegalovirus replication by 5-Azacytidine and viral-induced cytoplasmic expression of DNMT-1 in medulloblastoma and endothelial cells, International Journal of Oncology, 52: 1317-1327 (2018).

Estey E., Acute myeloid leukemia and myelodysplastic syndromes in older patients, JCO, 25: 1908-1915 (2007).

Faderl, S. et al., Clofarabine plus cytarabine compared with cytarabine alone in older patients with relapsed or refractory acute myelogenous leukemia: results from the Classic I trial, J Clin Oncol., 30: 2492-2499 (2012).

Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Blood, 124: 3737, 6 pages (2014). URL: http://www.bloodjournal.org/content/124/21/3737?sso-checked=true [Retrieved May 13, 2019].

Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Poster 3737, Presented at the 56th American Society of Hematology Annual Meeting and Exposition, San Francisco, CA, 1 page (Dec. 8, 2014).

Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, American Society of Hematology, 57th Annual Meeting & Exposition, Orlando, FL, Abstract 1310, 2 pages (Dec. 508, 2015). URL: https://ash.confex.com/ash/2015/webprogramscheduler/Paper82908.html [Retrieved Jun. 7, 2018].

Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, Blood, 126(23): 1310-1310 (2015).

Fan, B. et al., Longitudinal pharmacokinetic/pharmacodynamic profile of AG-120, a potent inhibitor of the IDH1 mutant protein, in a phase 1 study of IDH1-mutant advanced hematologic malignancies, Poster 1310, Presented at the 57th American Society of Hematology Annual Meeting and Exposition, Orlando, FL, 1 page (Dec. 5, 2015).

Fan, B. et al., Pharmacokinetic/pharmacodynamic (PK/PD) profile of AG-120 in patients with IDH1-mutant cholangiocarcinoma from a phase 1 study of advanced solid tumors, Poster 4082, Presented at the American Society of Clinical Oncology (ASCO) Annual Meeting, Chicago, IL, USA, 1 page (Jun. 3, 2017).

Fan, B. et al., Pharmacokinetic/Pharmacodynamic (PK/PD) Profile of AG-120 in Patients with IDH1-Mutant Cholangiocarcinoma from a Phase 1 Study of Advanced Solid Tumorsm, Journal of Clinical Oncology, 35(15_suppl): 4082-4082 (May 20, 2017).

Fan, B. et al., Pharmacokinetic/pharmacodynamic evaluation of AG-120, a potent inhibitor of the IDH1 mutant protein, in a phase 1 study of IDH1-mutant advanced hematologic malignancies, Poster P572, Presented at the 20th Congress of the European Hematology Association, Vienna, Austria, 1 page (Jun. 13, 2015).

(56) References Cited

OTHER PUBLICATIONS

Fan, B. et al., Pharmacokinetics/pharmacodynamics (PK/PD) of ivosidenib in patients with IDH1-mutant advanced solid tumors from a phase 1 study, 2018 ASCO Annual Meeting, J Clin Oncol., 36 (Abstract 2577), 1 page (Jun. 4, 2018). URL: https://meetinglibrary.asco.org/record/158587/abstract [Retrieved Jun. 7, 2018].
Fatima, S., Molecular docking and 3D-QSAR studies on inhibitors of DNA damage signaling enzyme human PARP-1, J Receptors and Signal Transduction, 32(4) 214-224 (2012).
Fernandez, H.F. et al., Anthracycline dose intensification in acute myeloid leukemia, NEJM, 361: 1249-1259 (2009).
Figueroa, M.E. et al., Leukemic IDH1 and IDH2 mutations result in a hypermethylation phenotype, disrupt TET2 function, and impair hematopoietic differentiation, Cancer Cell, 18:553-567 (2010).
Flavahan, W.A. et al., Insulator dysfunction and oncogene activation in IDH mutant gliomas, Nature, 1-16 (2015).
Forma Therapeutics, Best-in-Class mIDH1 Inhibitor FT-2102, Presentation, 24 slides (Jan. 8-11, 2018).
Forma Therapeutics, Discovery and Optimization of a Novel Series of Inhibitors of mt-IDH1, 7th Annual Advances in Chemical Sciences Symposium, Presentation, 21 slides (May 4, 2018).
Forma Therapeutics, Forma Therapeutics and the University of Oxford Announce Multi-Year Collaboration to Advance the Development of Deubiquitinating Enzyme (DUB) Inhibitors for the Treatment of Neurodegenerative Diseases, Press Release, 2 pages (May 9, 2018).
Forma Therapeutics, Forma Therapeutics Announces Presentation at the 2018 American Society of Clinical Oncology (ASCO) Annual Meeting, FT-2102 IDH1m Inhibitor Clinical Data Selected for Oral Presentation, Abstract 7009: 1 page (May 10, 2018).
Frankel, S.R. et al., The "retinoic acid syndrome" in acute promyelocytic leukemia, Ann Intern Med., 117(4): 292-296 (1992).
Gaal, J. et al., Isocitrate Dehydrogenase Mutations Are Rare in Pheochromocytomas and Paragangliomas, J. Clin. Endocrinol. Metab., 95(3): 1274-1278 (2010).
Ghazanchyan, T. et al., Developing a Genomics Model to Predict Failure of Isocitrate Dehydrogenase (IDH) Inhibitors for Treatment of Patients with IDH1- or IDH2-Mutated Acute Myeloid Leukemia, 2018 ASH Annual Meeting, Blood, 132: Abstract 2815 (2018).
Ghiam, A.F. et al., IDH mutation status in prostate cancer, Oncogene, 31: 3826 (2012).
Goyal, L. et al., Prognosis and Clinicopathologic Features of Patients With Advanced Stage Isocitrate Dehydrogenase (IDH)Mutant and IDHWild-Type Intrahepatic Cholangiocarcinoma, The Oncologist, 20: 1019-1027 (2015).
Gross, S. et al., Cancer-associated metabolite 2-hydroxyglutarate accumulates in acute myelogenous leukemia with isocitrate dehydrogenase 1 and 2 mutations, J. Exp. Med., 207(2): 339-344 (2010).
Hayden, J.T. et al., Frequent IDH1 mutations in supratentorial primitive neuroectodermal tumors (sPNET) of adults but not children, Cell Cycle, 8(11): 1806-1807 (2009).
He, Y. et al., Asperspiropene A, a novel fungal metabolite as an inhibitor of cancer-associated mutant isocitrate dehydrogenase 1, Org. Chem. Front., 1-8 (2017).
Hindson, B. J. et al., High-Throughput Droplet Digital PCR System for Absolute Quantitation of DNA Copy Number, Anal. Chem., 83(22): 8604-8610 (2011).
Hondeghem, L.M. et al., Blinded Test in Isolated Female Rabbit Heart Reliably Identifies Action Potential Duration Prolongation and Proarrhythmic Drugs: Importance of Triangulation, Reverse Use Dependence, and Instability, Journal of Cardiovascular Pharmacology, 41: 14-24 (2003).
Hondeghem, L.M. et al., Instability and Triangulation of the Action Potential Predict Serious Proarrhythmia, but Action Potential Duration Prolongation is Antiarrhythmic, Circulation, 103: 2004-2013 (2001).
ICH Harmonised Tripartite Guideline, Good Manufacturing Practice Guide for Active Pharmaceutical Ingredients Q7, Current Step 4 version, 49 pages (Nov. 10, 2000).

International Search Report for PCT/US2015/051044, 4 pages (dated Nov. 23, 2015).
International Search Report for PCT/US2015/051046, 3 pages (dated Oct. 30, 2015).
International Search Report for PCT/US2015/051053, 4 pages (dated Oct. 28, 2015).
International Search Report for PCT/US2015/051055, 3 pages (dated Nov. 13, 2015).
International Search Report for PCT/US2015/051056, 4 pages (dated Nov. 20, 2015).
International Search Report for PCT/US2015/051059, 3 pages (dated Oct. 30, 2015).
Ishii, Y. et al., Abstract A071: AG-120 (ivosidenib), a first-in-class mutant IDH1 inhibitor, promotes morphologic changes and upregulates liver-specific genes in IDH1 mutant cholangiocarcinoma, Cellular Responses to Therapy, AACR-NCI-EORTC International Conference on Molecular Targets and Cancer Therapeutics, Oct. 26-30, 2017, Philadelphia, PA, 3 pages (Published Jan. 2018).
Janin, M. et al., Serum 2-Hydroxyglutarate Production in IDH1- and IDH2-Mutated De Novo Acute Myeloid Leukemia: A Study by the Acute Leukemia French Association Group, Journal of Clinical Oncology, 32(4): 297-305 (2014).
Jiang, K. et al., Primary Liver Cancers, Part 2: Progression Pathways and Carcinogenesis, Cancer Control, 25(1): 1-9 (2018).
Jones, S.; et al., Discovery and Optimization of Allosteric Inhibitors of Mutant Isocitrate Dehydrogenase 1 (R132H IDH1) Displaying Activity in Human Acute Myeloid Leukemia Cells, J. Med. Chem., 59(24): 11120-11137 (2016).
Kang, M.R. et al., Mutational analysis of IDH1 codon 132 in glioblastomas and other common cancers, Int. J. Cancer, 125: 353-355 (2009).
Kats, L.M., et al., Proto-oncogenic role of mutant IDH2 in leukemia initiation and maintenance, Cell Stem Cell, 14:329-341 (2014).
Koivunen, P. et al., Transformation by the R Enantiomer of 2-Hydroxyglutarate Linked to EgIN Activation, Nature, 483(7390): 484-488 (2013).
Kombarov, R.V. et al., CA Accession No. 138:368869, abstract only of Chem of Het Compounds, 38(9): 1154-1155 (2002).
Kopinja, J. et al., A Brain Penetrant Mutant IDH1 Inhibitor Provides In Vivo Survival Benefit, Scientific Reports, 7: 13853, 14 pages (2017).
Kurz, S.C. and Wen, P.Y., Quo Vadis-Do Immunotherapies Have a Role in Glioblastoma?, Curr Treat Options Neurol, 20: 14, 1-23 (2018).
Labussiere, M. et al., IDH1 Gene Mutations: A New Paradigm in Glioma Prognosis and Therapy?, The Oncologist, 15: 196-199 (2010).
Law, J. M.; et al., Discovery of 8-Membered Ring Sulfonamides as Inhibitors of Oncogenic Mutant Isocitrate Dehydrogenase 1. ACS Medicinal Chemistry Letters, 7(10): 944-949 (2016).
Le, K. et al., Population Pharmacokinetics of Ivosidenib (AG-120) in Patients with IDH1-Mutant Advanced Hematologic Malignancies, 2018 ASH Annual Meeting, Blood, 132: Abstract 1394 (2018).
Le, K. et al., Population Pharmacokinetics of Ivosidenib (AG-120) in Patients with IDH1-Mutant Advanced Hematologic Malignancies, Poster, 2018 ASH Annual Meeting, 132: Abstract 1394 (2018).
Lee, J.H. et al., IDH1 R132C mutation is detected in clear cell hepatocellular carcinoma by pyrosequencing, World Journal of Surgical Oncology, 15: 82, 8 pages. (2017).
Levell, J. R. et al., Optimization of 3-pyrimidin-4-yl-oxazolidin-2-ones as allosteric and mutant specific inhibitors of IDH1, ACS Med. Chem. Lett., 8: 151-156 (2017).
Lin, J. et al., Discovery and Optimization of Quinoline Derivatives as Potent, Selective, and Orally Bioavailable Mutant Isocitrate Dehydrogenase 1 Inhibitors. J. Med. Chem. (2019).
Liu, G. et al., Catalytic Asymmetric Synthesis of tert-Butanesulfinamide. Application to the Asymmetric Synthesis of Amines, J. Am. Chem. Soc., 119: 9913-9914 (1997).
Liu, G. et al., Synthesis of enantiomerically pure N-tert-butanesulfinyl imines (tertbutanesulfinimines) by the direct condensation of tert-butanesulfinamide with aldehydes and ketones. J. Org. Chem., 64(6): 1278-1284 (1999).

(56) References Cited

OTHER PUBLICATIONS

Liu, Z. et al., Inhibition of cancerassociated mutant isocitrate dehydrogenases: synthesis, structureactivity relationship, and selective antitumor activity. J. Med. Chem., 57: 8307-8318 (2014).

Lopez, G.Y. et al., IDH1 mutation identified in human melanoma, Biochem Biophys Res Commun., 398(3): 585-587 (2010).

Losman, J-A. et al., (R)-2-Hydroxyglutarate is Sufficient to Promote Leukemogenesis and its Effects are Reversible, Science, 339(6127): 9 pages (2013).

Lowery, M.A et al., A phase 3, multicenter, randomized, double-blind study of AG-120 vs placebo in patients with an advanced cholangiocarcinoma with an IDH1 mutation, ASCO Annual Meeting 2017, J Clin Oncol, 35: suppl; Abstract TPS4142 (2017).

Lowery, M.A. et al., Phase I study of AG-120, an IDH1 mutant enzyme inhibitor: Results from the cholangiocarcinoma dose escalation and expansion cohorts, Abstract 4015, Journal of Clinical Oncology, 35 (15 Suppl): 4015-4015 (May 20, 2017). URL: http://ascopubs.org/doi/abs/10.1200/JC0.2017.35.15_suppl.4015 [Retrieved Mar. 21, 2018].

Lu, C. et al., IDH mutation impairs histone demethylation and results in a block to cell differentiation, Nature, 483(7390): 474-478 (2012).

Lu, C. et al., Induction of sarcomas by mutant IDH2, Genes & Development, 27: 1986-1998 (2013).

Ma, R. and Yun, C. H., Crystal structures of pan-IDH inhibitor AH-881 in complex with mutant human IDH1 and IDH2, Biochem Biophys Res Commun, 503(4): 2912-2917 (2018).

Mahmood, I., Prediction of Clearance, volume of Distribution and Half-life by Allometric Scaling and by use of Plasma Concentrations Predicted from Pharmacokinetic Constants: a Comparative Study, J. Pharm. Pharmacol., 51: 905-910 (1999).

Mantica, M. et al., Retrospective study of nivolumab for patients with recurrent high grade gliomas, Journal of Neuro-Oncology, 139: 625-631 (2018).

Mardis, E.R. et al., Recurring Mutations Found by Sequencing an Acute Myeloid Leukemia Genome, N Engl J Med, 361(11): 1058-1066 (2009).

McBrayer, S.K. et al., Transaminase Inhibition by 2-Hydroxyglutarate Impairs Glutamate Biosynthesis and Redox Homeostasis in Glioma, Cell, 175: 101-116 (2018).

Medeiros, B.C. et al., Isocitrate dehydrogenase mutations in myeloid malignancies, Leukemia, 31: 272-281 (2017).

Meijer, D. et al., Genetic Characterization of Mesenchymal, Clear Cell, and Dedifferentiated Chondrosarcoma, Genes, Chromosomes & Cancer, 51:899-909 (2012).

Mellinghoff, I. et al., 2017 SNO Annual Meeting: Presentation ACTR-46.

Mellinghoff, I. et al., AG-120, A First-in-Class Mutant IDH1 Inhibitor in Patients with Recurrent or Progressive IDH1 Mutant Glioma: Updated Results from the Phase 1 Non-Enhancing Glioma Population, Presentation ACTR-46, Society for Neuro-Oncology Annual Scientific Meeting, Nov. 16-19, 2017, San Francisco, CA, USA (2017).

Mellinghoff, I. et al., Phase 1 study of AG-881, an inhibitor of mutant IDH1 and IDH2: results from the recurrent/progressive glioma population, Presentation ACTR-31, 23rd Annual Scientific Meeting and Education Day of the Society for Neuro-oncology (SNO), Nov. 15- 18, 2018, New Orleans, LA, USA (2018).

Mellinghoff, I.K. et al., A phase 1, open-label perioperative study of ivosidenib (AG-120) and vorasidenib (AG-881) in recurrent, IDH1-mutant, low-grade glioma: Results from Cohort 1, Presented at the American Society of Clinical Oncology (ASCO) Annual Meeting, May 21-Jun. 3, 2019, Chicago, IL, USA.

Mellinghoff, I.K. et al., Phase 1 study of AG-881, an inhibitor of mutant IDH1/IDH2, in patients with advanced IDH-mutant solid tumors, including glioma, 2018 ASCO Annual Meeting, J Clin Oncol., 36: (Abstract 2002), 2 pages (Jun. 1, 2018). URL: https://meetinglibrary.asco.org/record/162680/abstract [Retrieved Jun. 7, 2018].

Metallo, C.M. et al, Reductive glutamine metabolism by IDH1 mediates lipogenesis under hypoxia, Nature, 481(7381):380-384 (2011).

Meth-Cohn, O. and Stanforth, S. P. The Vilsmeier—Haack reaction (Review), Compr. Org. Synth., 2: 777-779 (1991).

Mohamed, E.A. et al., CA Accession No. 122:160601, abstract only of Indian J Chem, Sect B: Org Chem Inc Med Chem, 34B(1): 21-26 (1995).

Molenaar, R.J. et al., Wild-type and mutated IDH1/2 enzymes and therapy responses, Oncogene, 37: 1949-1960 (2018).

Morshed, M.N. et al., Computational approach to the identification of novel Aurora-A inhibitors, Bioorg & Med Chem, 19: 907-916 (2011).

National Comprehensive Cancer Network, Inc., NCCN Clinical Practice Guidelines in Oncology (NCCN Guidelines®), Acute Myeloid Leukemia, Version 2.2018 (Aug. 1, 2018).

Nicolay, B. et al., Combined use of the pan-IDH mutant inhibitor AG-881 with radiation therapy shows added benefit in an orthotopic IDH1 mutant glioma model in vivo, Poster EXTH-34, Presented at the 22nd Annual Scientific Meeting and Education Day of the Society for Neuro-oncology, Nov. 16-19, 2017, San Francisco, CA, USA (2017).

Nicolay, B. et al., The IDH1 mutant inhibitor AG-120 shows strong inhibition of 2-HG production in an orthotopic IDH1 mutant glioma model in vivo, EXTH-59, Presented at the 22nd Annual Scientific Meeting and Education Day of the Society for Neuro-oncology, Nov. 16-19, 2017, San Francisco, CA, USA (2017).

Okoye-Okafor , U.C. et al., New IDH1 mutant inhibitors for treatment of acute myeloid leukemia, Nat. Chem. Biol., 11: 878-886 (2015).

Oran, B. and Weisdorf, D. Survival for older patients with acute myeloid leukemia: a population-based study, Haematologica, 97: 1916-1924 (2012).

Pansuriya, T.C. et al., Somatic mosaic IDH1 and IDH2 mutations are associated with enchondroma and spindle cell hemangioma in Ollier disease and Maffucci syndrome, Nature Genetics, 43(12): 1256-1261 (2011).

Parsons, D.W. et al., An Integrated Genomic Analysis of Human Glioblastoma Multiforme, Science, 321(5897): 1807, 15 pages (2008).

Paschka, P. et al., IDH1 and IDH2 mutations are frequent genetic alterations in acute myeloid leukemia and confer adverse prognosis in cytogenetically normal acute myeloid leukemia with NPM1 mutation without FLT3 internal tandem duplication, J Clin Oncol., 22: 3636-3643 (2010).

Pelosi, E. et al., Isocitrate dehydrogenase mutations in human cancers: physiopathologic mechanisms and therapeutic Targeting. Journal of Exploratory Research in Pharmacology, 1: 20-34 (2016).

Penard-Lacronique, V. and, Bernard, O.A., IDH1, Histone Methylation, and So Forth, Cancer Cell, 30: 192-194 (2016).

Peng, D. et al., Epigenetic silencing of Th1 type chemokines shapes tumor immunity and immunotherapy, Nature, 527(7577): 249-253 (2015).

Pollyea, D.A. et al., Ivosidenib (AG-120) in Mutant IDH1 Relapsed/Refractory Acute Myeloid Leukemia: Results of a Phase 1 Study, European Hematology Association, Abstract S1560, 2(S1): 718 (2018).

Pollyea, D.A. et al., Ivosidenib (IVO; AG-120) in mutant IDH1 relapsed/refractory acute myeloid leukemia (R/R AML): Results of a phase 1 study, 2018 ASCO Annual Meeting, J Clin Oncol., 36 (Abstract 7000), 2 pages (Jun. 2, 2018). URL: https://meetinglibrary.asco.org/record/161682/abstract [Retrieved Jun. 7, 2018].

Popovici-Muller, J. et al., Discovery of AG-120 (Ivosidenib): A First-in-Class Mutant IDH1 Inhibitor for the Treatment of IDH1 Mutant Cancer, ACS Med. Chem. Lett., 9(4): 300-305 (2018).

Popovici-Muller, J. et al., Discovery of the First Potent Inhibitors of Mutant IDH1 That Lower Tumor 2-HG in Vivo, ACS Med. Chem. Lett., 3(10): 850-855 (2012).

Prensner, J.R. and Chinnaiyan, A.M., Metabolism unhinged: IDH mutations in cancer, Nature Medicine, 17(3): 291-293 (2011).

Prostakov, N.S. et al., Chemistry of Heterocyclic Compounds, CHCCAL, 22(7): 685-810 (1986).

(56) References Cited

OTHER PUBLICATIONS

Pusch, S. et al., Pan-mutant IDH1 inhibitor BAY 1436032 for effective treatment of IDH1 mutant astrocytoma in vivo. Acta Neuropathologica, 133(4): 629-644 (2017).
Ravandi, F. et al., Vosaroxin plus cytarabine versus placebo plus cytarabine in patients with first relapsed or refractory acute myeloid leukemia (VALOR): a randomized, controlled, double-blind, multinational, phase 3 study, Lancet Oncol., 16: 1025-1036 (2015).
Roboz, G.J. et al., International randomized Phase 2I study of elacytarabine versus investigator choice in patients with relapsed/refractory acute myeloid leukemia, J Clin Oncol., 20: 1919-1926 (2014).
Roboz, G.J. et al., Ivosidenib (AG-120) Induced Durable Remissions and Transfusion Independence in Patients with IDH1-Mutant Untreated AML: Results from a Phase 1 Dose Escalation and Expansion Study, ASH Annual Meeting, Blood, 132: Abstract 561 (2018).
Roboz, G.J. et al., Ivosidenib (AG-120) Induced Durable Remissions and Transfusion Independence in Patients with IDH1-Mutant Untreated AML: Results from a Phase 1 Dose Escalation and Expansion Study, Presentation, Presented at the 60th American Society of Hematology (ASH) Annual Meeting, Dec. 1-4, 2-18, San Diego, CA, USA, 16 pages, Abstract 561 (2018).
Rohle, D. et al., An Inhibitor of Mutant IDH1 Delays Growth and Promotes Differentiation of Glioma Cells, Science, 340(6132): 626-630 (2013). Supplementary Materials, 32 pages.
Rowe, J.M., AML in 2017: Advances in clinical practice, Best Practice & Research Clinical Haematology, 30: 283-286 (2017).
Saha, S.K. et al., IDH mutations in liver cell plasticity and biliary cancer, Cell Cycle, 13(20): 3176-3182 (2014).
Saha, S.K. et al., Mutant IDH inhibits HNF-4a to block hepatocyte differentiation and promote biliary cancer, Nature, 19 pages (2014).
Sasaki, M. et al., D-2-hydroxyglutarate produced by mutant IDH1 perturbs collagen maturation and basement membrane function, Genes & Development, 26: 2038-2049 (2012).
Sasaki, M. et al., IDH1(R132H) mutation increases murine haematopoietic progenitors and alters epigenetics, Nature, 488(7413): 656-659 (2012).
Schnittger, S. et al., IDH1 mutations are detected in 6.6% of 1414 AML patients and are associated with intermediate risk karyotype and unfavorable prognosis in adults younger than 60 years and unmutated NPM1 status, Blood, 116(25): 5486-5496 (2010).
Schrader, F.C. et al., Novel Type II Fatty Acid Biosynthesis (Fas II) Inhibitors as Multistage Antimalarial Agents, Chem Med Chem, 8: 442-461 (2013).
Segall, M., Multi-parameter Optimisation in Drug Discovery: Quickly targeting compounds with a good balance of properties, Optibrium Ltd, Elrig Drug Discovery 2011, 32 pages (Sep. 7, 2011).
Sellner, L. et al. Increased levels of 2-hydroxyglutarate in AML patients with IDH1-R132H and IDH2-R140Q mutations, Eur. J. Haematol., 85: 457-459 (2010).
Shibata, T. et al., Mutant IDH1 Confers an in Vivo Growth in a Melanoma Cell Line with BRAF Mutation, Am. J. Pathol., 178(3): 1395-1402 (2011).
Skrzypiec-Spring, M. et al., Isolated heart perfusion according to Langendorff—Still viable in the new millennium, Journal of Pharmacological and Toxicological Methods, 55: 113-126 (2007).
Sri Ramya, P.V. et al., Curcumin inspired 2-chloro/phenoxy quinoline analogues: Synthesis and biological evaluation as potential anticancer agents, Bioorganic & Medicinal Chemistry Letters 28: 892-898 (2018).
Stein, E. et al., AGILE: A phase 3, multicenter, randomized, placebo-controlled study of ivosidenib in combination with azacitidine in adult patients with previously untreated acute myeloid leukemia with an IDH1 mutation, Journal of Clinical Oncology, 36(15 suppl): Abstract TPS7074 (2018).
Stein, E. et al., AGILE: a phase 3, multicenter, randomized, placebo-controlled study of ivosidenib in combination with azacitidine in adult patients with previously untreated acute myeloid leukemia with an IDH1 mutation, Presented at the American Society of Clinical Oncology (ASCO) Annual Meeting, Chicago, IL, USA, Abstract TPS7074, J Clin Oncol 36, 2018 (Jun. 1-5, 2018).
Stein, E.M. et al., Ivosidenib or Enasidenib Combined with Induction and Consolidation Chemotherapy in Patients with Newly Diagnosed AML with an IDH1 or IDH2 Mutation is Safe, Effective, and Leads to MRD-Negative Complete Remissions, Poster Presented at the 60th American Society of Hematology (ASH) Annual Meeting, Dec. 1-4, 2018, San Diego, CA, USA, 21 pages, Abstract 560 (2018).
Stein, E.M. et al., Ivosidenib or Enasidenib Combined with Standard Induction Chemotherapy is Well Tolerated and Active in Patients with Newly Diagnosed AML with an IDH1 or IDH2 Mutation: Initial Results from a Phase 1 Trial, 2017 ASH Annual Meeting, Blood, 130: Abstract 726 (2017).
Stein, E.M. et al., Molecular remission and response patterns in patients with mutant-IDH2 acute myeloid leukemia treated with enasidenib, Blood, 133(7): 676-0867 (2019).
Stone, R.M. et al., Genetic Profiling and Deep IDH1 Mutation Clearance to =0.04 in Ivosidenib (AG-120)-Treated Patients with Mutant IDH1 Relapsed or Refractory and Untreated AML, 2017 ASH Annual Meeting, Blood, 130: Abstract 2684 (2017).
Struys, E.A. et al., Investigations by mass isotopomer analysis of the formation of D-2-hydroxyglutarate by cultures lymphoblasts from two patients with D-2-hydroxyglytaric aciduria, FEBS Letters, 557: 115-120 (2004).
Suman, P. et al., Synthesis and evaluation of functionalized aminobenzoboroxoles as potential anti-cancer agents, Journal of Organometallic Chemistry, 798(1): 125-131 (2015).
Talati, C. and Sweet, K., Recently approved therapies in acute myeloid leukemia: A complex treatment landscape, Leukemia Research, 73: 58-66 (2018).
Thompson, C.B., Metabolic Enxymes as Oncogenes or Tumor Suppressors, N Engl J Med, 360(8): 813-815 (2009).
Thomson, B. and Lipford, K., A Phase 1 b/2 Study of FT-2102 in Patients with Advanced Solid Tumors and Gliomas with an IDH1 Mutation, Poster Presented at the Cholangiocarcinoma Foundation Annual Conference, Salt Lake City, UT (Jan. 30, 2019).
Tintori, C. et al., Identification of Hck Inhibitors as Hits for the Development of Antileukemia and Anti-HIV Agents, Chem Med Chem, 8: 1353-1360 (2013).
Turcan, S. et al., Efficient induction of differentiation and growth inhibition in IDH1 mutant glioma cells by the DNMT Inhibitor Decitabine, Oncotarget, 4(10): 1729-1736 (2013).
Urban, D. J. et al., Assessing inhibitors of mutant isocitrate dehydrogenase using a suite of pre-clinical discovery assays, Scientific Reports 7(1): 12758 (2017).
Valle, J. et al., Cisplatin plus Gemcitabine versus Gemcitabine for Biliary Tract Cancer, N Engl J Med, 362: 1273-1281 (2010).
Venkanna, P. et al., 2,4,6-Trichloro-1,3,5-triazine and N,N'-dimethylformamide as an effective Vilsmeier—Haack reagent for the synthesis of 2-chloro-3-formyl quinolines from acetanilides, Tetrahedron Letters, 56(37): 5164-5167 (2015).
Vidaza, Azacitidine for injection; Drug Description, Manufactured for Pharmion Corporation, Manufactured by Ben Venue Laboratories, Inc., 19 pages (Edition Date: Jan. 9, 2007).
Vogelstein, B. and Kinzler, K.W., Digital PCR, Proc. Natl. Acad. Sci. USA, 96: 9236-9241 (1999).
Wager, T.T. et al., Defining Desirable Central Nervous System Drug Space through the Alignment of Molecular Properties, in Vitro ADME, and Safety Attributes, ACS Chem. Neurosci., 1:420-434 (2010).
Wager, T.T. et al., Moving beyond Rules: The Development of a Central Nervous System Multiparameter Optimization (CNS MPO) Approach to Enable Alignment of Druglike Properties. ACS Chem. Neurosci., 1(6): 435-449 (2010).
Wahl, D.R. et al., Glioblastoma Therapy Can be Augmented by Targeting IDH1-mediated NADPH Biosynthesis, Cancer Res, 77(4): 960-970 (2017).
Wakayama, M. and Ellman, J.A., Recycling the tert-Butanesulfinyl Group in the Synthesis of Amines Using tert-Butanesulfinamide, J. Org. Chem., 74: 2646-2650 (2009).

(56) References Cited

OTHER PUBLICATIONS

Wakimoto, H. et al., Targetable Signaling Pathway Mutations Are Associated with Malignant Phenotype in IDH-Mutant Gliomas, Clin Cancer Res, 20(11): 2898-2909 (2014).
Wang, F. et al., Targeted Inhibition of Mutant IDH2 in Leukemia Cells Induces Cellular Differentiation, Science, 340: 622-626 (2013).
Wang, P. et al., Mutations in Isocitrate Dehydrogenase 1 and 2 Occur Frequently in Intrahepatic Cholangiocarcinomas and Share Hypermethylation Targets with Glioblastomas, Oncogene, 32(25): 3091-3100 (2013).
Wang, R. et al., Rapid Ti(OiPr)4 facilitated synthesis of a,a,a-trisubstituted primary amines by the addition of Grignard reagents to nitriles under microwave heating conditions. Tetrahedron Letters, 50(50): 7070-7073 (2009).
Ward, P.S. et al., The common feature of leukemia-associated IDH1 and IDH2 mutations is a neomorphic enzymatic activity that converts α-ketoglutarate to 2-hydroxyglutarate, Cancer Cell, 17(3): 225-234 (2010).
Ward, P.S. et al., The Potential for Isocitrate Dehydrogenase Mutations to Produce 2-Hydroxyglutarate Depends on Allele Specificity and Subcellular Compartmentalization, The Journal of Biological Chemistry, 288(6): 3804-3815 (2013).
Watanabe, T. et al., IDH1 Mutations are early events in the Development of Astrocytomas and Oligodendrogliomas, American Journal of Pathology, 174(4): 1149-1153 (2009).
Waters, N.J. et al., Validation of a rapid equilibrium dialysis approach for the measurement of plasma protein binding, J Pharm Sci., 97(10): 4586-4595 (2008).
Watts, J.M. et al., A Phase 1 Dose Escalation Study of the IDH1m Inhibitor, FT-2102, in Patients with Acute Myeloid Leukemia or Myelodysplastic Syndrome, ASCO Abstract public release May 16, 2018, Presented Jun. 4, 2018, Clin Oncol 36, 2018 (suppl; abstr 7009).
Watts, J.M. et al., A Phase 1 Dose Escalation Study of the IDH1m Inhibitor, FT-2102, in Patients with Acute Myeloid Leukemia or Myelodysplastic Syndrome, Presented at the 2018 ASCO Annual Meetings, 19 pages (Jun. 4, 2018).
Watts, J.M. et al., Phase 1 Study of the IDH1m Inhibitor FT-2102 as a Single Agent in Patients with IDH1m Acute Myeloid Leukemia (AML) or Myelodysplastic Syndrome (MDS), ASH abstract available in online meeting program, 8 pages (submitted Jul. 31, 2018, published Nov. 1, 2018).
Watts, J.M. et al., Phase 1 Study of the IDH1m Inhibitor FT-2102 as a Single Agent in Patients with IDH1m Acute Myeloid Leukemia (AML) or Myelodysplastic Syndrome (MDS), Poster 1453, Presented at the 60th Annual Meeting of the American Society of Hematology, San Diego, CA (Dec. 1, 2018).
Wheeler, D.A. and Robers, L.R., The Cancer Genome Atlas Research Network, Comprehensive and Integrative Genomic Characterization of Hepatocellular Carcinoma, Cell, 169: 1327-1341 (2017).
Wu, F. et al., Inhibition of cancer-associated mutant isocitrate dehydrogenases by 2-thiohydantoin compounds, J. Med. Chem., 58: 6899-6908 (2015).
Xu, W. et al., Oncometabolite 2-Hydroxyglutarate is a Competitive Inhibitor of a-Ketoglutarate-Dependent Dioxygenases, Cancer Cell, 19: 17-30 (2011).
Xu, X. et al., Structures of human cytosolic NADP-dependent isocitrate dehydrogenase reveal a novel self-regulatory mechanism of activity, J Biol Chem., 279(32): 33946-33957 (2004).
Yamashita, A.S. et al., Demethylation and epigenetic modification with 5-azacytidine reduces IDH1 mutant glioma growth in combination with temozolomide, Neuro-Oncology, 21(2): 189-200 (2019).
Yan, H et al., IDH1 and IDH2 Mutations in Gliomas, The New England Journal of Medicine, 360(8):765-773 (2009).
Yang, H. et al., IDH1 and IDH2 Mutations in Tumorigenesis: Mechanistic Insights and Clinical Perspectives, Clin Cancer Res, 18(20): 5562-5571 (2012).
Yen, K. et al., Abstract 4956: Functional characterization of the ivosidenib (AG-120) and azacitidine combination in a mutant IDH1 AML cell model, Experimental and Molecular Therapeutics, Proceedings: AACR Annual Meeting 2018; Apr. 14-18, 2018; Chicago, IL (Published Jul. 2018).
Yen, K. et al., Abstract B126: AG-881, a brain penetrant, potent, pan-mutant IDH (mIDH) inhibitor for use in mIDH solid and hematologic malignancies, AACR-NCI-EORTC International Conference: Molecular Targets and Cancer Therapeutics (Oct. 26-30, 2017; Philadelphia, PA).
Zhao, S. et al., Glioma-Derived Mutations in IDH1 Dominantly Inhibit IDH1 Catalytic Activity and Induce HIF-1a, Science, 324(5924): 261-265 (2009).
Zheng, B. et al., Crystallographic Investigation and Selective Inhibition of Mutant Isocitrate Dehydrogenase, ACS Medicinal Chemistry Letters, 4(6): 542-546 (2013).
Caira, M.R. et al., Crystalline polymorphism of organic compounds, Topics in Current Chemistry, 198: 163-208 (1998).
International Search Report for PCT/US2019/032742, 4 pages (dated Jul. 29, 2019).
International Search Report for PCT/US2019/032747, 5 pages (dated Aug. 1, 2019).
Olutasidenib, C18H15ClN4O2, PubChem, Compound Summary, 10 pages (retrieved Jul. 24, 2019).
Leese, C. L. and Rydon, H.N., Polyazanaphthalenes. Part I. Some derivatives of 1:4:5-triazanaphthalene and quinoxaline, PolyJournal of the Chemical Society, 303-309 (1995).
Mamedov, V. A. et al., Synthesis and Functionalization of 3-Ethylquinoxalin-2(1H)-one, Russian Journal of Organic Chemistry, 41(4): 599-606 (2005).
U.S. Appl. No. 16/712,951, Lin et al.
Caravella, J. A. et al., Structure-based design and identification of FT-2102 (olutasidenib), a potent mutant-selective IDH1 inhibitor, J Med Chem, doi: 10.1021/acs.jmedchem.9b01423, Epub ahead of print (2020).
Cortes, J.E. et al., Olutasidenib (FT-2102) Induces Rapid Remissions in Patients with IDH1-Mutant Myelodysplastic Syndrome: Results of Phase 1/2 Single Agent Treatment and Combination with Azacitidine, ASH Annual Meeting, Oral and Poster Abstract, Abstract 674 (Dec. 9, 2019).
De La Fuente, M.I. et al., Phase 1 b/2 Study of Olutasidenib (FT-2102), an Inhibitor of Mutant IDH1, in Patients with Relapsed/Refractory IDH1-Mutant Gliomas: Preliminary Safety and Clinical Activity, Presented at the Society for NeuroOncology, Phoenix, AZ, Nov. 20-24, 2019 (Presented on Nov. 21, 2019).
Ribadeneira, M. et al., SCIDOT-42. FT-2102—A Potent and Selective Brain Penetrant Inhibitor of Mutant Isocitrate Dehydrogenase, Neuro-Oncology, 21(Supplement 6): vi280 3 pages (2019).
Seltzer, M.J. et al., Inhibition of Glutaminase Preferentially Slows Growth of Glioma Cells with Mutant IDH1, Cancer Research, 70(22): 8981-8987 (2010).
U.S. Appl. No. 16/414,505 Final Rejection, 8 pages (dated Jan. 16, 2020).
U.S. Appl. No. 16/414,505 Non-Final Rejection, 11 pages (dated Aug. 26, 2019).
Watts, J.M. et al., Olutasidenib (FT-2102), an IDH1 m Inhibitor as a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral and Poster Abstract, Abstract 231 (Dec. 7, 2019).
Wick, W. et al., New (alternative) temozolomide regimens for the treatment of glioma, Neuro-Oncology, 11:69-79 (2009).
U.S. Appl. No. 16/893,147, Kelly et al.
Abbott Molecular Inc, U.S. Food and Drug Administration Approval Letter, 4 pages (2018), <https://www.accessdata.fda.gov/cdrh_docs/pdf17/P170041A.pdf> [Retrieved Jul. 28, 2020].
Abbott Molecular Inc., Summary of Safety and Effectiveness Data (SSED), 43 pages (2018), <https://www.accessdata.fda.gov/cdrh_docs/pdf17/P170041B.pdf> [Retrieved Jul. 28, 2020].
Agios Pharmaceuticals, Press Release, Celgene and Agios Announce Collaborations with Abbott for Diagnostic Identification of IDH Mutations in AML, 4 pages (Summit, N.J. and Cambridge, Mass., Oct. 12, 2016). URL: <https://investor.agios.com/news-releases/

(56) References Cited

OTHER PUBLICATIONS news-release-details/celgene-and-agios-announce-collaborations-abbott-diagnostic> [Retrieved Jul. 28, 2020].
Agios Pharmaceuticals, Press Release, FDA Accepts New Drug Application and Grants Priority Review for Ivosidenib in Relapsed or Refractory AML with an IDH1 Mutation, 4 pages (Summit, N.J. and Cambridge, Mass., Feb. 15, 2018). URL: <https://investor.agios.com/news-releases/news-release-details/fda-accepts-new-drug-application-and-grants-priority-review-0> [Retrieved Jul. 28, 2020].
Agios Pharmaceuticals, Press Release, FDA Grants Approval of TIBSOVO®, the First Oral, Targeted Therapy for Adult Patients with Relapsed/Refractory Acute Myeloid Leukemia and an IDH1 Mutation , 9 pages (Cambridge, Mass., Jul. 20, 2018). URL: <https://investor.agios.com/news-releases/news-release-details/fda-grants-approval-tibsovor-first-oral-targeted-therapy-adult> [Retrieved Jul. 28, 2020].
Blackburn, C. et al., Identification and characterization of amino-piperidinequinolones and quinazolinones as MCHr1 antagonists, Bio. and Med. Chem. Letters, 16(10):2621-2627 (2006).
De La Fuente, M. et al., A Phase 1 b/2 Study of Olutasidenib in Patients with Relapsed/Regractory IDH1 Mutant Gliomas: Safety and Clinical Activity as a Single Agent and in Combination with Azacitidine, ASCO, slides 1-13, May 2020.
De La Fuente, M.I. et al., A phase ib/II study of olutasidenib in patentis with relapsed/refractory IDH1 mutant gliomas: Safety and efficacy as single agent and in combination with azacitidine, Amer. Soc. Clin. Oncol. (2020), Abstract, <https://meetinglibrary.asco.org/record/185065/abstract>. Retrieved on May 13, 2020.
Golub, D. et al., Mutant Isocitrate Dehydrogenase Inhibitors as Targeted Cancer Therapeutics, Front. Oncol., Article 417, 1-25 (2019).
Gu, X. et al., MicroRNA-129-5p inhibits human glioma cell proliferation and induces cell cycle arrest by directly targeting DNMT3A, AM. J. Transl. Res., 10(9):2834-2847 (2018).
Huang, J. et al., Isocitrate Dehydrogenase Mutations in Glioma: From Basic Discovery to Therapeutics Development, Front. Oncol., Article 506, 9:1-7 (2019).
International Search Report for PCT/US2020/033212, 6 pages (dated Jul. 20, 2020).
Jones, R.L. et al., A phase ib/II study of olutasidenib in patients with relapsed/refractory IDH1 mutant solid tumors: Safety and efficacy as single agent, Amer. Soc. Clin. Oncol. (2020), Abstract, <https://meetinglibrary.asco.org/record/186633/abstract>. Retrieved on May 13, 2020.
Lin, J. et al., Discovery and Optimization of Quinolinone Derivatives as Potent, Selective, and Orally Bioavailable Mutant Isocitrate Dehydrogenase 1 (mIDH1) Inhibitors, J. Med. Chem., 62(14):6575-6596 (2019).
Megias-Vericat, J.E., et al., IDHI-mutated relapsed or refractory AML: current challenges and future prospects, Blood and Lymphatic Cancer: Targets and Therapy, 9:19-32 (2019).
Mellai, M., et al., The Distribution and Significance of IDH Mutations in Gliomas, Evolution of the Molecular Biology of Brain Tumors and the Therapeutic Implications, Terry Lichtor, IntechOpen, DOI: 10.5772/52357, 23 pages (2013).
Panknin, O. et al., Abstract 2645: BAY 1436032: A highly selective, potent and orally available inhibitor of mutant forms of IDH1, AACR 107th Annual Meeting Apr. 16-26 2016, 4 pages.
Pleyer, L., et al., Azacitidine for Front-Line Therapy of Patients with AML: Reproducible Efficacy Established by Direct Comparison of International Phase 3 Trial Data with Registry Data form the Austrian Azacitidine Registry of the AGMT Study Group, J. Mol. Sci., 18(415):118 (2017).
Press Release, Forma Therapeutics Announces Clinical Data to be Presented at ASCO20 Virtual Scientific Program (2020), Forma Therapeutics, <https://www.formatherapeutics.com/press-releases/forma-therapeutics-announces-clinical-data-to-be-presented-at-asco20-virtual-scientific-program>. Retrieved Jun. 5, 2020.
Reitman, Z.J. and Yan, H, Isocitrate Dehydrogenase 1 and 2 Mutations in Cancer: Alterations at a Crossroads of Cellular Metabolism, J. Natl. Cancer Inst., 102:932-941 (2010).
U.S. Appl. No. 16/414,505 Non-Final Rejection, 15 pages (dated Jul. 7, 2020).
U.S. Appl. No. 16/431,588 Non-Final Rejection, 47 pages (dated Jul. 14, 2020).
Wai, J. et al., Synthesis and evaluation of 2-pyridinone derivatives as specific HIV-1 reverse transcriptase inhibitors. 3. Pyridyl and phenyl analogs of 3-aminopyridin-2(1H)-one, J. Med. Chem., 36(2):249-255 (1993).
Wang, M. et al., Molecular Mutation and Their Cooccurrences in Cytogenetically Normal Acute Myeloid Leukemia, Hindawi Publishing Stem Cells International, 1-11 (2017).
Watts, J.M. et al., Olutasidenib (Ft-2102), an IDH1m Inhibitor as a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral Presentation, 14 pages (Dec. 7, 2019).
Yu, J. et al., Clinical implications of recurrent gene mutations in acute myeloid leukemia, Exp. Hematol. Oncol., 9:1-11 (2020).
U.S. Appl. No. 16/431,588 Response to Non-Final Rejection, 19 pages (filed Sep. 4, 2020).
U.S. Appl. No. 16/693,585 Non-Final Rejection, 16 pages (dated Sep. 2, 2020).
U.S. Appl. No. 16/693,585 Response to Non-Final Rejection, 16 pages (filed Sep. 23, 2020).
U.S. Appl. No. 16/693,585 Non-Final Rejection, 30 pages (dated Nov. 20, 2020).
U.S. Appl. No. 16/893,147 Non-Final Rejection, 41 pages (dated Nov. 30, 2020).
U.S. Appl. No. 17/112,269, Kelly et al.
Bleeker, F.E. et al., $IDH^{R132}$ mutations occur frequently in high-grade gliomas but not in other solid tumors, Human Mutation, 30:84-91 (2009).
ClinicalTrials.gov Indentifier: NCT00900224, "Studying Tissue and Blood Samples from Patients with Acute Myeloid Leukemia," (v40 dated Dec. 15, 2010; updated posted Dec. 16, 2010) https://clinicaltrials.gov/ct2/history/NCT00900224?V=View.
Struys, E.A. et al., Mutations in the D-2-Hydroxyglutarate Dehyrdogenase Gene Cause D-2-Hydroxyglutaric Aciduria, Am. J. Hum. Genet., 76:358-360 (2005).
Tibsovo Prescription Label, 20 pages (issued Jul. 20, 2018), <https://www.accessdata.fda.gov/drugsatfda_docs/label/2018/211192s000lbl.pdf>.
U.S. Appl. No. 17/055,278, Kelly et al.
A Study of FT-2012 in Patients with Advanced Solid Tumors and Gliomas, Spanish Clinical Studies Registry, retrieved from https://reec.aemps.es/reec/public/detail.html, 16 pages (2019).
AbbVie, AbbVie Receives EMA and FDA Orphan Drug Designation for Investigational Compound ABT-414 in the Treatment of Glioblastoma Multiforme, 4 pages (Aug. 4, 2014). URL: https://www.prnewswire.com/new-releases/abbvie-receives-ema-and-fda-orphan-drug-designation-for-investigational-compound-abt-414-in-the-treatment-of-glioblastoma-multiforme-269807321.html.
AbbVie, AbbVie Receives U.S. FDA Rare Pediatric Disease Designation for Investigational ABT-414 for the Treatment of Pediatric Brain Tumor known as Diffuse Intrinsic Pontine Glioma (DIPG), 3 pages (Jul. 11, 2016). URL: https://news.abbvie.com/article_print.cfm?article_id=11360.
Agios Pharmaceuticals, Press Release, Agios Presents Updated Data from Phase 1 Dose-Escalation Study of AG-881 in Patients with IDH Mutant Positive Advanced Glioma, 6 pages (Nov. 16, 2018). URL: https://investor.agios.com/news-releases/news-release-details/agios-presents-updated-data-phase-1-dose-escalation-study-ag-881.
Agios Pharmaceuticals, Third Quarter 2018 Financial Results, 27 pages (Nov. 1, 2018).
Agios Pharmaceuticals, TIBSOVO® (ivosidenib) FDA Approval, 17 pages (Jul. 20, 2018).
Bayer, Interim Report Third Quarter of 2018, 61 pages (2018).

(56) References Cited

OTHER PUBLICATIONS

ClinicalTrials.gov Identifier: NCT01800695, Evaluating the Safety and Pharmacokinetics of ABT-414 for Subjects With Glioblastoma Multiforme (First Posted Feb. 28, 2013, Last Update Posted Nov. 21, 2017), URL: https://clinicaltrials.gov/ct2/show/NCT01800695.

ClinicalTrials.gov Identifier: NCT02073994, Study of Orally Administered AG-120 in Subjects With Advanced Solid Tumors, Including Glioma, With an IDH1 Mutation (First Posted Feb. 28, 2014, Last Update Posted Dec. 9, 2020). URL: https://clinicaltrials.gov/ct2/show/NCT02073994.

ClinicalTrials.gov Identifier: NCT02074839, Study of Orally Administered AG-120 in Subjects With Advanced Hematologic Malignancies With an IDH1 Mutation (First Posted Feb. 28, 2014, Last Update Posted Feb. 5, 2020). URL: https://clinicaltrials.gov/ct2/show/NCT02074389?term=NCT02074839&draw=2&rank=1.

ClinicalTrials.gov Identifier: NCT02193347, IDH1 Peptide Vaccine for Recurrent Grade II Glioma (RESIST) (First Posted Jul. 17, 2014, Last Update Posted May 13, 2020). URL: https://clinicaltrials.gov/ct2/show/NCT02193347.

ClinicalTrials.gov Indentifier: NCT02841154, Study of Orally Administered AG-881 in Patients With Advanced Solic Tumors, Including Gliomas, With an IDH1 and/or IDH2 Mutation (First Posted Jun. 25, 2015, Last Update Posted Dec. 17, 2020). URL: https://clinicaltrials.gov/ct2/show/NCT02481154.

ClinicalTrials.gov Identifier: NCT02492737, Study of Orally Administed AG-881 in Patients With Advanced Hematologic Malignancies With An IDH1 and/or IDH2 Mutation (First Posted Jul. 9, 2015, Last Update Posted Mar. 8, 2019). URL: https://clinicaltrials.gov/ct2/show/NCT02492737?term=NCT02492737&draw=2&rank=1.

ClinicalTrials.gov Identifier: NCT02511405, A Phase 3, Pivotal Trial of *VB-111 Plus Bevacizumanv. Bevacizumab* in Patients With Recurrent Glioblastoma (GLOBE) (GLOBE) (First Posted Jul. 30, 2015, Last Update Posted Oct. 23, 2018). URL: https://clinicaltrials.gov/ct2/show/NCT02511405?term=VB-111.

ClinicalTrials.gov Indentifier: NCT02573324, A Study of ABT-414 in Participants With Newly Diagnosed Glioblastoma (GBM) With Epidermal Growth Factor Receptor (EGFR) Amplification (Intellance1) (First Posted Oct. 9, 2015, Last Update Posted Dec. 21, 2020). URL: https://clinicaltrials.gov/gov/ct2/show/NCT02573324?term=ABT-414&rank=6.

ClinicalTrials.gov Identifier: NCT02677922, A Safety and Efficacy Study of Oral AG-120 Plus Subcutaneous Azacitidine and Oral AG-221 Plus Subcutaneous Azacitidine in Subjects With Newly Diagnozed Acute Myeloid Leukemia (AML) (First Posted Feb. 9, 2016, Last Update Posted Dec. 20, 2019). URL: https://clinicaltrials.gov/ct2/show/NCT02677922.

ClinicalTrials.gov Identifier: NCT02746081, Phase I Study of BAY1436032 in IDH1-mutant Advanced Solid Tumors (First Posted Apr. 21, 2016, Last Update Posted Dec. 22, 2020). URL: https://clinicaltrials.gov/ct2/show/NCT02476081.

ClinicalTrials.gov Identifier: NCT02771301, Safety and Efficacy of IDH1R123H-DC Vaccine in Gliomas (First Posted May 13, 2016, Last Update Posted May 13, 2016). URL: https://clinicaltrials.gov/ct2/show/NCT02771301.

ClinicalTrials.gov Identifier: NCT02989857, Study of AG-120 in Previously Treated Advaned Cholangiocarcinoma With IDH1 Mutations (ClarIDHy) (ClarIDHy) (First Posted Dec. 12, 2016, Last Update Posted Dec. 1, 2020). URL: https://clinicaltrials.gov/ct2/show/NT02989857.

ClinicalTrials.gov Identifier: NCT03030066, Study of D3-1001b in Patients With Gene IDH1-Mutated Gliomas (First Posted Jan. 24, 2017, Last Update Posted Feb. 28, 2020). URL: https://clinicaltrials.gov/ct2/shows/NCT03030066.

ClinicalTrials.gov Identifier: NCT03149575, VAL-083 Phase 3 Study in Temozolomide-Avastin (Bevacizumab) Recurrent GBM (STAR-3) (First Posted May 11, 2017, Last Update Posted Nov. 14, 2019). URL: https://clinicaltrials.gov/ct2/show/NCT03149575?term=VAL-083&rank=6.

ClinicalTrials.gov Identifier: NCT03173248, *Study of AG-120 (Ivosidenib)*v. *Placebo* in Combination With Azacitidine in Patients With Previously Untreated Acute Myeloid Leukemia With an IDH1 Mutation (AGILE) (First Posted Jun. 1, 2017, Last Update Posted Dec. 24, 2020). URL: https://www.clinicaltrials.gov/ct2/show/NCT03173248.

ClinicalTrials.gov Identifier: NCT03343197, Study of AG-120 and AG-881 in Subjects With Low Grade Glioma (First Posted Nov. 17, 2017, Last Update Posted Oct. 5, 2020). URL: https://clinicaltrials.gov/ct2/show/NCT03343197.

ClinicalTrials.gov Identifier: NCT03393000, Safety and Efficacy Study of Trans Sodiu Crocetinate (TSC) in Newly Diagnozed Glioblastoma (GBM) Biopsy-Only Subjects (INTACT) (First Posted Jan. 8, 2018, Last Update Posted Jan. 28, 2020). URL: https://clinicaltrials.gov/ct2/show/record/NCT03393000?term=trans+sodium+crocetinate&rank=1&view=record.

ClinicalTrials.gov Identifier: NCT03398655, A Study of VB-111 With *Paclitaxel*vs *Paclitaxel* for Treatment of Recurrent Platinum-Resistent Ovarian Cancer (OVAL) (OVAL) (First Posted Jan. 12, 2018, Last Update Posted Jan. 1, 2021). URL: https://clinicaltrials.gov/ct2/show/NCT03398655?term=VB-111.

DelMar Pharmaceuticals, Inc., DelMar Pharmaceuticals Announces Fast Track Designatuion for VAL-083 in Recurrent Glioblastoma, 5 pages (Dec. 16, 2017).

Gainer, J.L. et al., Trans sodium crocetinate with temozolomide and radiation therapy for glioblastoma multiforme, J. Neurosurg, 126:460-466 (2017).

Gormley, G., Research and Development at Daichii Sankyo, Daiichi-Sankyo, 70 pages (2014). URL: https://daiichisankyo.com/files/news/ir/pdf/005258/R&D%20Day_eng.pdf.

Gruslove, A. et al., VB-111: a novel anti-vascular therapeutic for glioblastoma multiforme, J Neurooncol., 124(3):365-372 (2015).

Katz, A., Novel Alkylating Agent Defies Mechanisms of Resistance in GBM Tumors, OncologyLive, 18(19): (Oct. 11, 2017).

Kintara Therapeutics, DelMar Presents Clinical Update on VAL-083 From Ongoing First- and Second-Line Trials in Pateitn wioth MGMT-unmethylated GBM at The Society for NeuroOncology Annual Meeting, 5 pages (Nov. 20, 2018). URL: https://www.kinatra.com/news-media/press-releases/detail/887/delmar-presents-clinical-update-on-val-083-from-ongoing.

Mellinghoff, I.K. et al., A phase 1, multicenter, randomized, open-label, perioperative study of AG-120 (ivosidenib) and AG-881 in patients with recurrent, nonenhancing, IDH1-mutant, low-grade glioma, Presented at the 23rd Annual Scientific Meeting and Education Day of the Society for Neuro-oncology (SNO), New Orleans, LA, USA, Poster RBTT-03 (Nov. 15-18, 2018).

Mellinghoff, I.K. et al., AG-120, a first-in-class mutant IDH1 inhibitor in patients with current or progressive IDH1 mutant glioma: results from the phase 1 glioma expansion cohorts, Presented at the Society for Neuro-Oncology Annual Scientific Meeting, Scottsdale, AZ, ACTR-46, 19 pages (Nov. 18, 2016).

Mohamed, H and Duffy-Warren, F., FT-2102—mIDH1 Inhibitor, Forma Therapeutics presentation, 4th Paediatric Strategy Forum for Medicinal Product Development for Acute Myeloid Leykaemia in Children and Adolescents, Erasmus University Rotterdarm, 7 pages (Apr. 11, 2019).

Reardon, D.A. et al., Efficacy and safety results of ABT-414 in combination with radiation and temozolomide in newly diagnosed glioblastoma, Neuro-Oncology, 19(7):965-975 (2016).

Ribadeneira, M.D. et al., Olutasidenib (FT-2012) A Potent and Selective Brain Penetrant Inhibitor of Mutant Isocitrate Dehydrogenase 1, Forma Therapeutics, Inc., Presented at 3rd SNO-SCIDOT Joint Conference on Therapeutic Delivery to the CNS, 9 pages (Nov. 20, 2019).

Shanley, M., Phase 3 Results Reveal Combination Therapy Does Not Improve Overall Survival in Glioblastoma, HCP Live, 2 pages (Mar. 8, 2018). URL: https://www.hcplive.com/view/vb-111-combination-glioblastoma-fail.

Study to evaluate FT-2012 as a single agent or in combination with Azacitidine or Cytarabine in patients with Acute Myeloid Leukemia or Myelodysplastic Syndrome, Spanish Clinical Studies Registry, retrieved from https://reec.aemps.es/reec/public/detail.html, 14 pages (2018).

The Brain Tumour Charity, Positive results from a drug treating recurrent glioblastoma, (Jun. 28, 2018) URL: https://news.abbvie.

(56) References Cited

OTHER PUBLICATIONS com/news/abbvie-receives-us-fda-rare-pediatric-disease-designation-for-investigational-abt-414-for-treatment-type-pediatric-brain-tumor-known-as-diffuse-intrinsic-pontine-glioma-dipg.htm.
U.S. Appl. No. 16/414,505 Response to Non-Final Rejection, 11 pages (filed Jan. 7, 2021).
U.S. Appl. No. 16/414,505 Response to Non-Final Rejection, 17 pages (filed Mar. 3, 2020).
U.S. Appl. No. 16/414,505 Response to Non-Final Rejection, 17 pages (filed Nov. 25, 2019).
U.S. Appl. No. 16/431,588 Notice of Allowance, 20 pages (dated Dec. 15, 2020).
U.S. Food and Drug Administration, FDA approves ivosidenib for relapsed or refractory acute myeloid leukemia, 2 pages (Content current as of Jan. 23, 2019). URL: https://www.fda.gov/drugs/resources-information-approved-drugs/fda-approves-ivosidenib-relapsed-or-refractory-acute-myeloid-leukemia.
U.S. Food and Drug Administration, ivosidenib, Treatment of acute myeloid leukemia (AML), 2.
pages (Date Designated Jun. 9, 2015). URL: https;//www.accessdata.fda.gov/scripts/opdlisting/oopd/detailedIndex.cfm?cfgridkey=481515.
U.S. Food and Drug Administration, ivosidenib, Treatment of cholangiocarcinoma, 1 page (Date Designated Apr. 26, 2017). URL: https://www.accessdata.fda.gov/scripts/opdlisting/oopd/detailedIndex.cfm?cfgridkey=562216.
U.S. Food and Drug Administration, ivosidenib, Treatment of glioma, 1 page (Date Designated May 1, 2018). URL: https://www.accessdata.fda.gov/scripts/opdlisting/oopd/detailedIndex.cfm?cfgridkey=637718.
U.S. Food and Drug Administration, vorasidenib, Treatment of giloma, 1 page (Date Designated Sep. 10, 2018). URL: https://www.accessdata.fda.gov/scripts/opdlisting/oopd/detailedIndex.cfm?cfgridkey=649318.
VBL Therapeutics, Data Demonstrate Strengthened Overall Survival Benefit in Patients Treated With VB-111 in Combination With Bevacizumab, 4 pages (Jun. 1, 2015). URL: vblrx.com/vbl-therapeutics-reports-updated-interim-results-from-phase-2-clinical-trial-of-vb-111-in-recurrentglioblastoma-rgdm/.
VBL Therapeutics, VBL Therapeutics Announces Third Quarter 2018 Financial Results, 6 pages (Nov. 20, 2018). URL: https://www.globenewswire.com/news-release/2018/11/20/1654366/0/en-VBL-Therapeutics-Announces-Third-Quarter-2018-Financial-Results.html.
U.S. Appl. No. 16/141,505 Final Rejection, 14 pages (dated Feb. 18, 2021).
U.S. Appl. No. 16/414,505 Final Rejection, 8 pages (dated Feb. 22, 2021).

* cited by examiner

C1: Gr 3 IDH-DS Resolved with Dexamethasone and Hydroxyurea

TREATING PATIENTS HARBORING AN ISOCITRATE DEHYDROGENASE-1 (IDH-1) MUTATION

CROSS REFERENCE TO RELATED APPLICATIONS

This application claims the benefit of and priority to U.S. Provisional Application No. 62/712,160, filed Jul. 30, 2018, which is incorporated by reference herein in its entirety; and this application is a continuation-in-part of U.S. application Ser. No. 16/414,505, filed May 16, 2019, and International Application No. PCT/US19/32747, filed May 16, 2019, each of which claims the benefit of and priority to U.S. Provisional Application No. 62/672,461, filed May 16, 2018; U.S. Provisional Application No. 62/672,462, filed May 16, 2018; U.S. Provisional Application No. 62/680,566, filed Jun. 4, 2018; U.S. Provisional Application No. 62/680,571, filed Jun. 4, 2018; U.S. Provisional Application No. 62/680,560, filed Jun. 4, 2018; U.S. Provisional Application No. 62/680,562, filed Jun. 4, 2018; U.S. Provisional Application No. 62/692,598, filed Jun. 29, 2018; U.S. Provisional Application No. 62/692,601, filed Jun. 29, 2018; U.S. Provisional Application No. 62/692,604, filed Jun. 29, 2018; U.S. Provisional Application No. 62/692,605, filed Jun. 29, 2018; U.S. Provisional Application No. 62/692,591, filed Jun. 29, 2018; U.S. Provisional Application No. 62/773,562, filed Nov. 30, 2018; U.S. Provisional Application No. 62/798,677, filed Jan. 30, 2019; U.S. Provisional Application No. 62/798,681, filed Jan. 30, 2019; U.S. Provisional Application No. 62/798,684, filed Jan. 30, 2019; U.S. Provisional Application No. 62/798,687, filed Jan. 30, 2019; U.S. Provisional Application No. 62/798,690, filed Jan. 30, 2019; and U.S. Provisional Application No. 62/812,367, filed Mar. 1, 2019; and this application is a continuation-in-part of U.S. application Ser. No. 16/431,588, filed Jun. 4, 2019, which claims the benefit of and priority to U.S. Provisional Application No. 62/701,487, filed Jul. 20, 2018; and U.S. Provisional Application No. 62/712,160, filed Jul. 30, 2018; and is a continuation-in-part of U.S. application Ser. No. 16/414,505, filed May 16, 2019, and International Application No. PCT/US19/32747, filed May 16, 2019, each of which claims the benefit of and priority to U.S. Provisional Application No. 62/672,461, filed May 16, 2018; U.S. Provisional Application No. 62/672,462, filed May 16, 2018; U.S. Provisional Application No. 62/680,566, filed Jun. 4, 2018; U.S. Provisional Application No. 62/680,571, filed Jun. 4, 2018; U.S. Provisional Application No. 62/680,560, filed Jun. 4, 2018; U.S. Provisional Application No. 62/680,562, filed Jun. 4, 2018; U.S. Provisional Application No. 62/692,598, filed Jun. 29, 2018; U.S. Provisional Application No. 62/692,601, filed Jun. 29, 2018; U.S. Provisional Application No. 62/692,604, filed Jun. 29, 2018; U.S. Provisional Application No. 62/692,605, filed Jun. 29, 2018; U.S. Provisional Application No. 62/692,591, filed Jun. 29, 2018; U.S. Provisional Application No. 62/773,562, filed Nov. 30, 2018; U.S. Provisional Application No. 62/798,677, filed Jan. 30, 2019; U.S. Provisional Application No. 62/798,681, filed Jan. 30, 2019; U.S. Provisional Application No. 62/798,684, filed Jan. 30, 2019; U.S. Provisional Application No. 62/798,687, filed Jan. 30, 2019; U.S. Provisional Application No. 62/798,690, filed Jan. 30, 2019; and U.S. Provisional Application No. 62/812,367, filed Mar. 1, 2019;

and is a continuation-in-part of U.S. application Ser. No. 16/414,716, filed May 16, 2019, and International Application No. PCT/US19/32742, filed May 16, 2019, each of which claims the benefit of and priority to U.S. Provisional Application No. 62/672,461, filed on May 16, 2018; U.S. Provisional Application No. 62/672,462, filed on May 16, 2018; and U.S. Provisional Application No. 62/692,591, filed on Jun. 29, 2018;

the contents of each of the applications listed above are hereby incorporated by reference in their entirety.

TECHNICAL FIELD

This disclosure relates to the treatment of acute myeloid leukemia (AML) or myelodysplastic syndrome (MDS). For example, the disclosure provides methods of treating AML or MDS in patients diagnosed as harboring certain mutated forms of isocitrate dehydrogenase 1 (mIDH1 or mt-IDH1).

BACKGROUND

The metabolic enzyme isocitrate dehydrogenase (IDH1) catalyzes the oxidative decarboxylation of isocitrate to $\alpha$-ketoglutarate ($\alpha$-KG). In both hematologic and solid tumor malignancies, mutated IDH1 acquires the neomorphic activity of converting $\alpha$-KG to 2-hydroxyglutarate (2-HG) and thereby leads to the aberrant accumulation of 2-HG. 2-HG has been proposed to act as an "oncometabolite" that has pleotropic effects on tumorigenesis. Excess production of 2-HG has been shown to inhibit $\alpha$-KG-dependent enzymes involved in epigenetic regulation, collagen synthesis, and cell signaling, thereby leading to a block in normal differentiation of progenitor cells and the subsequent development of cancer. Therefore, inhibition of mutated IDH1 in tumor cells and the concomitant decrease in 2-HG production is a therapeutic approach to the treatment of IDH1-mutated cancers.

IDH1 mutations reported in cancer can occur at amino acid position R132, such as R132H, R132C, R132S, R132G, and R132L mutations. There remains a need for methods of identifying patients to receive therapeutically effective amount of an IDH1 inhibitor compound that selectively inhibits production of 2-HG from cancer cells harboring a variety of R132 IDH1 mutations.

SUMMARY

Olutasidenib is a potent, selective, orally bioavailable, small-molecule inhibitor of mutated IDH1 and is useful as an anticancer therapeutic in patients with acute myeloid leukemia (AML) or myelodysplastic syndrome (MDS) with certain mutations in the IDH1 gene (including R132X mutations). Methods of administering olutasidenib for the treatment of certain hematological cancers (e.g., AML and MDS) are disclosed herein.

The present disclosure provides methods for the treatment of AML or MDS comprising a step of administering to a subject diagnosed with a cancer harboring a R132X IDH-1 mutation, a therapeutically effective amount of a pharmaceutically acceptable form of olutasidenib. In some examples, the pharmaceutically acceptable form of olutasidenib is an oral dosage form (e.g., as provided in Example 1). In some embodiments, olutasidenib is administered to the patient as R132X mIDH-1 Selective Inhibitor Therapy consisting of oral administration of an oral dosage form of olutasidenib administered either as a single agent inhibitor of mIDH-1, or in combination with azacitidine or cytarabine. When olutasidenib is administered in such combination therapy, the subject can be receiving or have previously received treatment with azacitidine or cytarabine.

Olutasidenib can be administered at a dose of 150 mg twice per day throughout the course of treatment. Olutasidenib can be administered with food to improve bioavailability of olutasidenib. The Course of Treatment can be at least 15 consecutive days starting with the initial dose of olutasidenib and longer (e.g., up to 30 weeks, 15 days to 30 weeks, 15 days to 12 weeks, at least 12 weeks, 12-30 weeks, 15 days to 6 months and other intermediate or longer durations or intervals apparent based on the present disclosure).

A patient can be identified as having a R132X mutation in mIDH1 using a diagnostic method disclosed herein prior to the administration of olutasidenib to the patient. The R132X gene mutation can be determined prior to administration of olutasidenib to the patient. Olutasidenib can be administered to patients who have received prior anticancer therapy or other concomitant (non-anticancer) medications. In some examples, olutasidenib is administered to patient who has not received a prior mIDH-1 inhibitor therapy.

BRIEF DESCRIPTION OF THE DRAWINGS

FIG. 3 also illustrates steady state is achieved by Week 2; ($t_{1/2}$ ~60 hrs) and 150 mg BID steady state exposures >$IC_{90}$ and below levels are expected to increase QTcF potential.

FIG. 4 also illustrates that plasma exposures of Compound 1 are stable throughout treatment duration in patients. This can serve as basis for selecting a 150 mg BID dose for dose expansion and a recommended phase II dose.

FIG. 13 also illustrates steady state is achieved by Week 2; ($t_{1/2}$ ~60 hrs) and 150 mg BID and 300 mg QD steady state exposures are >$C_{eff}$.

FIG. 17 also illustrates steady state is achieved by Week 2; ($t_{1/2}$ ~60 hrs) and 150 mg BID QD steady state exposures are >$C_{eff}$.

DETAILED DESCRIPTION

Definitions

Figure 1A:
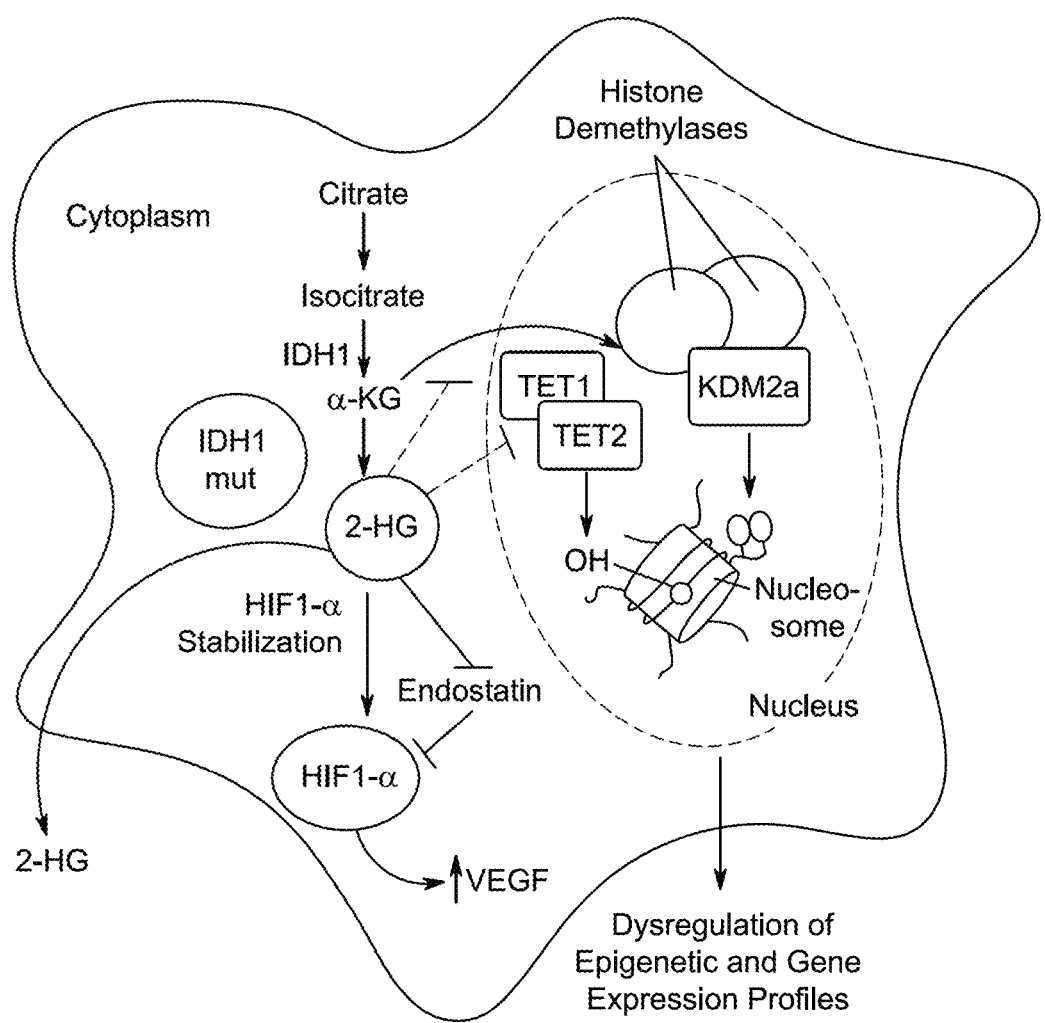
FIG. 1A and FIG. 1B are schematics of the dysregulation of epigenetic and gene expression profiles associated with IDH mutants.
Figure 1B:
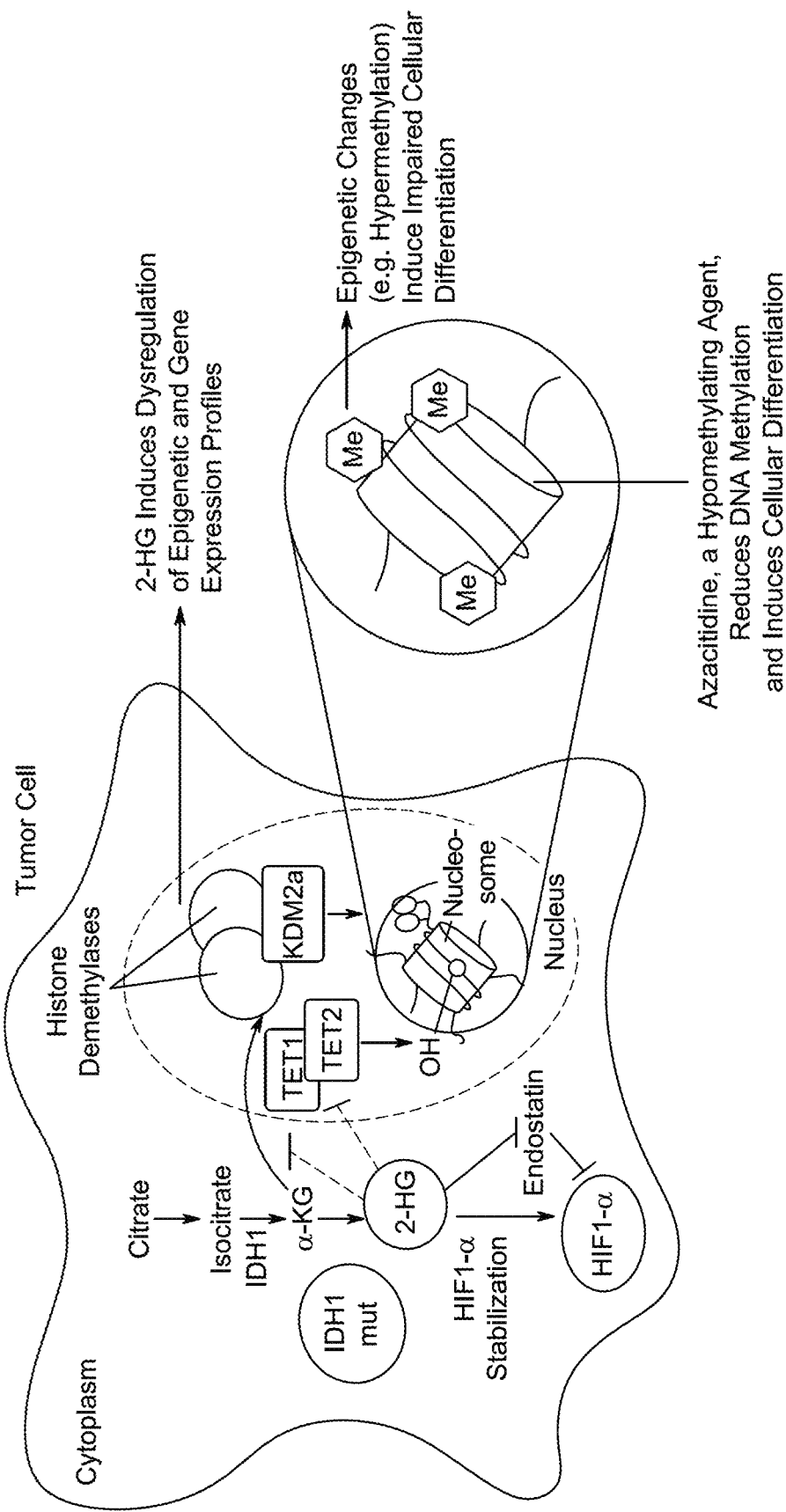
Figure 2A:
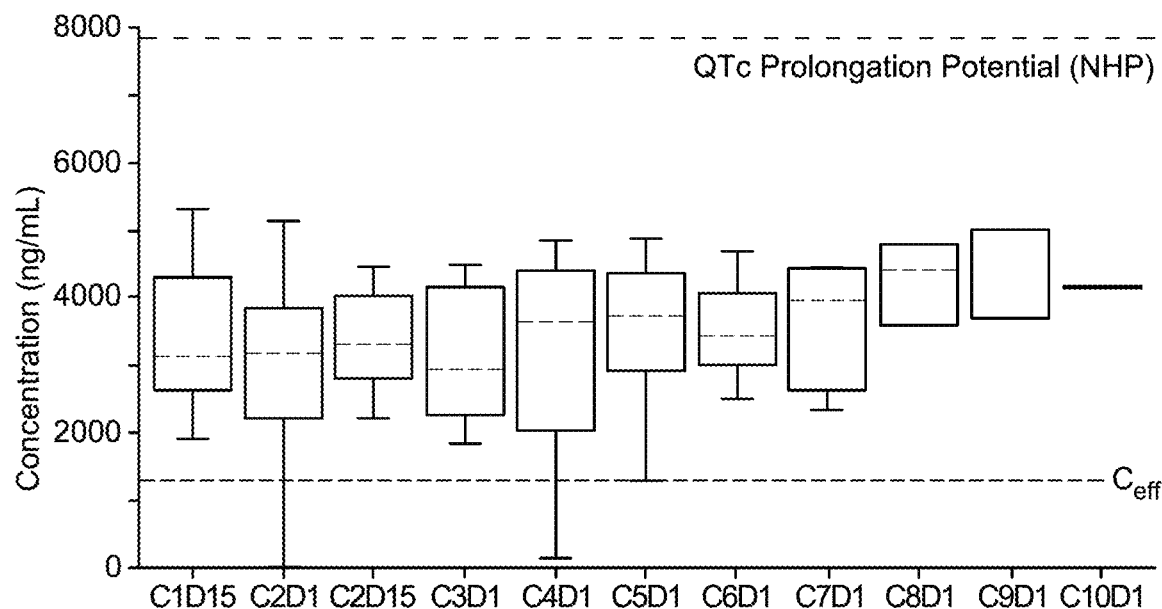
FIG. 2A is a graph of blood plasma concentration of Compound 1 (i.e., olutasidenib) measured in a group of human patients treated with Compound 1 as a single agent throughout a course of treatment. The dashed line labeled "$C_{eff}$" is lower than 1652 ng/m L.
Figure 2B:
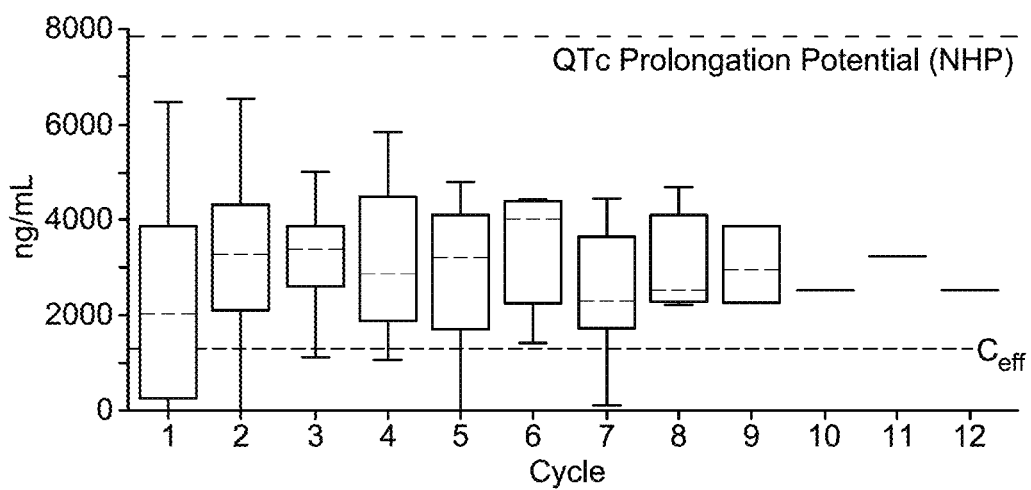
FIG. 2B is a graph of blood plasma concentration of Compound 1 measured in a group of human patients treated with Compound 1 and azacitidine throughout a course of treatment. The dashed line labeled "$C_{eff}$" is lower than 1652 ng/mL.
Figure 2C:
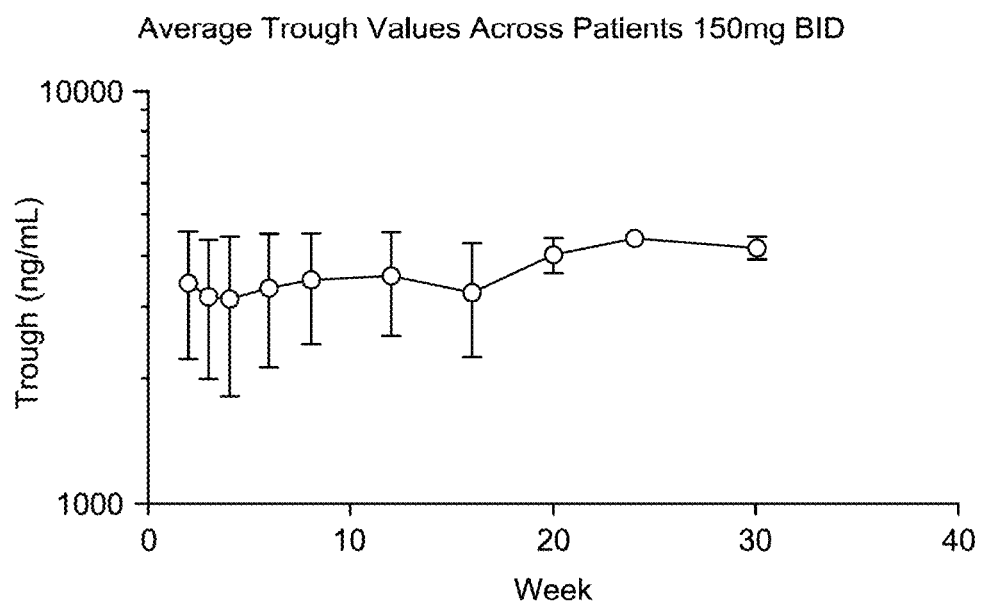
FIG. 2C is a graph of effective blood plasma concentration of Compound 1 measured in a group of human patients throughout a course of treatment.
Figure 2D:
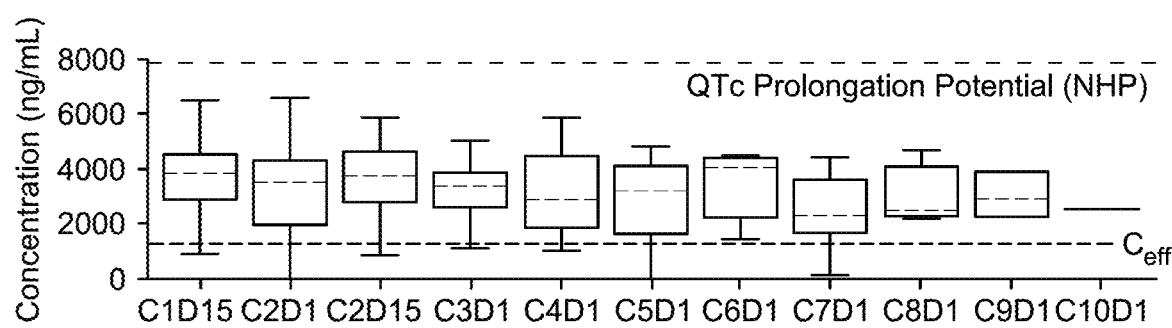
FIG. 2D is a graph of blood plasma concentration of Compound 1 measured in a group of human patients treated with Compound 1 and azacitidine throughout a course of treatment. The dashed line labeled "$C_{eff}$" is lower than 1652 ng/mL.
Figure 2E:
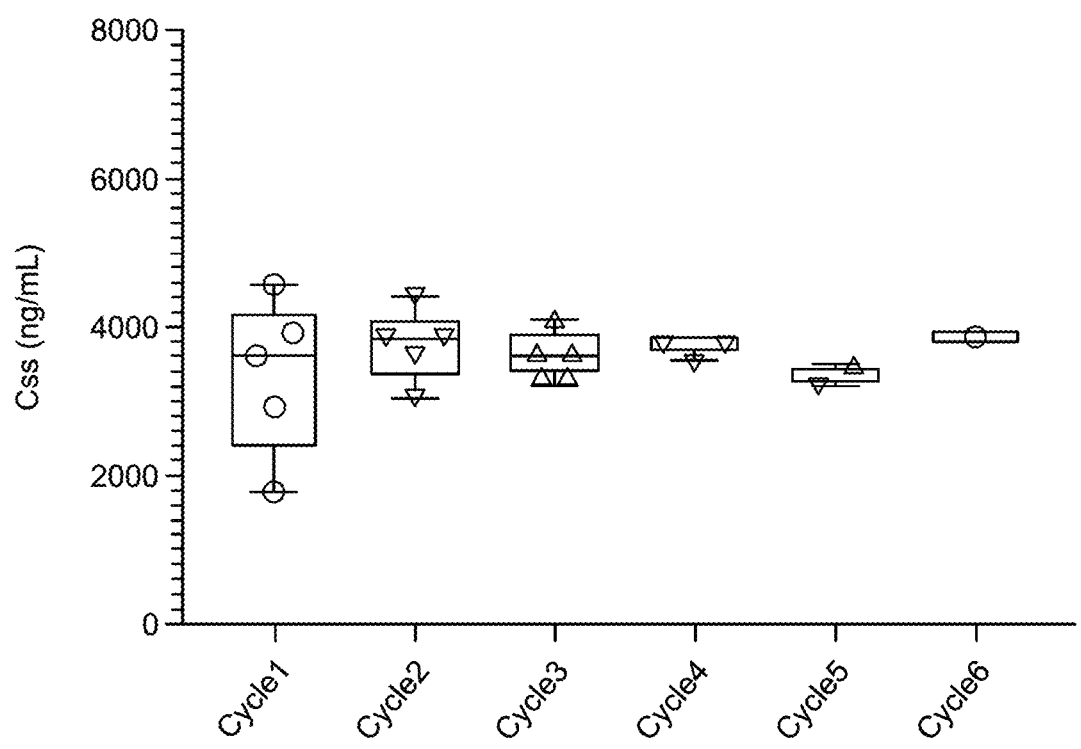
FIG. 2E is a graph of blood plasma concentration of Compound 1 measured in a group of human patients throughout a Course of Treatment.

As used herein, the term "R132X mIDH-1 mutation(s)" refers to a mutation at IDH-1 arginine 132 that results in inhibitory activity of Compound 1 against the mutated IDH-1 form harboring the R132 mutation. Preferably, the R132X mutations have a 2-HG $IC_{50}$ value of less than 500 nM (most preferably less than 250 nM or less than 150 nM) using the in vitro assay of Example 2. Accordingly, preferred R132X mutations include R132H and R132C, as well as R132L, R132G, and R132S (or other R132X mutations having therapeutically relevant 2-HG $IC_{50}$ values obtained using the in vitro assay of Example 2). Patients having R132X mIDH-1 mutation(s) can be identified using a suitable diagnostic, such as a diagnostic analyzing patient tissue with next generation sequencing technology that identified the presence of the R132X mIDH-1 mutation in the patient tissue sample.

As used herein, the term "R132X mIDH-1 Selective Inhibitor Therapy" refers to a therapy administered to a patient to inhibit the activity of R132X mIDH-1 in the patient, where the therapy is known to have selective inhibitory activity against R132X mIDH-1 over wild type IDH-1.

As used herein, the term "Course of Treatment" refers to the time period in which a patient is being administered an agent, including any administration holidays or recovery periods. A Course of Treatment can include a single treatment cycle or multiple treatment cycles. Additionally, a Course of Treatment can include a partial treatment cycle. The Course of Treatment can include the total time period during which a patient is on a treatment protocol for AML or MDS for a therapy comprising the administration of a mIDH-1 inhibitor compound.

"Next-generation sequencing" or "NGS" or "NG sequencing" as used herein, refers to any sequencing method that determines the nucleotide sequence of either individual nucleic acid molecules (e.g., in single molecule sequencing) or clonally expanded proxies for individual nucleic acid molecules in a high through-put fashion (e.g., greater than 103 or more molecules are sequenced simultaneously). Various next generation sequencing methods are known. In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) Nature Biotechnology Reviews 11:31-46, incorporated herein by reference. Next generation sequencing can detect a variant present in less than 5% of the nucleic acids in a sample.

The terms "subject" and "patient" are used interchangeably in the present disclosure.

Provided Methods

In some embodiments, the present disclosure provides methods of treating acute myeloid leukemia (AML) in patients with an isocitrate dehydrogenase-1 (IDH1) mutation, the method comprising steps of:
  a. providing DNA from a sample obtained from a patient;
  b. detecting an IDH1 mutation in the DNA from the sample; and
  c. administering to the patient with the IDH1 mutation a total of 150 mg of olutasidenib twice daily in a pharmaceutically acceptable composition.

In some embodiments, the present disclosure provides methods of treating acute myeloid leukemia (AML) in patients with an isocitrate dehydrogenase-1 (IDH1) mutation, the method comprising steps of:
  a. isolating and purifying DNA from a sample obtained from a patient;
  b. detecting an IDH1 mutation in the DNA from the sample; and
  c. administering to the patient with the IDH1 mutation a total of 150 mg of olutasidenib twice daily in a pharmaceutically acceptable composition.

In some embodiments, the present disclosure provides methods of treating AML in patients with an isocitrate dehydrogenase-1 (IDH1) mutation, the method comprising steps of:
  determining whether the patient has an IDH1 mutation by:
    i. obtaining a sample from the patient; and
    ii. performing an assay (e.g., an FDA-approved diagnostic test, such as the IDH1 Assay of Example 8) on the sample to determine if the patient has an IDH1 mutation; and
  if the patient has an IDH1 mutation, then administering to the patient with the IDH1 mutation a total of 150 mg of olutasidenib twice daily in a pharmaceutically acceptable composition, and
  if the patient does not have an IDH1 mutation, then not administering to the patient with the IDH1 mutation a total of 150 mg of olutasidenib twice daily in a pharmaceutically acceptable composition.

The present disclosure also provides methods of treating acute myeloid leukemia (AML) in patients with an isocitrate dehydrogenase-1 (IDH1) mutation, the method comprising administering twice daily to a patient with an IDH1 mutation 150 mg of olutasidenib in a pharmaceutically acceptable composition, wherein the IDH1 mutation has been detected using an FDA-approved diagnostic test.

In some embodiments, the IDH1 mutation is an IDH1 R132 mutation. Examples of an IDH1 R132 mutation include R132C, R132H, R132S, R132G, and R132L. In some embodiments, the IDH1 R132 mutation is R132C. In some embodiments, the IDH1 R132 mutation is R132H. In some embodiments, the IDH1 R132 mutation is R132S. In some embodiments, the IDH1 R132 mutation is R132G. In some embodiments, the IDH1 R132 mutation is R132L. In some embodiments, the patient is harboring an IDH1 mutation, such as an IDH1 R132 mutation selected from the group consisting of R132C, R132H, R132S, R132G, and R132L.

In some embodiments, the AML is relapsed or refractory AML.

In some embodiments, the patient is receiving or has received anticancer therapy. In some embodiments, the patient is resistant or refractory to prior anticancer therapy. In some embodiments, the patient is receiving or has received therapy comprising azacitidine or cytarabine.

Olutasidenib can be administered as provided herein. For example, olutasidenib can be administered as an oral dosage form, such as a tablet or a capsule. For example, olutasidenib can be administered as part of a combination therapy comprising, e.g., olutasidenib and azacitidine or cytarabine. For example, olutasidenib can be administered as the PRODUCT described in Example 7.

In some embodiments, provided methods further comprise not administering olutasidenib if the patient does not have an IDH1 mutation, as determined, e.g., by an FDA-approved diagnostic test.

Administration of olutasidenib in the oral dosage form described in Example 1 at 150 mg BID resulted in a sustained therapeutically effective trough blood plasma concentration above 2,000 ng/mL after cycle 3 of a 28-day treatment cycle (FIGS. 2A-2E). The steady state blood concentrations of olutasidenib measured in the patients was above the $IC_{90}$ value for 2-HG inhibition in R132X mIDH-1 cells (described in the Examples). As shown in FIGS. 2A-2E, the plasma exposures (steady state blood plasma concentration) of olutasidenib were durable (i.e., sustained) throughout the 30-week treatment duration. No dose limiting toxicities of olutasidenib were observed during dose escalation studies, and the maximum tolerated dose (MTD) of olutasidenib was not reached.

Figure 4:
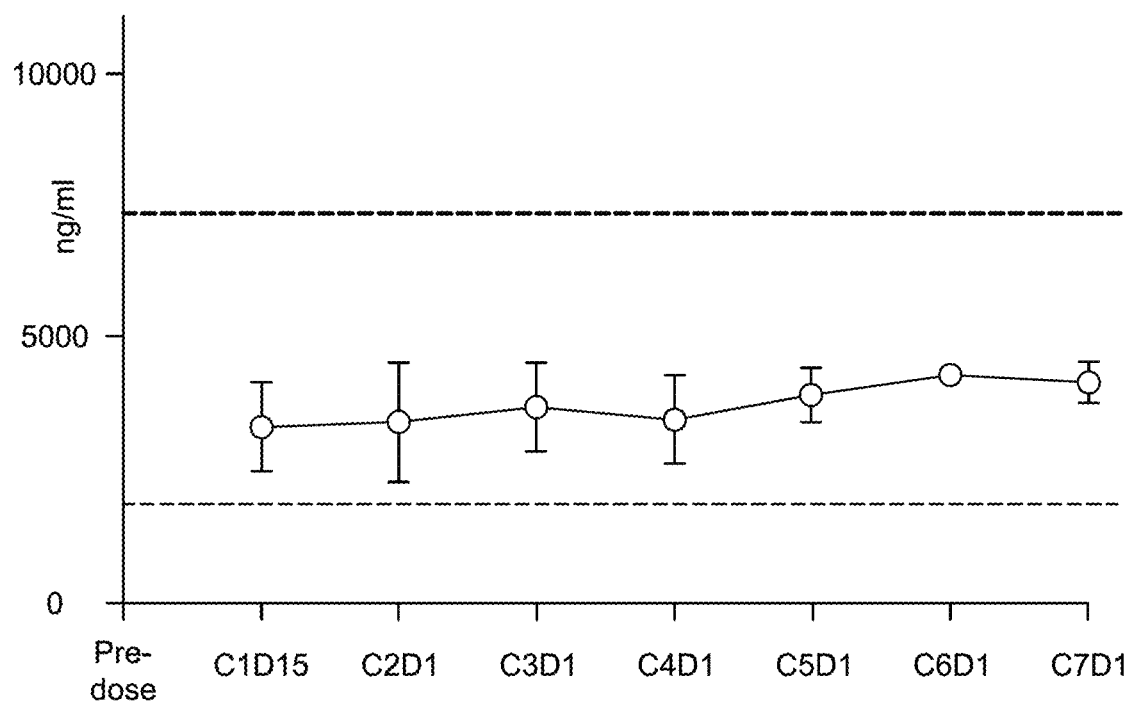
FIG. 4 is a graph $C_{SS}$ over time of patients treated with Compound 1 at 150 mg BID.

FIGS. 2A-2E are graphs of the data obtained from measuring the steady state concentrations from patients in the clinical trial receiving a 150 mg BID dose of olutasidenib, either as a single agent or in combination with azacitidine as described in Example 6. FIG. 4 is a graph showing the steady state concentration of olutasidenib measured in patients at various points during the Course of Treatment described in the clinical trial of Example 6, with each point representing a cycle number and day number (each cycle is 28 consecutive days of administration of 150 mg BID olutasidenib). The steady state concentration of olutasidenib remained above the minimum desired level (bottom dashed line) and the maximum desired level (upper dashed line).

Figure 5A:
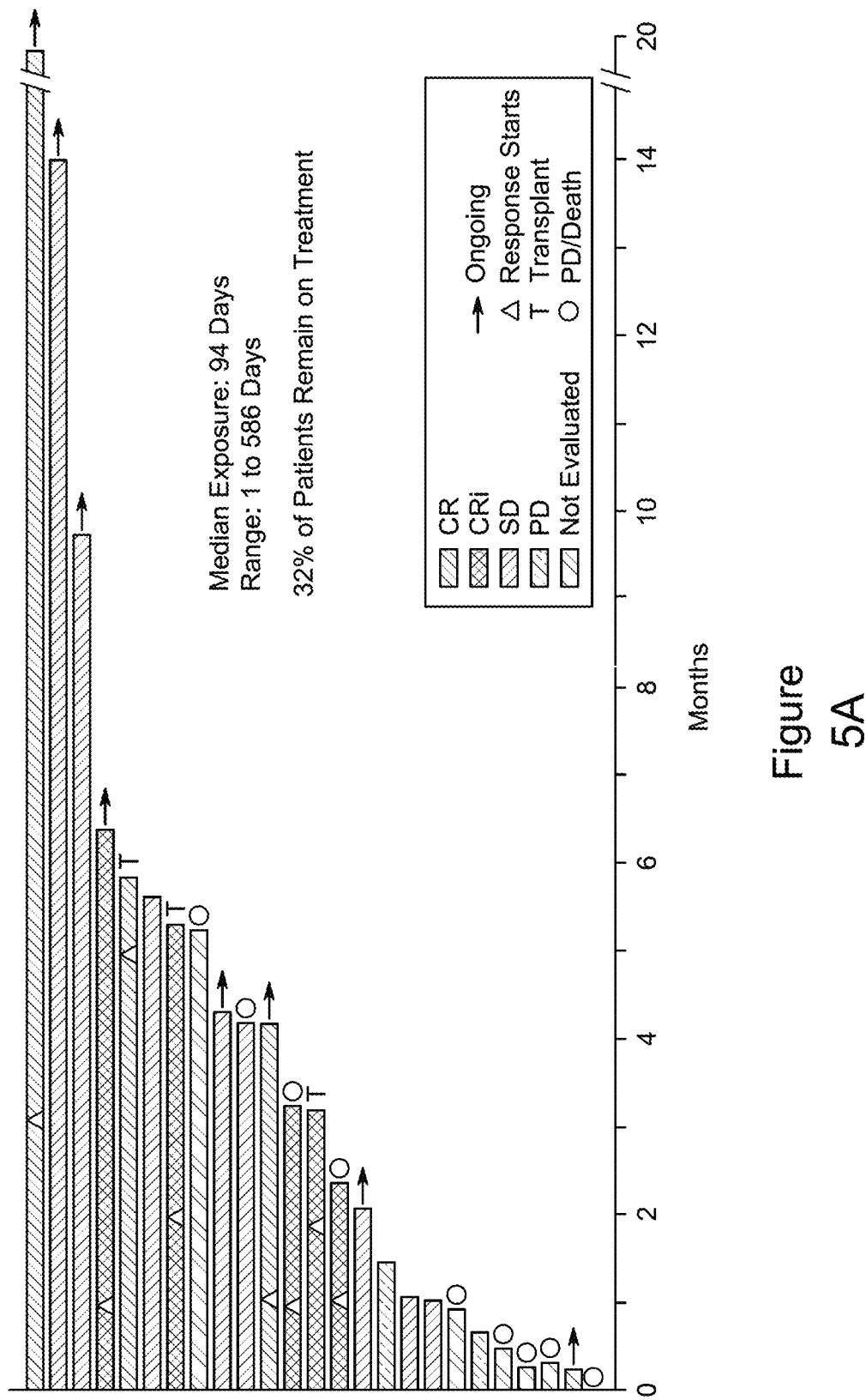
FIG. 5A, FIG. 5B, and FIG. 5C are each a graph showing time on treatment of AML patients treated with a single agent (Compound 1).
Figure 5B:
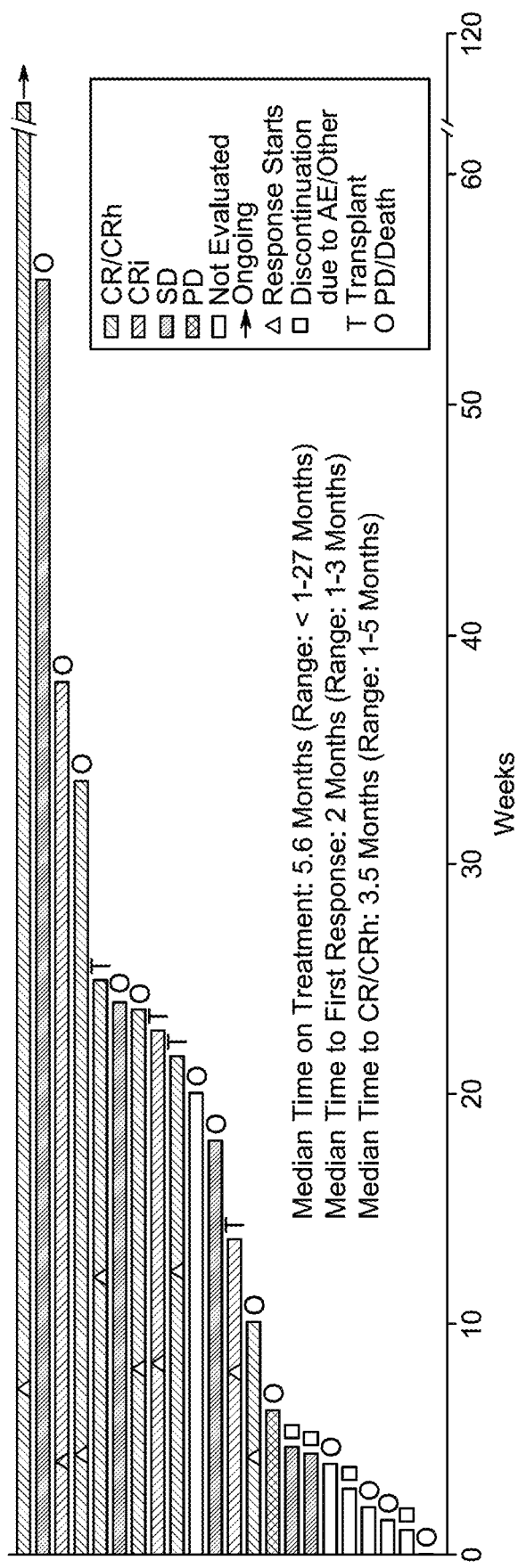
Figure 5C:
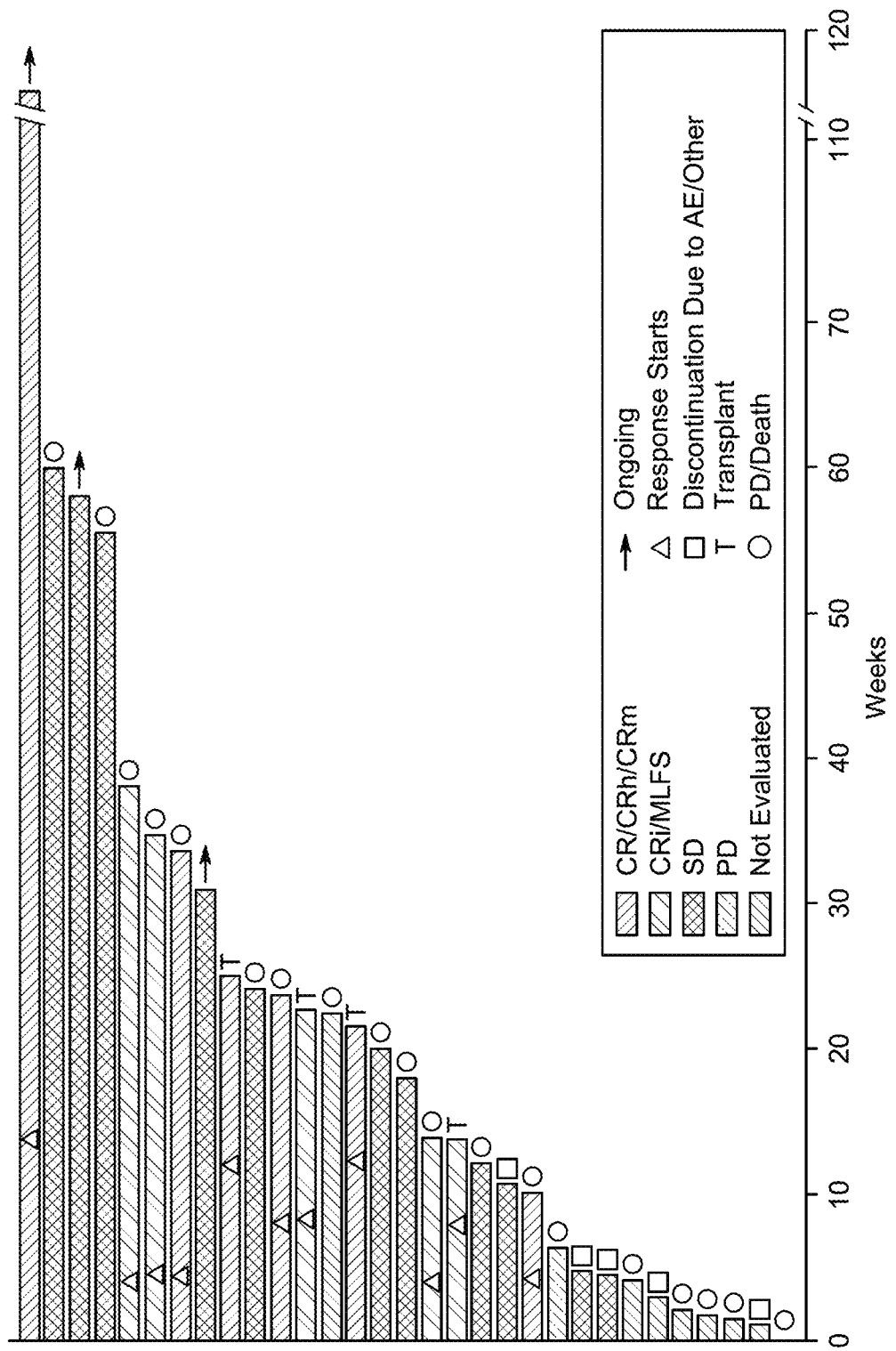

FIGS. 5A and 5C are graphs showing the results from the clinical trial in Example 6, showing the 150 mg BID administration of olutasidenib (solid form obtainable from Example 1) was administered as a single agent to multiple patients over a Course of Treatment times having a median of 94 days, and a range of 1 to 586 days. About 32% of the patients remain on treatment.

FIG. 5B depicts responses for relapsed or refractory (R/R) AML patients, and shows prolonged duration of treatment with olutasidenib was observed with a 1st response occurring within 2 months of treatment with olutasidenib. Responses<CR/CRi were noted to deepen with continued treatment resulting in CR/CRh/CRi rate of 41% in R/R AML. Clinical benefit (SD 8 weeks) was observed in subjects without an IWG defined response. 10% of patients (1 AML and 2 MDS) remained on treatment. Treatment Discontinuation: Progressive Disease (PD) (9), death (6), transplant (4), Adverse Events (AE) (3), investigator's decision (2), withdrawal of consent (1), and lack of response (3).

The invention is based in part on the discovery that administration of olutasidenib at 150 mg BID resulted in a higher blood exposure level than either 150 mg QD or 300 mg BID at day 15. See, for example, FIG. 3. Administration of olutasidenib at 150 mg QD BID resulted in a blood exposure level of <3000 ng/mL at day 15. Administration of olutasidenib at 300 mg QD BID did not result in improved blood levels at day 15. In contrast, administration of olutasidenib at 150 mg BID results in a blood exposure level of >3000 ng/mL at day 15.

Figure 3:
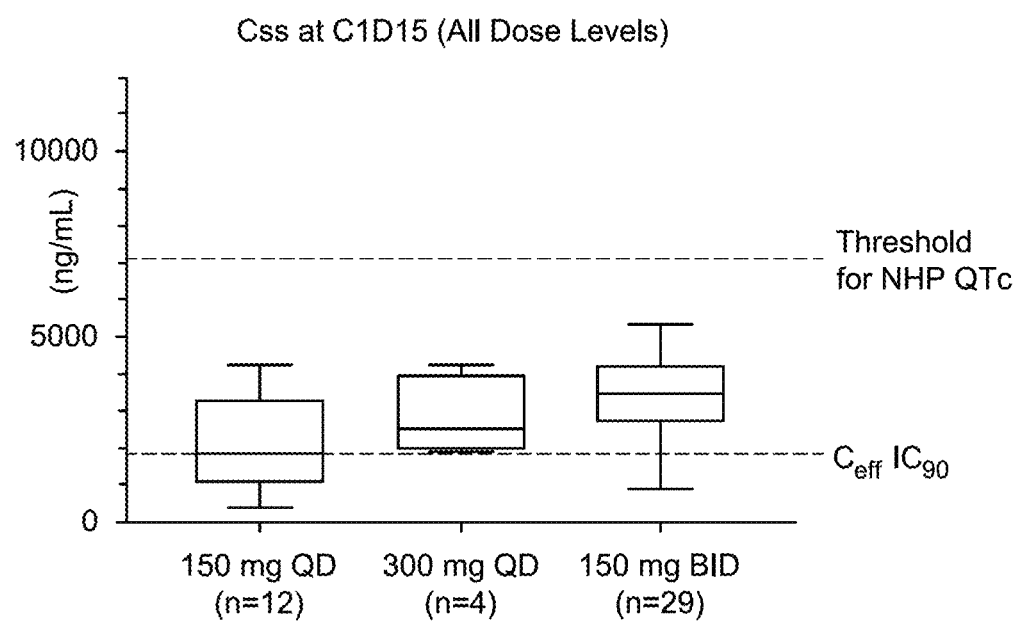
FIG. 3 is a graph showing the levels of steady-state concentration of Compound 1 measured in a group of human patients at the day 15 trough (ng/mL) of Compound 1 after administration to patients of 150 mg QD, 300 mg QD, and 150 mg BID of Compound 1.

The oral dosage form of olutasidenib (Example 1) was administered to human patients as a single agent (150 mg QD, 300 mg QD, 150 mg BID and 100 mg QD until disease progression) in a human clinical trial treating AML/MDS in cancer patients harboring a mIDH1 mutation, as described in the Examples below. FIG. 3 is a graph showing the concentration of olutasidenib measured in the blood of patients after receiving olutasidenib (as the solid form obtained from Example 1) in one of three different dose and dose intervals: 150 mg QD, 300 mg QD or 150 mg BID (either receiving olutasidenib as a single agent or in combination with azacitidine as described in the clinical trial of Example 6, in each category).

Figure 6A:
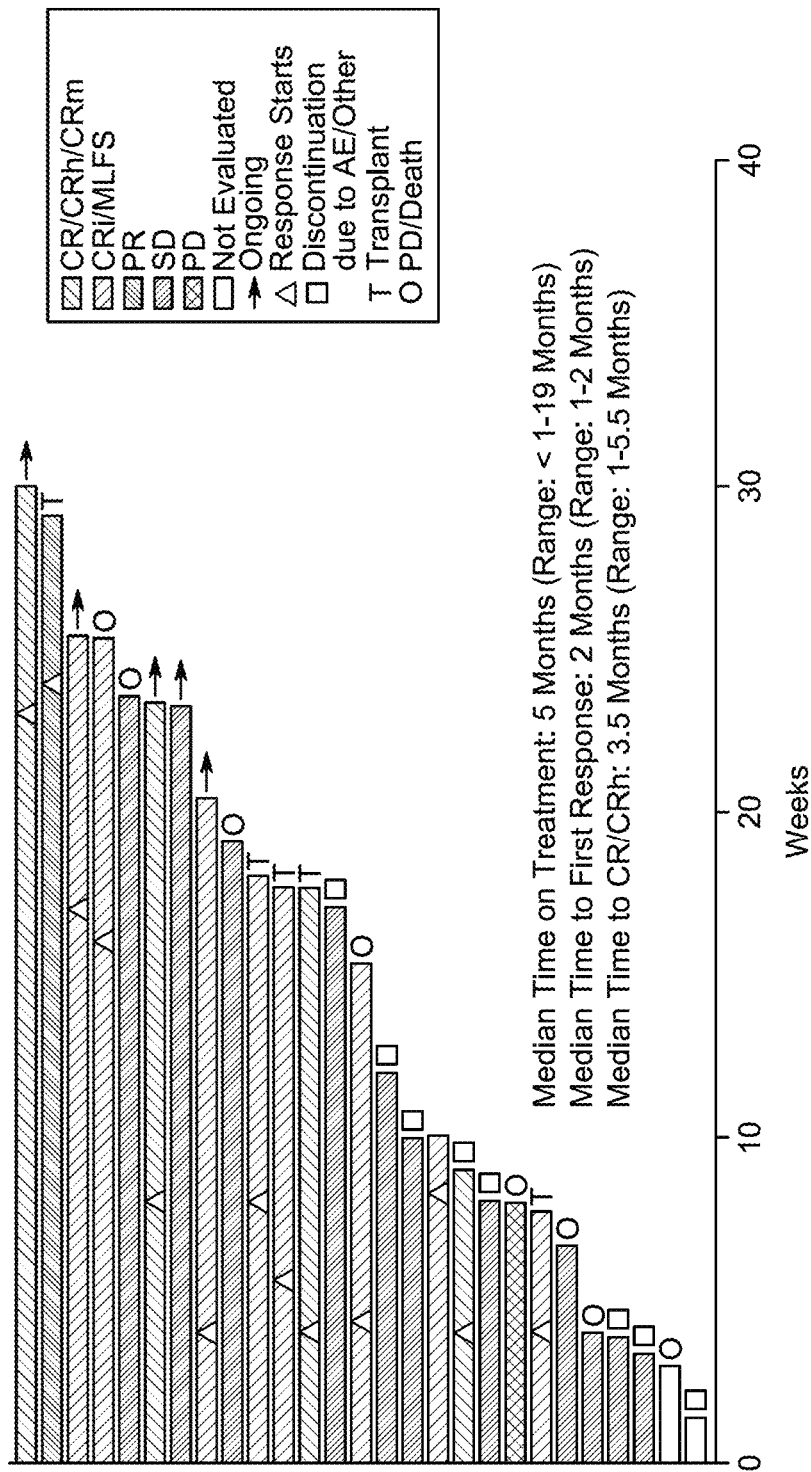
FIG. 6A and FIG. 6B are each a graph showing time on treatment of AML patients treated with a combination of Compound 1 and azacitidine.
Figure 6B:
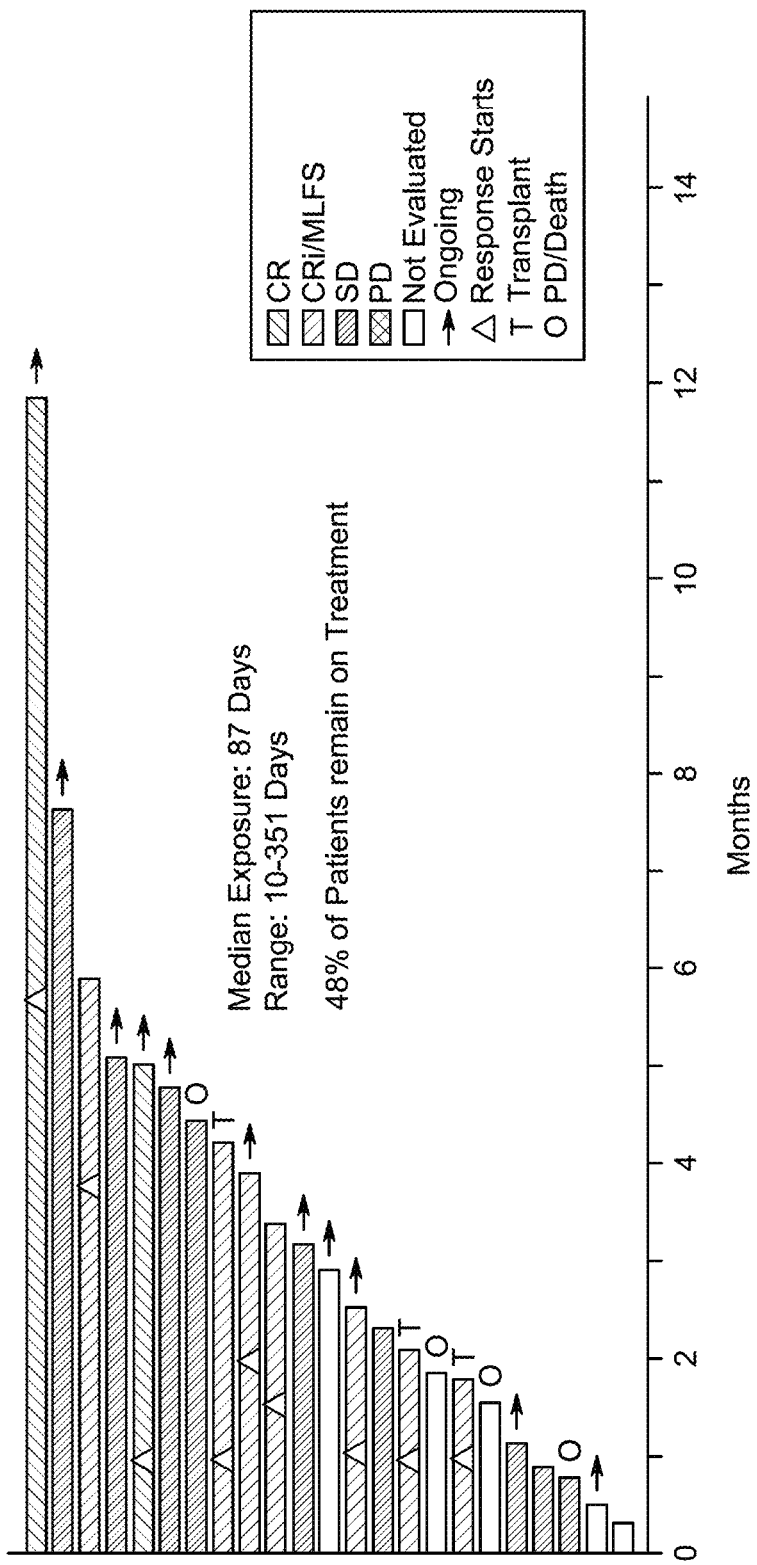

Olutasidenib can be administered to certain patients in combination with a hypomethylating agent such as azacitidine. IDH1 mutations (e.g., in AML or MDS patients harboring a R132X mIDH-1 mutation) can result in abnormal hypermethylation of histones and DNA and suppression of normal cellular differentiation. The combination of olutasidenib and azacitidine can be administered for the treatment of patients with AML harboring IDH1 mutations. For example, patients can be administered the olutasidenib daily (BID) in continuous 28-day cycles, alone or in combination with azacitidine (administered at the dose of 75 mg/m² for 7 days IV/SC per every 28-day cycle). For example, olutasidenib can be administered at a dose of 150 mg QD or 150 mg BID in combination with azacitidine (azacitidine administered per standard of care for a patient). FIG. 6B is a graph showing the results from the clinical trial in Example 6, showing the 150 mg BID administration of olutasidenib (solid form obtainable from Example 1) in combination with the administration of azacitidine (administered at the dose of 75 mg/m² for 7 days IV/SC per every 28-day cycle) were both administered to multiple patients over a Course of Treatment times having a median of 87 days, and a range of 10 to 351 days. About 48% of the patients remain on treatment.

As shown in FIG. 14A, upon further duration of treatment, clinical responses observed in R/R or TN AML and MDS: cytopenias associated with azacitidine may influence depth of IWG response. An ORR of 46% was observed for the combination of olutasidenib with azacitidine in R/R AML and an ORR of 78% was observed in TN AML (CR/CRi of 66%). Treatment Discontinuation was caused by: PD (6), transplant (6), investigator's decision (5), death (4), AE (2), and others: treatment failure, hospice, other treatment (1 each). 37% of patients (AML and MDS) remain on treatment.

In some methods, olutasidenib can be administered with cytarabine. Low dose cytarabine (LDAC) can be administered to certain AML patients (e.g., AML patients at or above about 60 years who are not candidates for intensive therapy, and harboring a R132X mIDH-1 mutation). The therapeutically effective combination of olutasidenib with LDAC can be administered to AML patients harboring IDH1 mutation. For example, patients can be administered olutasidenib daily (BID) in continuous 28-day cycles, alone or in combination with LDAC (administered at the dose of 20 mg BID SC for 10 days every 28-day cycle) until treatment discontinuation.

In some embodiments, the present disclosure additionally provides methods of treating AML or MDS in a patient harboring isocitrate dehydrogenase 1 mutations (mIDH1), which can comprise administering to a patient in need thereof a therapeutically effective amount of olutasidenib each day for at least three consecutive treatment cycles of 28 consecutive days each. The administration of the therapeutically effective amount of olutasidenib can result in the patient having a durable therapeutically effective trough blood plasma concentration of olutasidenib in the patient throughout the course of treatment.

Diagnostic Tests

In some embodiments, provided methods comprise detecting an IDH1 mutation and administering olutasidenib as described herein. In some embodiments, IDH1 mutations can be detected using an FDA-approved diagnostic test, such as the IDH1 Assay described in Example 8.

In some embodiments, detecting an IDH1 mutation comprises detecting a single nucleotide variant (SNV) coding the IDH1 mutation. In some embodiments, the IDH1 mutation is selected from the group consisting of R132C, R132H, R132G, R132S, and R132L. In some embodiments, detecting an IDH1 R132C mutation comprises detecting the SNV: TGT. In some embodiments, detecting an IDH1 R132H mutation comprises detecting the SNV: CAT. In some embodiments, detecting an IDH1 R132G mutation comprises detecting the SNV: GGT. In some embodiments, detecting an IDH1 R132S mutation comprises detecting the SNV: AGT. In some embodiments, detecting an IDH1 R132L mutation comprises detecting the SNV: CTT.

In some embodiments, the IDH1 mutation is detected using PCR technology with homogenous real-time fluorescence detection. In some embodiments, the IDH1 mutation is detected using an in vitro polymerase chain reaction (PCR) assay for the qualitative detection of single nucleotide variants (SNVs) coding an IDH1 R132 mutation selected from the group consisting of R132C, R132H, R132G, R132S, and R132L in the DNA from a sample.

In some embodiments, the diagnostic test uses a sample obtained from the patient. In some embodiments, the sample is a blood or tissue sample. In some embodiments, the sample is patient bone marrow. In some embodiments, the sample is patient blood. In some embodiments, the sample has been preserved with EDTA.

In some embodiments, provided methods further comprise:
  lysing cells from the sample at an elevated temperature in a lysis buffer comprising guanidine isothiocyanate;
  capturing DNA released from the lysed cells using magnetic microparticles;
  washing the captured DNA; and
  eluting the captured DNA from the magnetic microparticles with elution buffer to give an extracted DNA sample.

In some embodiments, provided methods further comprise:
  combining the extracted DNA sample, a DNA polymerase, oligonucleotide primers, deoxyribonucleoside triphosphates (dNTPs), and magnesium chloride in a well of a 96-well plate to give a mixture;
  sealing the 96-well plate with a cover;
  activating the DNA polymerase at a high temperature;
  subjecting the mixture to thermal cycling comprising multiple rounds of heating (e.g., to a high temperature suitable to melt double-stranded DNA) and cooling (e.g., to a low temperature suitable to promote annealing of primers to their respective targets); and
  measuring the real-time fluorescence signals of the mixture.

In some embodiments, the oligonucleotide primers are designed to specifically amplify (i) R132C and R132H mutations or (ii) R132G, R132S, and R132L mutations. In some embodiments, the oligonucleotide primers are designed to specifically amplify R132C and R132H mutations. In some embodiments, the oligonucleotide primers are designed to specifically amplify R132G, R132S, and R132L mutations. In some embodiments, two samples from the same patient are evaluated, so that one sample is mixed with oligonucleotide primers that are designed to specifically amplify R132C and R132H mutations and the other sample is mixed with oligonucleotide primers that are designed to specifically amplify R132G, R132S, and R132L mutations.

In some embodiments, the DNA polymerase is a thermophilic enzyme that has been chemically modified to render it inactive at ambient temperature.

In some embodiments, provided methods comprise an internal control. For example, in some embodiments, the mixture further comprises oligonucleotide primers designed to amplify a region of the IDH1 gene outside of codon 132, thereby serving as an endogenous internal control.

In some embodiments, the real-time fluorescence signal of each IDH1 mutation of either (i) R132C and R132H or (ii) R132G, R132S, and R132L is distinguishable in a single well. In some embodiments, the real-time fluorescence signal of the internal control and each IDH1 mutation of either (i) R132C and R132H or (ii) R132G, R132S, and R132L is distinguishable in a single well.

Without wishing to be bound by any particular theory, it may be desirable for a diagnostic test described herein to be performed in such a way as to prevent nucleic acid contamination. In some embodiments, the diagnostic test is performed in a sealed 96-well plate. In some embodiments, the diagnostic test is performed without opening the sealed 96-well plate. In some embodiments, aerosol barrier pipette tips are used for all pipetting in provided methods. In some embodiments, the diagnostic test is performed in a dedicated area.

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein.

EXAMPLES

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). High performance liquid chromatograph (HPLC) analyses were obtained using a XBridge Phenyl or C18 column (5 μm, 50×4.6 mm, 150×4.6 mm or 250×4.6 mm) with UV detection (Waters 996 PDA) at 254 nm or 223 nm using a standard solvent gradient program (Methods 1-2).

LCMS Method 1 (ESI, 4 Min Method):
Instruments:

| HPLC: Waters HT2790 Alliance | MS: Waters ZQ Single Quad Mass Spectrometer |
|---|---|
| UV: Waters 996 PDA | |

Conditions:

| | |
|---|---|
| Mobile phase A | 95% water/5% methanol with 0.1% Formic Acid |
| Mobile phase B (B) | 95% methanol/5% water with 0.1% Formic Acid |
| Column | XBridge Phenyl or C18, 5 μm 4.6 × 50 mm |
| Column temperature | Ambient |
| LC gradient | Linear 5-95% B in 2.5 min, hold 95% B to 3.5 min |
| LC Flow rate | 3 mL/min |
| UV wavelength | 220 nm and 254 nm |
| Ionization Mode | Electrospray Ionization; positive/negative |

LCMS method 2: (APCI, 20 min):

Instruments and conditions:

HPLC-Agilent 1100 series.

Column: Agela Technologies Durashell C18, 3 μm, 4.6×50 mm).

Mobile Phase A: acetonitrile+0.1% trifluoroacetic acid.

Mobile Phase B: Water+0.1% trifluoroacetic acid.

|  | Time (min) | % B |
|---|---|---|
| Gradient: | 00 | 95 |
|  | 15 | 05 |
|  | 18 | 05 |
|  | 20 | 95 |

Flow Rate: 1 mL/min.

Column Temperature: Ambient.

Detector: 254 nm.

Example 1

Synthesis of (S)-5-((1-(6-chloro-2-oxo-1,2-dihydroquinolin-3-yl)ethyl)amino)-1-methyl-6-oxo-1,6-dihydropyridine-2-carbonitrile (Compound 1)

Figure 7:
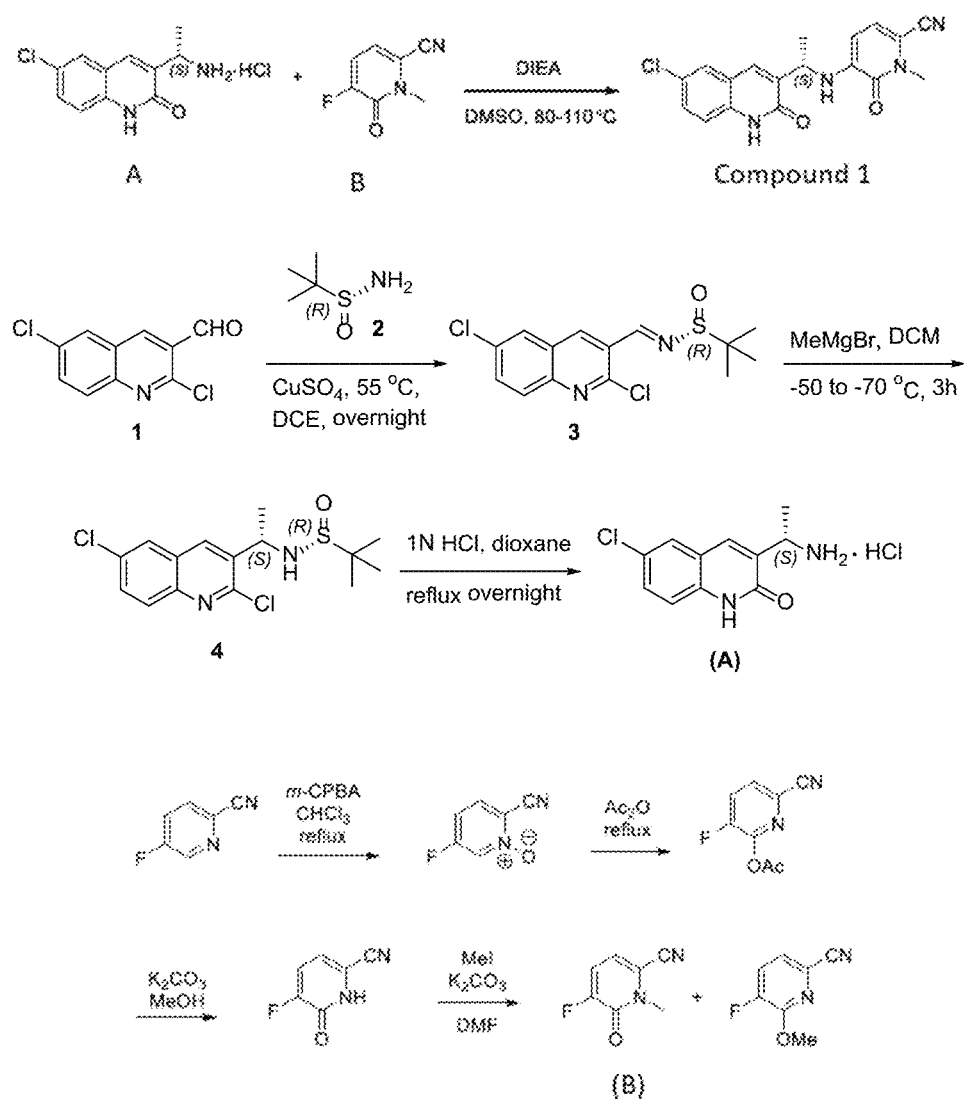
FIG. 7 is a synthetic reaction scheme for the preparation of Compound 1.

Compound 1 can be prepared in a convergent synthesis from Intermediate A and Intermediate B as shown in FIG. 7 via a nucleophilic displacement reaction under basic conditions of (S)-3-(1-aminoethyl)-6-chloroquinolin-2(1H)-one (Intermediate A) and the fluoropyridone (Intermediate B). $^1$H, $^{13}$C NMR and mass spectral data are consistent with the assigned structure. Compound 1 (5-{[(1S)-1-(6-chloro-2-oxo-1,2-dihydroquinolin-3-yl)ethyl]amino}-1-methyl-6-oxo-1,6-dihydropyridine-2-carbonitrile) has a molecular weight of 355 with a melting point onset temperature of 251.3° C. (DSC) and peak maximum 254.1° C.

The asymmetric synthesis of Intermediate A started with the condensation of the commercially available quinoline aldehyde (1) with (R)-tert-butanesulfinamide (2) to form the chiral (R)—N-tert-butanesulfinimine (3), followed by addition of methyl magnesium bromide in dichloromethane to yield the desired product (4) as the major diastereoisomer (dr: 98:2). Cleavage of the chiral auxiliary and simultaneous hydrolysis of 2-chloroquinoline moiety under mildly acidic conditions using 1N HCl in dioxane gave Intermediate A in quantitative yield. The structure of Intermediate A was confirmed by NMR and mass spectroscopy, and the enantiomeric purity was determined by chiral SFC analysis. The (S)-stereochemistry was confirmed by X-ray co-crystal structures of several inhibitor analogs prepared from the same chiral amine intermediate bound to mIDH-1 R132H.

Intermediate (B) was prepared from commercially available 5-fluoropicolinonitrile in four steps. N-oxidation of 5-fluoropicolinonitrile followed by reflux of the N-oxide in acetic anhydride gave the acetate, following work-up and purification. Solvolysis of the acetate group followed by N-methylation under standard conditions gave a mixture of N-methylated and O-methylated products (4:1). The minor O-methylated product was removed by column chromatography. NMR and mass spectral data are consistent with the structure of Intermediate Compound (B).

Intermediate 1: (S)-3-(1-aminoethyl)-6-chloroquinolin-2(1H)-one hydrochloride (A)

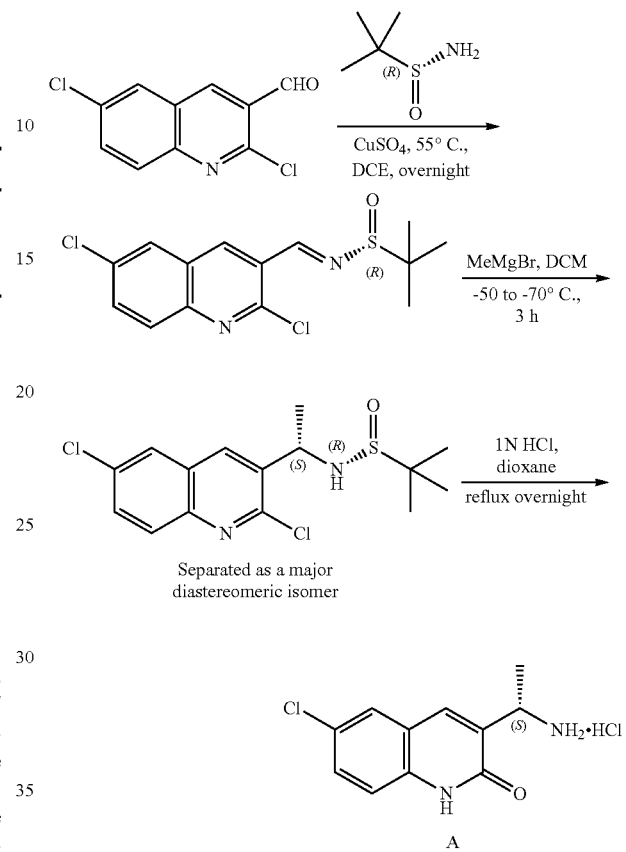

Separated as a major diastereomeric isomer

Step-1: (R,E)-N-((2,6-dichloroquinolin-3-yl)methylene)-2-methylpropane-2-sulfinamide

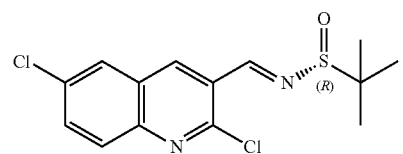

To a mixture of 2,6-dichloroquinoline-3-carbaldehyde (15.0 g, 66.37 mmol) and (R)-2-methylpropane-2-sulfinamide (8.85 g, 73.14 mmol) in 1,2-dichloroethane (150 mL) was added $CuSO_4$ (16.0 g, 100.25 mmol). The resulting mixture was heated to 55° C. and stirred at 55° C. overnight. After TLC and MS showed complete disappearance of starting materials, the mixture was cooled to room temperature and filtered through a pad of Celite®. The pad of Celite® was then rinsed with $CH_2Cl_2$. The filtrate was evaporated to dryness in vacuo and purified by $SiO_2$ column chromatography (0 to 25% hexanes/EtOAc) to afford the title compound, (R,E)-N-((2,6-dichloroquinolin-3-yl)methylene)-2-methylpropane-2-sulfinamide, as a yellow solid (17.7 g, 81% yield).

Step-2: (R)—N—((S)-1-(2,6-dichloroquinolin-3-yl)ethyl)-2-methylpropane-2-sulfinamide

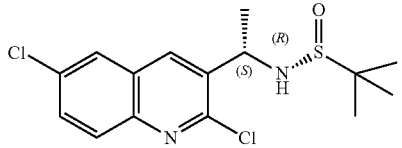

To a solution of (R,E)-N-((2,6-dichloroquinolin-3-yl)methylene)-2-methylpropane-2-sulfinamide (8.85 g, 26.88 mmol) in anhydrous $CH_2Cl_2$ (200 mL) at −60° C. was added dropwise MeMgBr (3M solution in diethyl ether, 13.5 mL, 40.54 mmol). The resulting reaction mixture was stirred at about −60 to −50° C. for 3 hours and then stirred at −20° C. overnight under an atmosphere of $N_2$. After TLC and MS showed complete disappearance of starting materials, saturated $NH_4Cl$ (163 mL) was added at −20° C. and the resulting mixture was stirred for 10 minutes. The aqueous phase was extracted with $CH_2Cl_2$ (100 mL×3), dried over anhydrous $Na_2SO_4$, filtered, and evaporated. The residue was purified by column chromatography on an ISCO® chromatography system ($SiO_2$: Gold column; gradient; hexanes to 100% EtOAc) to provide the title compound, (R)—N—((S)-1-(2,6-dichloroquinolin-3-yl)ethyl)-2-methylpropane-2-sulfinamide, as a yellow solid (5.8 g, 63% yield).

Step-3: (S)-3-(1-aminoethyl)-6-chloroquinolin-2(1H)-one hydrochloride (A)

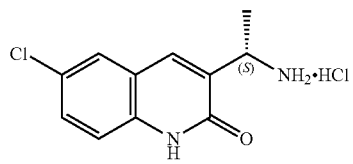

A mixture of (R)—N—((S)-1-(2,6-dichloroquinolin-3-yl)ethyl)-2-methylpropane-2-sulfinamide (6.6 g, 19.13 mmol) in 1,4-dioxane (41 mL) and 1N HCl (41 mL) was heated at reflux overnight. The solvents were evaporated in vacuo and the resulting residue was dissolved in hot water and lyophilized. The crude product was triturated with diethyl ether to afford the title compound A as a yellow solid (9.0 g, ee: 98.4%). $^1$H NMR (300 MHz, DMSO-$d_6$): δ ppm 12.4 (br s, 1H), 8.32 (br s, 2H), 8.07 (s, 1H), 7.85 (d, J=2.2 Hz, 1H), 7.63 (dd, J1=8.8 Hz, J2=2.5 Hz, 1H), 7.40 (d, J=8.8 Hz, 1H), 4.40-4.45 (m, 1H), 1.53(d, J=8.5 Hz, 3H). LCMS (Method 2): Rt 3.42 min, m/z 223.1 [M+H]$^+$.

Intermediate 2: 5-fluoro-1-methyl-6-oxo-1,6-dihydropyridine-2-carbonitrile (B)

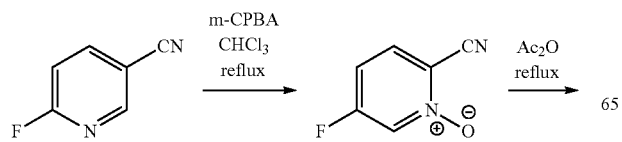

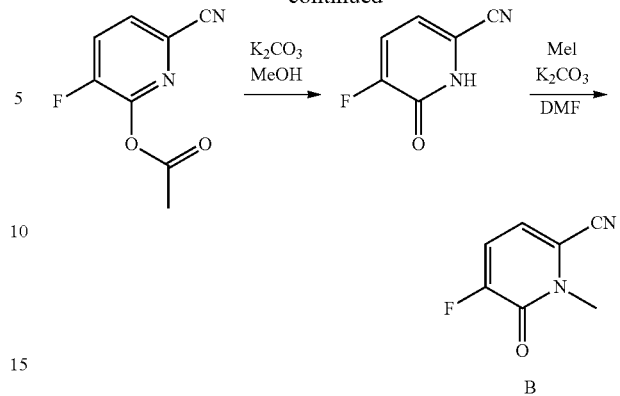

Step-1: 2-cyano-5-fluoropyridine 1-oxide

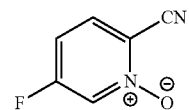

A solution of 5-fluoropicolinonitrile (7.27 g, 59.5 mmol) in $CHCl_3$ (60 mL) was added dropwise by addition funnel to a solution of m-CPBA (<77%, 22.00 g, 98 mmol) in $CHCl_3$ 160 mL). The solution was stirred at reflux for 4 days, at which time LCMS showed ~85% conversion. The sample was allowed to cool, then sodium sulfite (12.4 g, 98 mmol) was added and the sample was stirred at room temperature for three hours, during which time the solution became thick with a white precipitate. The sample was diluted with DCM (300 mL) and filtered on a Buchner funnel, and the filter cake was washed with DCM (~400 mL). A white material precipitated in the filtrate. The filtrate mixture was washed with saturated aqueous $NaHCO_3$ (400 mL), during which the solids went into solution. The organic layer was washed with water (300 mL), then dried ($MgSO_4$) and filtered. Silica gel was added and the mixture was evaporated under reduced pressure. The material was chromatographed by Biotage MPLC (340 g silica gel column) with 0 to 100% EtOAc in hexanes, with isocratic elution when peaks came off to provide 2-cyano-5-fluoropyridine 1-oxide (4.28 g, 31.0 mmol, 52% yield) as a white solid. $^1$H NMR (300 MHz, DMSO-$d_6$): δ ppm 8.85-8.93 (m, 1H), 8.23 (dd, J=9.09, 6.74 Hz, 1H), 7.53-7.64 (m, 1H). LCMS (Method 1): Rt 0.57 min., m/z 138.9 [M+H]$^+$.

Step 2: 6-cyano-3-fluoropyridin-2-yl acetate

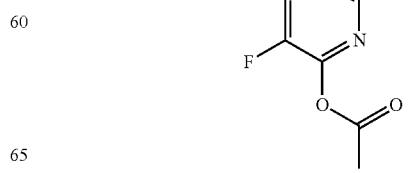

A solution of 2-cyano-5-fluoropyridine 1-oxide (4.28 g, 31.0 mmol) in acetic anhydride (40 ml, 424 mmol) was heated at reflux (150° C. bath) three days, during which the clear solution turned dark. The sample was concentrated under reduced pressure. The residue was dissolved in MeOH (30 mL) and stirred 1 hour. Silica gel was added and the solvent was evaporated under reduced pressure. The material was chromatographed by Biotage MPLC (100 g silica gel column) with 0 to 23% EtOAc in hexanes to provide 6-cyano-3-fluoropyridin-2-yl acetate (3.32 g, 18.43 mmol, 60% yield) as a clear liquid that solidified on cooling. $^1$H NMR (300 MHz, CHLOROFORM-d): δ ppm 7.65-7.75 (m, 2H), 2.42 (s, 3H). LCMS (Method 1): Rt 1.54 min., m/z 138.8 (loss of acetate).

Step 3:
5-fluoro-6-oxo-1,6-dihydropyridine-2-carbonitrile

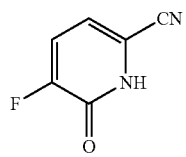

A solution of 6-cyano-3-fluoropyridin-2-yl acetate (3.32 g, 18.43 mmol) in MeOH (40 ml) was treated with potassium carbonate (5.10 g, 36.9 mmol) and stirred at room temperature for four hours. LCMS at 2 hours showed the reaction had gone to completion. The solvent was evaporated under reduced pressure. The residue was dissolved in water (100 mL) and acidified to pH ≤1 with 1M HCl. The solution was extracted with EtOAc (3×100 mL). The combined organic extracts were dried (Na$_2$SO$_4$), filtered, and evaporated under reduced pressure to provide 5-fluoro-6-oxo-1,6-dihydropyridine-2-carbonitrile (2.34 g, 16.94 mmol, 92% yield) as a white solid. $^1$H NMR (300 MHz, DMSO-d$_6$): δ ppm 12.92 (br s, 1H), 7.73 (br s, 1H), 7.43 (br s, 1H). LCMS (Method 1): Rt 0.70 min., m/z 138.9 [M+H]$^+$.

Step 4: 5-fluoro-1-methyl-6-oxo-1,6-dihydropyridine-2-carbonitrile (B)

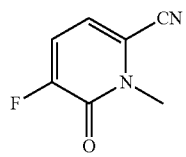

A mixture of 5-fluoro-6-oxo-1,6-dihydropyridine-2-carbonitrile (2.31 g, 16.73 mmol) and potassium carbonate (4.86 g, 35.2 mmol) in a 200 mL round bottom flask was treated with DMF (46 mL) and stirred 15 minutes. MeI (1.2 mL, 19.19 mmol) was added and the mixture was stirred at room temperature 45 minutes. The solvent was evaporated under reduced pressure. The residue was mixed with water (150 mL) and extracted with DCM (2×150 mL). The combined organic extracts were dried (MgSO$_4$), filtered, treated with silica gel, and evaporated under reduced pressure, then evaporated further at 60° C. under high vacuum. The material was chromatographed by Biotage MPLC with 0 to 35% EtOAc in hexanes, with isocratic elution at 16% EtOAc and 35% EtOAc while peaks came off. The peak that came off with 16% EtOAc was O-methylated material and was discarded. The peak that came off with 35% EtOAc provided the title compound B (1.70 g, 11.17 mmol, 67% yield) as a solid. $^1$H NMR (300 MHz, DMSO-d$_6$): δ ppm 7.53 (dd, J=9.38, 7.62 Hz, 1H), 7.18 (dd, J=7.77, 4.84 Hz, 1H), 3.60 (s, 3H). LCMS (Method 1): Rt 0.94 min., m/z 152.9 [M+H]$^+$.

Step 5: (S)-5-((1-(6-chloro-2-oxo-1,2-dihydroquinolin-3-yl)ethyl)amino)-1-methyl-6-oxo-1,6-dihydropyridine-2-carbonitrile (Compound 1)

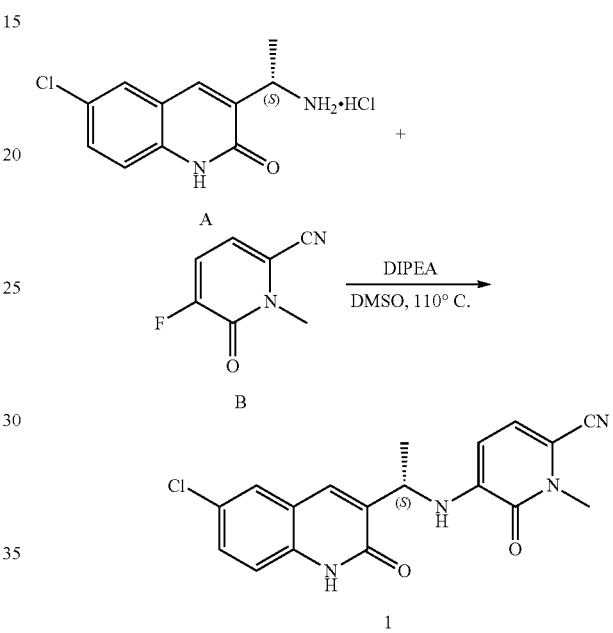

A mixture of 5-fluoro-1-methyl-6-oxo-1,6-dihydropyridine-2-carbonitrile B (1.23 g, 8.09 mmol), (S)-3-(1-aminoethyl)-6-chloroquinolin-2(1H)-one hydrochloride A (1.91 g, 7.37 mmol) and N,N-diisopropylethylamine (3.8 mL, 21.8 mmol) in anhydrous dimethyl sulfoxide (57 mL) under N$_2$ was heated to 110° C. and stirred for 6 hours. After cooling to room temperature, the mixture was partitioned between EtOAc/H$_2$O (750 mL/750 mL). The organic layer was separated, dried (Na$_2$SO$_4$) and concentrated in vacuum. The residue was purified on ISCO twice (40 g silica gel column, EtOAc/hexanes 0-100%; 80 g silica gel column, MeOH/dichloromethane 0-5%). The colorless fractions were combined and dichloromethane was removed under reduced pressure on rotavap until a lot of white solid precipitated out. The white solid was collected by filtration and washed with cold MeOH. It was then mixed with MeCN/H$_2$O (10 mL/25 mL) and lyophilized to afford the title Compound 1 as a white solid (790 mg). m.p. 262-264° C. $^1$H NMR (300 MHz, DMSO-d$_6$) δ: 12.07 (s, 1H), 7.75 (s, 1H), 7.73 (d, J=2.2 Hz, 1H), 7.51 (dd, J=8.6, 2.3 Hz, 1H), 7.31 (d, J=8.8 Hz, 1H), 6.97 (d, J=8.0 Hz, 1H), 6.93 (d, J=7.7 Hz, 1H), 5.95 (d, J=8.0 Hz, 1H), 4.68 (m, 1H), 3.58 (s, 3H), 1.50 (d, J=6.6 Hz, 3H). LCMS (Method 2): 100% pure @ 254 nm, Rt 10.78 min, m/z 355, 357 [M+H]$^+$. The filtrate and the colored fractions (TLC pure) from the second ISCO were combined and treated with activated charcoal and filtered (until the filtrate was colorless). The filtrate was then concentrated under reduced pressure on rotavap to remove dichloromethane until a lot of white solid precipitated out. The white solid was collected by filtration and washed with cold MeOH. It was then mixed with MeCN/H$_2$O (10 mL/25 mL) and lyophilized to afford the title Compound 1 as a white solid (970 mg). m.p. 262-264° C. $^1$H NMR (300 MHz, DMSO-d$_6$) δ: 12.06 (s, 1H), 7.75 (s, 1H), 7.73 (d, J=2.5 Hz, 1H), 7.51 (dd, J=8.6, 2.3 Hz, 1H), 7.31 (d, J=8.8 Hz, 1H), 6.97 (d, J=8.0 Hz, 1H), 6.92 (d, J=8.0 Hz, 1H), 5.95 (d, J=8.0 Hz, 1H), 4.68 (m, 1H), 3.58 (s, 3H), 1.50 (d, J=6.9 Hz, 3H). LCMS (Method 2): 100% pure @ 254 nm, m/z 355, 357 [M+H]$^+$. The total yield for combined two batches is 67%.

Compound 1 is also known as olutasidenib (see Example 7).

Step 6: Solid form of (S)-5-((1-(6-chloro-2-oxo-1,2-dihydroquinolin-3-yl)ethyl)amino)-1-methyl-6-oxo-1,6-dihydropyridine-2-carbonitrile (Compound 1)

Unless otherwise indicated, the clinical trial in Example 6 was performed using a pharmaceutically acceptable solid form of Compound 1 in an oral dosage form that can be obtained by the method of Step 6 of Example 1. All volumes are with respect to the quantity of Compound 1 (v/w). Compound 1 is dissolved in 18 volumes of dichloromethane. The resulting solution is then concentrated under reduced pressure to approximately 5 volumes. To the mixture is added 5 volumes of ethyl acetate. The mixture is concentrated under reduced pressure to 5 volumes. To the mixture is added an additional 5 volumes of ethyl acetate, and the mixture again concentrated under reduced pressure to 5 volumes. The mixture is diluted to 10 volumes with ethyl acetate, and the mixture stirred at room temperature for 18 hours and then cooled to 0° C. The mixture is stirred at 0° C. for 3 hours and then filtered. The solids are rinsed with ethyl acetate and dried under vacuum (counterbalanced by nitrogen) at ambient temperature.

Figure 8:
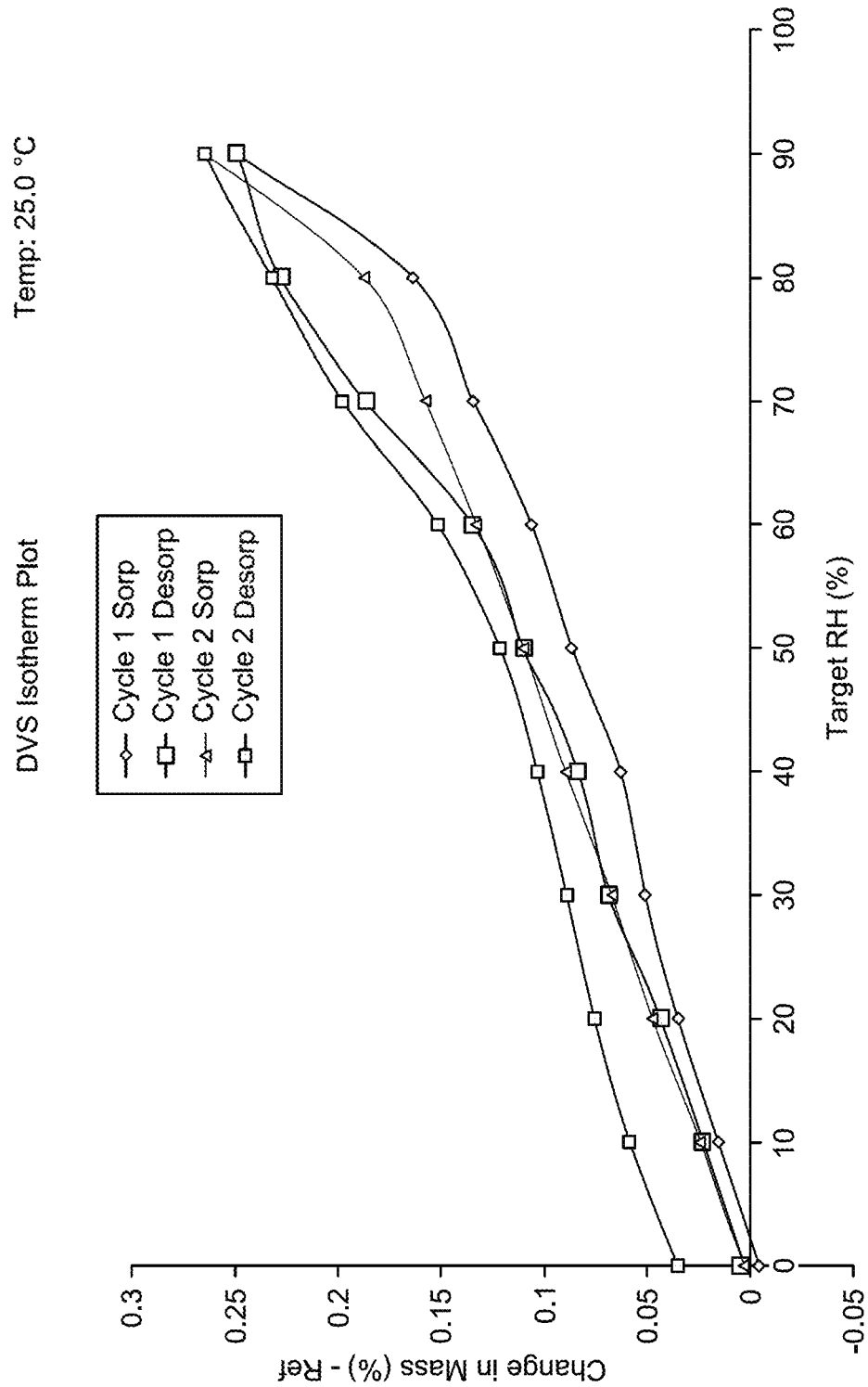
FIG. 8 depicts a dynamic vapor sorption (DVS) isotherm plot of Compound 1 Type A solid form.
Figure 9:
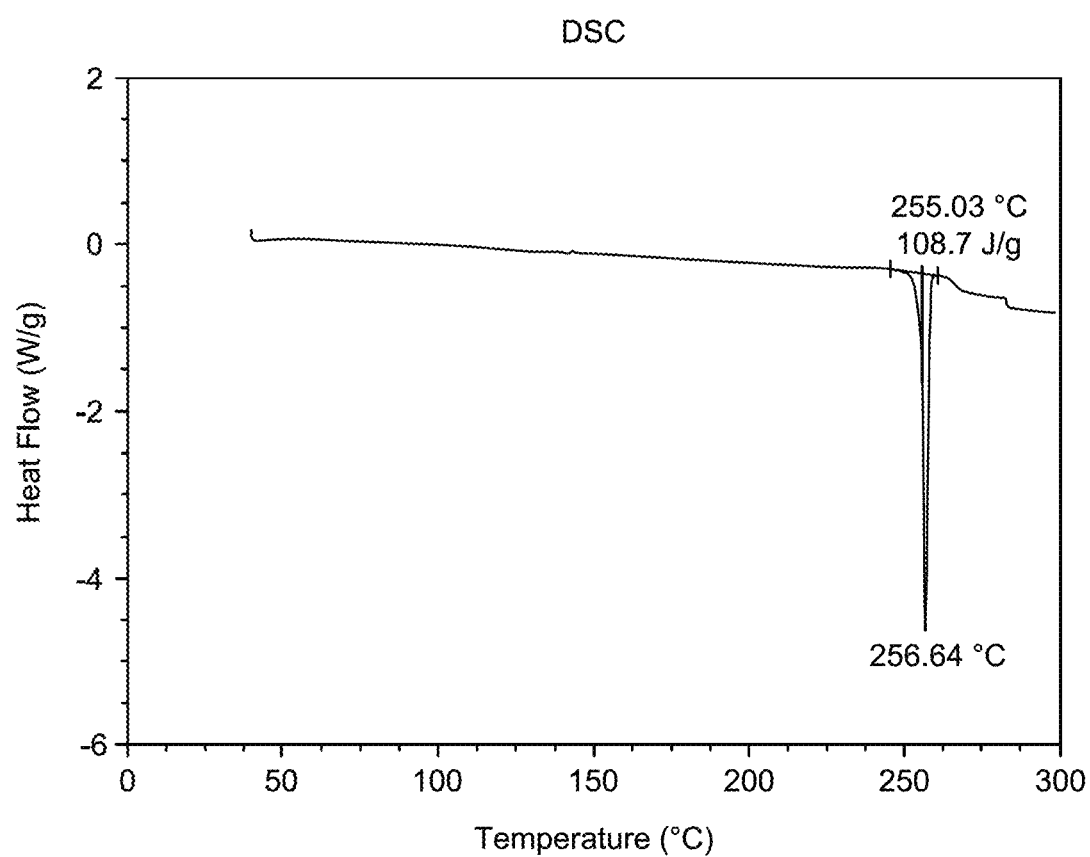
FIG. 9 depicts a differential scanning calorimetry (DSC) thermogram for Compound 1 Type A solid form.
Figure 10:
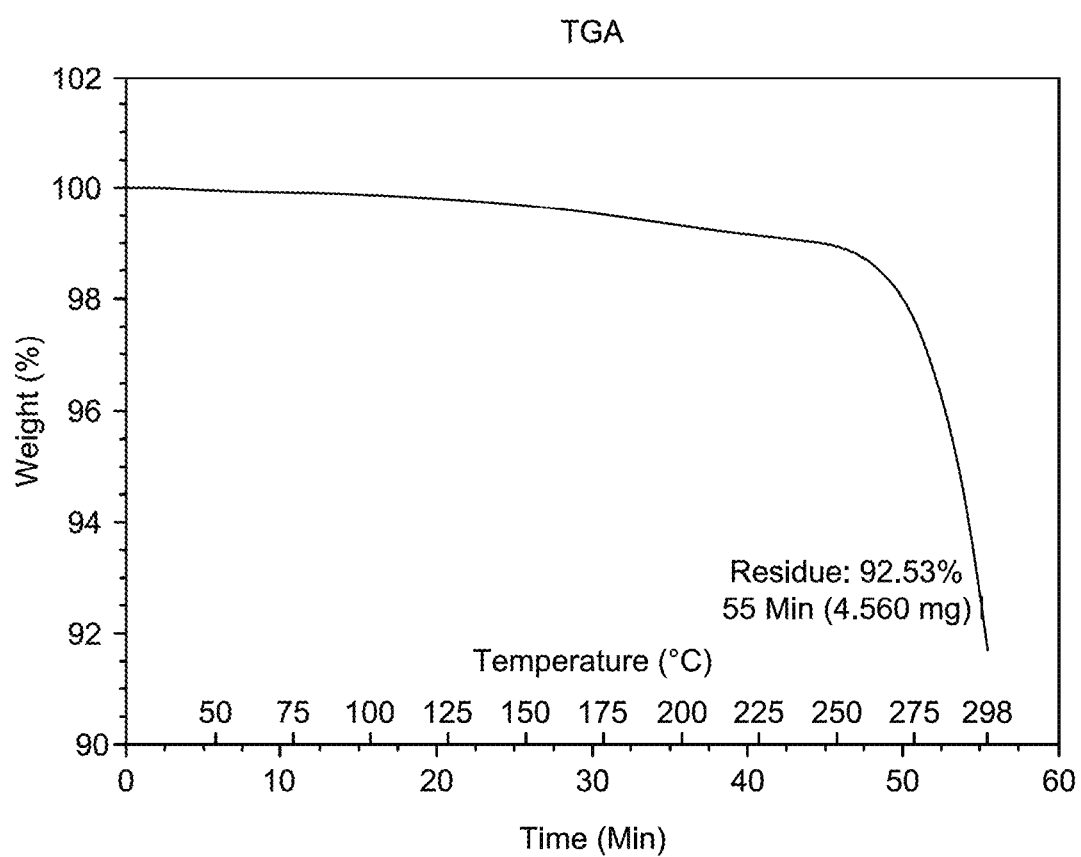
FIG. 10 depicts a thermogravimetric analysis (TGA) curve for Compound 1 Type A solid form.

The crystalline solid was determined to be the solid form of Compound 1 Type A. The DVS Isotherm of Compound 1 Type A is shown in FIG. 8. DVS shows maximum water uptake of 0.25% w/w at 25° C./90% RH, indicating Compound 1 Type A is not hygroscopic. The thermal behavior Compound 1 Type A was evaluated using DSC. An endothermic event was observed at 256.6° C. (peak max). The onset temperature and heat of fusion were 255.0° C. and 108.7 J/g respectively (FIG. 9). TGA data (FIG. 10) do not show significant release of moisture or nonaqueous residual volatiles from Compound 1 Type A.

Figure 11:
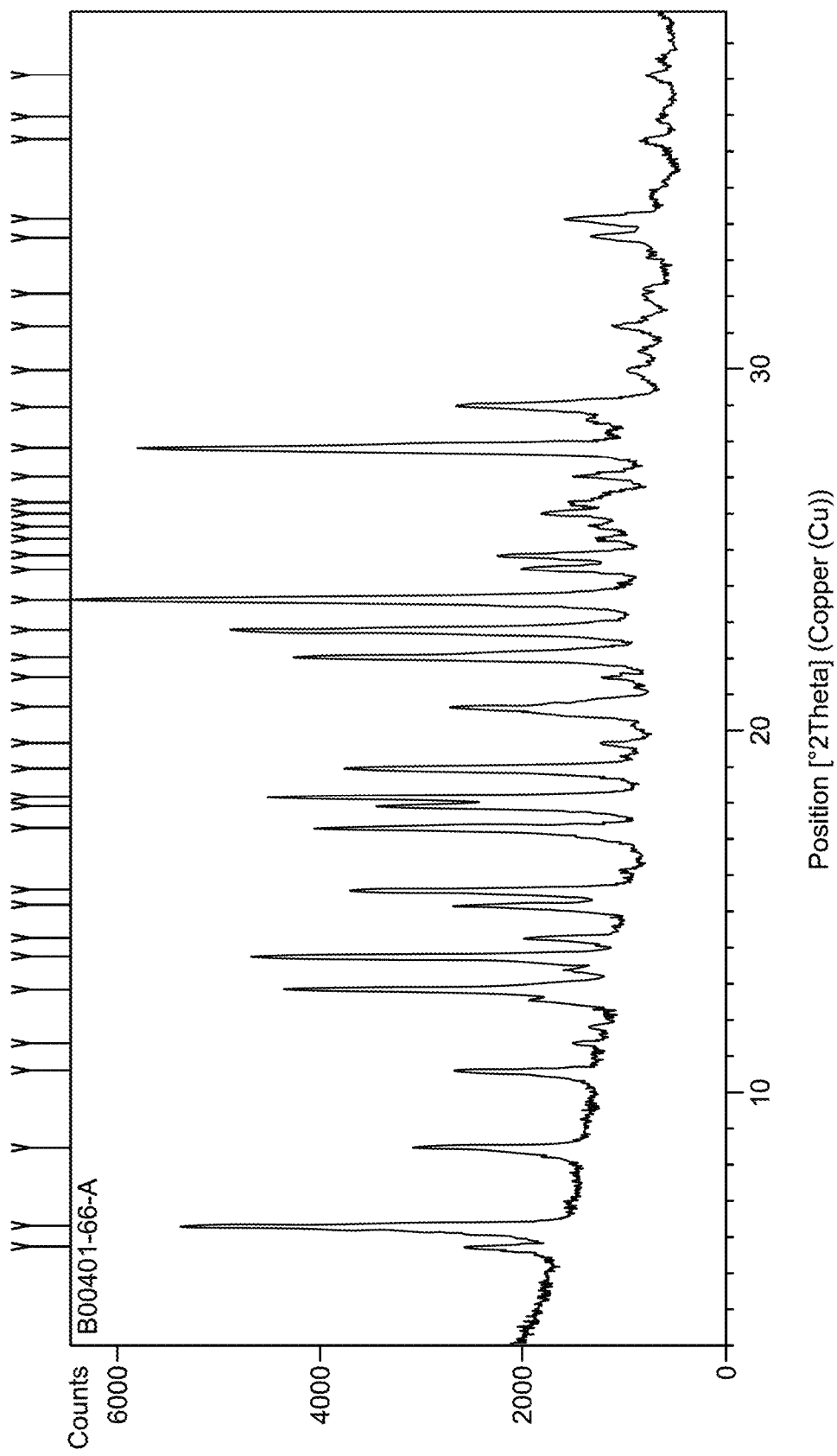
FIG. 11 depicts X-ray powder diffraction (XRPD) of Compound 1 Type A solid form.

The X-ray powder diffraction pattern of the crystalline Compound 1 Type A is depicted in FIG. 11, and the corresponding data is summarized in Table 1 below.

TABLE 1

| 2 theta ± 0.2 | d-spacing Å ± 0.2 |
| --- | --- |
| 5.7 | 15.4 |
| 6.3 | 14.0 |
| 8.5 | 10.4 |
| 10.6 | 8.4 |
| 11.4 | 7.8 |
| 12.8 | 6.9 |
| 13.8 | 6.4 |
| 14.2 | 6.2 |
| 15.2 | 5.8 |
| 15.6 | 5.7 |
| 17.3 | 5.1 |
| 17.9 | 5.0 |
| 18.2 | 4.9 |

TABLE 1-continued

| 2 theta ± 0.2 | d-spacing Å ± 0.2 |
| --- | --- |
| 18.9 | 4.7 |
| 19.6 | 4.5 |
| 20.6 | 4.3 |
| 21.5 | 4.1 |
| 22.0 | 4.0 |
| 22.8 | 3.9 |
| 23.6 | 3.8 |
| 24.5 | 3.6 |
| 24.8 | 3.6 |
| 25.3 | 3.5 |
| 25.6 | 3.5 |
| 26.0 | 3.4 |
| 26.3 | 3.4 |
| 27.0 | 3.3 |
| 27.8 | 3.2 |
| 28.9 | 3.1 |
| 30.0 | 3.0 |
| 31.2 | 3.0 |
| 32.1 | 2.8 |
| 33.6 | 2.7 |
| 34.1 | 2.6 |
| 36.3 | 2.5 |
| 37.0 | 2.4 |
| 38.1 | 2.4 |

Preferably, the oral dosage form of Compound 1 is a solid form designated Type A that is characterized by a reflection X-ray powder diffraction (XRPD) pattern comprising characteristic peaks at 6.3, 12.8, 13.8, 23.6, and 27.8 degrees±0.2° 2θ. High resolution X-ray Powder Diffraction experiments were performed with Panalytical X'Pert3 Powder XRPD on a Si zero-background holder. The 2 theta position was calibrated against Panalytical 640 Si powder standard. Details of the XRPD method are listed below, with XRPD peaks reported as diffraction angles at 2 theta, with d-spacing measured in angstroms.

| Parameters for Reflection Mode | |
| --- | --- |
| X-Ray wavelength | Cu, kα, Kα1 (Å): 1.540598, Kα2 (Å): 1.544426, Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0131 |
| Scan speed (°/s) | 0.033 |

Compound 1 is preferably administered in an oral unit dosage form comprising a pharmaceutical composition that includes the following formulation: (a) Type A solid form of Compound 1 (e.g., in a relative weight of about 33), (b) a microcrystalline cellulose (e.g., in a relative weight of about 61), (c) a croscamellose sodium (e.g., in a relative weight of about 5) and a magnesium stearate (e.g., in a relative weight of about 1). The pharmaceutical composition for oral administration can comprise Compound 1 (e.g. in a Type A solid form) with pharmaceutically acceptable excipients in a capsule or tablet. For example, a capsule may contain a total of 50 mg or 150 mg of Compound 1 in a unit dosage form. The capsule may encapsulate the pharmaceutical composition comprising Compound 1 in a relative weight of about 30-50% by weight relative to the weight of the pharmaceutical composition. In another embodiment, a GMP manufacturing batch can comprise Compound 1, optionally provided in the Type A solid form.

In particular, the Compound 1 Type A solid form can be characterized by an X-ray Powder Diffraction (XRPD), having diffractions at angles (2 theta±0.2) of 6.3, 12.8, 13.8, 23.6, and 27.8. In some embodiments, a novel Compound 1 Type A is characterized by an X-ray Powder Diffraction (XRPD), having diffractions at angles (2 theta±0.2) of 6.3, 12.8, 13.8, 23.6, and 27.8, corresponding to d-spacing (angstroms±0.2) of 14.0, 6.9, 6.4, 3.8, and 3.2, respectively. In some embodiments, Compound 1 Type A can be identified by X-ray Powder Diffraction (XRPD), having characteristic diffractions at angles (2 theta±0.2) of 5.7, 6.3, 8.5, 10.6, 12.8, 13.8, 17.3, 22.0, 22.8, 23.6, and 27.8. In some embodiments, Compound 1 Type A can be identified by X-ray Powder Diffraction (XRPD), having characteristic diffractions at angles (2 theta±0.2) of 5.7, 6.3, 8.5, 10.6, 12.8, 13.8, 17.3, 22.0, 22.8, 23.6, and 27.8, corresponding to d-spacing (angstroms±0.2) of 15.4, 14.0, 8.4, 6.9, 6.4, 5.1, 4.0, 3.9, 3.8, and 3.2, respectively.

In some embodiments, Compound 1 Type A solid form is characterized by a differential scanning calorimetry (DSC) endotherm having a minima at about 256.64° C. Differential Scanning calorimetry (DSC) experiments were performed on TA Q2000 DSC from TA Instruments. Samples were heated at 10° C./min from about 20° C. to about 300° C. using dry nitrogen to purge the system. The details of the method are provided below:

| Parameters | DSC |
|---|---|
| Pan Type | Aluminum pan, closed |
| Temperature | RT-250° C. |
| Ramp rate | 10° C./min |
| Purge gas | $N_2$ |

Step 7: Oral solid dosage form of (S)-5-((1-(6-chloro-2-oxo-1,2-dihydroquinolin-3-yl)ethyl) amino)-1-methyl-6-oxo-1,6-dihydropyridine-2-carbonitrile The oral dosage form of Compound 1 is a pharmaceutically acceptable solid form of the compound (S)-5-((1-(6-chloro-2-oxo-1,2-dihydroquinolin-3-yl)ethyl)amino)-1-methyl-6-oxo-1,6-dihydropyridine-2-carbonitrile, can be obtained using the method of Example 1 Step 6. The solid form of Compound 1 used in the oral dosage form does not contain associated solvent or a counter ion. In particular, the oral dosage form of Compound 1 can be a capsule comprising drug substance (Compound 1) blended with excipients to improve powder flow and encapsulated in a Coni-Snap® hard gelatin capsule suitable for oral dosage in humans.

Example 2

In Vitro Activity of Compound 1 as a R132X mIDH-1 Inhibitor

In in vitro biochemical assays, Compound 1 significantly inhibited mutated IDH1-R132H and IDH1-R132C proteins. In contrast, Compound 1 displayed little or no inhibitory activity in biochemical assays of wild-type IDH1 protein or various mutated IDH2 proteins found in human cancers. Compound 1 suppressed 2-HG production in naturally occurring and genetically engineered cell lines expressing five different mutated IDH1 proteins (R132H, R132C, R132G, R132L, and R132S) with $IC_{50}$ values below about 0.5 micromolar. In addition, Compound 1 has displayed relevant levels of activity against multiple clinically relevant, mutated forms of IDH1, of which IDH1-R132H and IDH1-R132C are the most prevalent in hematologic and solid tumor malignancies. However, Compound 1 did not display appreciable activity against wild-type IDH1 or mutated IDH2.

The cellular potency of Compound 1 in suppressing intracellular 2-HG levels was determined in cell lines expressing five different mutated IDH1 proteins found in human cancers (R132H, R132C, R132G, R132L, R132S). The human fibrosarcoma cell line HT-1080 harbors a naturally occurring heterozygous IDH1-R132C mutation. The human colorectal carcinoma cell line HCT 116 is wild type for IDH1, but heterozygous mutations coding for IDH1-R132H or -R132C were introduced by knock-in into the endogenous IDH1 gene locus. Finally, the human astrocytoma cell line U-87 MG is also wild type for IDH1, but expression of five different mutated IDH1 proteins was achieved by stable transfection.

The parental HCT116 line (colon) line does not produce high levels of 2-HG, but the variants used herein (X-MAN HCT-116 lines obtained from Horizon Discovery Ltd.) are engineered to knock-in a heterozygous mutation of either IDH1 R132H or IDH1 R132C. This recapitulates the cellular context in mIDH1 cancer cells where there are both wild type and mutant IDH1 subunits that together form a heterodimer that is responsible for the production of elevated levels of 2-HG. These modified lines can be used as models of IDH1 mutant disease.

Each of these cell lines was treated with Compound 1 for 24 hr, and intracellular 2-HG levels were determined by mass spectroscopy. Compound 1 suppressed 2-HG production in each cell line, with $IC_{50}$ values ranging from <10 nM to <150 nM. The table below indicates 2-HG $IC_{50}$ values: below 150 nM ("+"), below 100 nM ("++"), below 50 nM ("+++") and below 10 nM ("++++").

| Cell Line | 2-HG $IC_{50}$ (nM)* |
|---|---|
| HT-1080(IDH1-R132C/+) | ++ |
| HCT 116(IDH1-R132H/+) | +++ |
| HCT 116(IDH1-R132C/+) | + |
| U-87 MG/IDH1-R132H | +++ |
| U-87 MG/IDH1-R132C | ++ |
| U-87 MG/IDH1-R132G | ++++ |
| U-87 MG/IDH1-R132L | +++ |
| U-87 MG/IDH1-R132S | ++++ |

*Mean +/− SEM where applicable

Compound 1 is therefore a potent inhibitor of a variety of clinically relevant IDH1 mutations in a cellular context.

Example 3

Compound 1 Potently and Selectively Inhibited 2-HG Production in IDH1 R132H and IDH1 R132C Mutant Enzymes in Biochemical Assays, Compared to Wild Type IDH1 Enzyme and Mutant IDH2 Enzymes The biochemical potencies of Compound 1 against IDH1 R132H and IDH1 R132C mutants were determined in diaphorase-coupled assays, which measure activity by the determination of the level of remaining co-substrate NADPH after the enzymatic reaction is quenched. Recombinant homodimeric IDH1 R132H or IDH1 R132C mutant enzymes were used in these assays.

In order to evaluate the cellular potency of Compound 1 for other $IDH1^{R132}$ mutations that have been identified in human cancers, IDH1$^{R132L}$, IDH1$^{R132G}$ and IDH1$^{R132S}$ were expressed in U87MG human glioblastoma cells. Matched IDH1$^{R132H}$ and IDH1$^{R132C}$ lines were also prepared to allow direct comparisons in the same cellular background, as well as to compare the effects observed from the same mutation in different cell lines. As for the HT1080 and HCT-116 cell lines described above, the engineered mIDH1-expressing U87MG cells produced higher concentrations of 2-HG but exhibited a similar growth rate when compared to parental U87MG cells. Inhibition of 2-HG production by Compound 1 in the IDH1$^{R132H}$ and IDH1$^{R132C}$ U87 lines gave IC$_{50}$ values of 9.0 and 39.0 nM, respectively, which are in close agreement with those seen in the HT1080 and HCT-116 cell lines. In addition, Compound 1 potently inhibited 2-HG production in IDH1$^{R132G}$, IDH1$^{R132S}$ and IDH1$^{R132L}$ expressing cells with IC$_{50}$ values of 5.6, 9.2, and 41.7 nM, respectively, suggesting that Compound 1 is a potent inhibitor against a broad spectrum of IDH1$^{R132}$ mutants. In agreement with the previous cell lines studies, Compound 1 was found to have minimal effects on the proliferation of mIDH1 expressing U87MG cells at 10 μM.

Additional results are shown in Table 2, relative to the IC$_{50}$ value obtained for R132H IDH1 mutated enzyme. Referring to data in Table 2, Compound 1 was found to selectively inhibit the enzymatic activity of the IDH1 R132H and IDH1 R132C mutations with an IC$_{50}$ value within a factor of about 5 (i.e., the IC$_{50}$ value measured for IDH1 R132C mutant enzyme was about 5 times higher than the IC$_{50}$ measured in the IDH1 R132H mutated enzyme). The selectivity of Compound 1 against other IDH isozymes was also tested utilizing diaphorase coupled assays employing either wild-type IDH1 or one of 2 alternate mutated forms of IDH2, namely IDH2 R172K and IDH2 R140Q.

TABLE 2

| Target | Relative Enzymatic IC$_{50}$ (Average +/− SEM, nM) |
| --- | --- |
| IDH1 R132H | 1.0 (±6.6%) |
| IDH1 R132C | 5.1 (±6.1%) |
| Wild Type IDH1 | 922 |
| IDH2 R172K | >1,000 |
| IDH2 R140Q | >4,000 (no activity measured) |

Compound 1 had comparatively very weak activity against wild type IDH1 (IC$_{50}$ value of about 922 times greater than the IC$_{50}$ value measured for IDH1 R132H). Compound 1 also demonstrated very weak activity against IDH2 R172K that was more than 1,000 greater than the IC$_{50}$ value measured for IDH1 R132H. Compound 1 did not show any inhibition of IDH2 R140Q up to a concentration of 100 μM. These selectivity data indicate that Compound 1 is a potent and selective inhibitor of IDH1 R132 mutations.

Example 4

Testing Compound 1 in Mouse Xenograft Models Using HCT 116 Cells with R132C and R132H Mutations In order to assess the in vivo activity of Compound 1, PK-PD experiments in mice bearing HCT-116 xenografts (derived from Horizon Discovery isogenic cell lines harboring IDH1-R132H and IDH1-R132C knock-in mutations) were used to determine the degree of exposure required to suppress 2-HG levels. Compound 1 was administered to HCT116-IDH1-R132H+ xenograft bearing female BALB/c Nude mice at three oral doses (12.5, 25, and 50 mg/kg) in 12-hour intervals. Plasma and xenograft tumor samples were collected at 4, 12, and 24 hours post last dose to determine the exposure of Compound 1 in plasma and tumor, as well as to measure the inhibition of IDH1 mutant activity in tumor based on the reduction in levels of 2-HG.

In both IDH1 mutated models, the free concentration of Compound 1 was comparable in plasma and xenograft tumors, and exposures were dose-dependent. In comparison to the vehicle treated group, Compound 1 showed a time and dose-dependent inhibition of 2-HG levels in plasma and in tumor. At the highest dose tested in these studies (50 mg/kg), treatment with Compound 1 inhibited 2-HG levels in the tumor by >90% for up to 24 hours after the last dose in the HCT116-IDH1-R132H/+ xenograft model, and to similar levels for at least 12 hours in the HCT116-IDH1-R132C/+ model. Calculations based upon the percentage of suppression of 2-HG concentration in tumor versus the free drug concentration in tumor gave in vivo IC$_{50}$ values of 26 nM and 36 nM in the HCT116-IDH1-R132H or HCT116-IDH1-R132C models, respectively. When corrected for unbound levels of Compound 1, there is an excellent correlation in potency among the biochemical assay, cellular assay, and in vivo studies.

TABLE 3

| mIDH1-R132H | | | mIDH1-R132C | | |
| --- | --- | --- | --- | --- | --- |
| Enzyme (nM) | Cell 2-HG (nM) | In vivo 2-HG (nM) | Enzyme (nM) | Cell 2-HG (nM) | In vivo 2-HG (nM) |
| 17 | 37 | 26 | 100 | 66 | 36 |

In order to optimize the dosing schedule of Compound 1 to achieve sustained >90% 2-HG inhibition in mIDH1 in vivo, HCT116-IDH1 R132H and HCT116-IDH1 R132C xenograft-bearing mice were treated with Compound 1 at 25 and 50 mg/kg BID (3 doses). The free drug concentration of Compound 1 at 12 hour post final dose is above the in vivo IC$_{90}$ for all doses, and a greater than 90% reduction of 2-HG levels in tumor were achieved in each case. The free drug concentration decreased to 3-10× the in vivo IC$_{50}$ at 24 hour post final dose, and Compound 1 showed 80-90% (or greater) inhibition. There was less than 20 nM free drug concentration in tumor at 48 and 72 hours after final dose, and at that point there was less than 50% 2-HG inhibition in tumor samples, consistent with the reduced level of Compound 1.

Briefly, 5×10$^6$ HCT-116 IDH1-R132H/+ cells (Horizon Discovery) in PBS was inoculated subcutaneously at the right flank of the 6 weeks old female BALB/c nude mice. When the tumor size reached 360-400 mm$^3$, mice were randomized by tumor volume into nine mice per group. The tumor bearing mice were treated with vehicle (9:1 PEG400: Ethanol) or Compound 1 for three doses with 12 hr dosing interval. The dosing volume was 10 μL/g. The plasma samples and tumor samples were collected at 4, 12 and 24 hr post final dose (N=3 mice per time point) for the subsequent measurement of compound level in plasma and tumor samples and of 2-HG level in the tumor samples by UPLC-MS-MS system.

In a separate dosing example, 5×10$^6$ HCT-116 IDH1-R132C/+ cells (Horizon Discovery) in PBS were inoculated subcutaneously at the right flank of the 6-8 weeks old female BALB/c nude mice. When the tumor size reached ~250 mm$^3$, mice were randomized by tumor volume into nine mice per group. The tumor bearing mice were treated with vehicle (9:1 PEG400:Ethanol) or Compound 1 for six doses with 12 hr dosing interval. The dosing volume was 10 μL/g. The plasma samples and tumor samples were collected at 4, 8 and 12 hr post final dose (N=4 mice per time point) for the subsequent measurement of compound level in plasma and tumor samples and of 2-HG level in the tumor samples by UPLC-MS-MS system.

For each assay, the total concentration of Compound 1 was determined in μM and free Compound 1 concentration was calculated by multiplying the total Compound 1 concentration by 0.043 given that Compound 1 is 95.7% protein binding in mouse plasma. The percentage of 2-HG inhibition in individual tumor sample in the treated groups was normalized to the average of 2-HG concentration in the vehicle group at the corresponding sampling time using the following calculation: % 2-HG inhibition=100*(A−B)/A, where A is the average of 2-HG concentration at the corresponding sampling time, B is the 2-HG concentration in the tumor treated with given dose of Compound 1 and sacked at the given sampling time. The in vivo potency of Compound 1 for suppressing 2-HG in tumor is calculated by plotting the percentage of 2-HG inhibition against corresponding free Compound 1 concentration in tumor and fitting the data with four-parameter logistic equation.

IDH1-R132H Mutation

Figure 12:
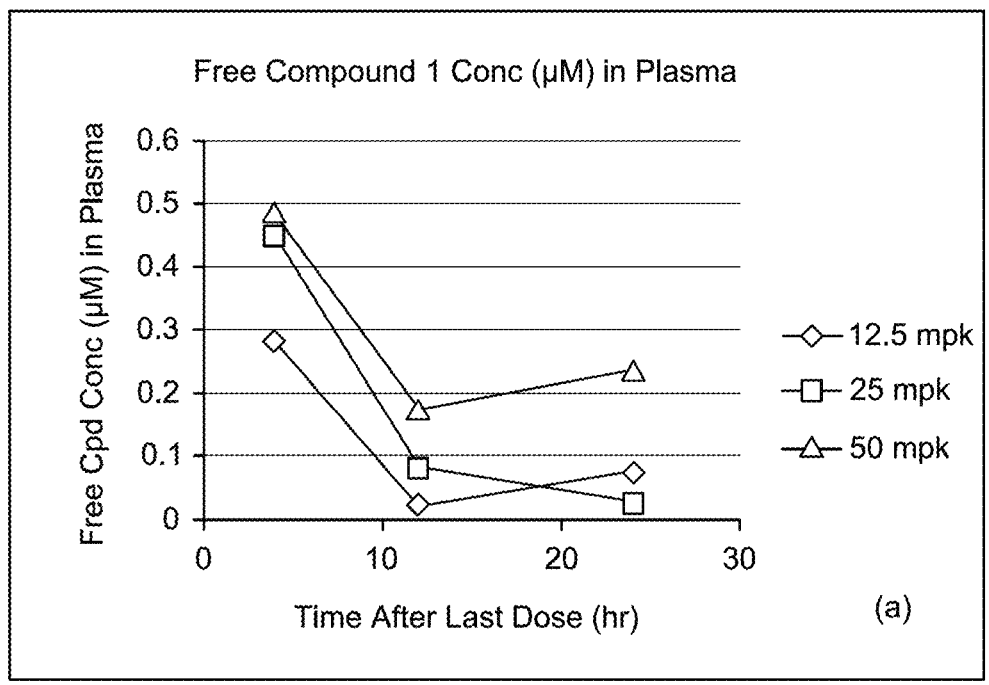
FIG. 12 consists of 4 panels: (a), (b), (c), and (d). Panel (a) illustrates free concentration of Compound 1 in plasma after three-dose oral administration (12.5, 25 and 50 mg/kg) with 12 hr dosing interval in mouse HCT116-IDH1-R132H/+ xenograft model. Panel (b) illustrates free concentration of Compound 1 in tumor after three-dose oral administration (12.5, 25 and 50 mg/kg) with 12 hr dosing interval in mouse HCT116-IDH1-R132H/+ xenograft model. Panel (c) illustrates percent 2-HG inhibition in tumors in a PO dose of 12.5 mpk, 25 mpk and 50 mpk at three different time points (4 h, 12 h, 24 h). Panel (d) illustrates in vivo activity (2-HG % inhibition) of Compound 1 vs free compound concentration in tumor.
Figure 12:
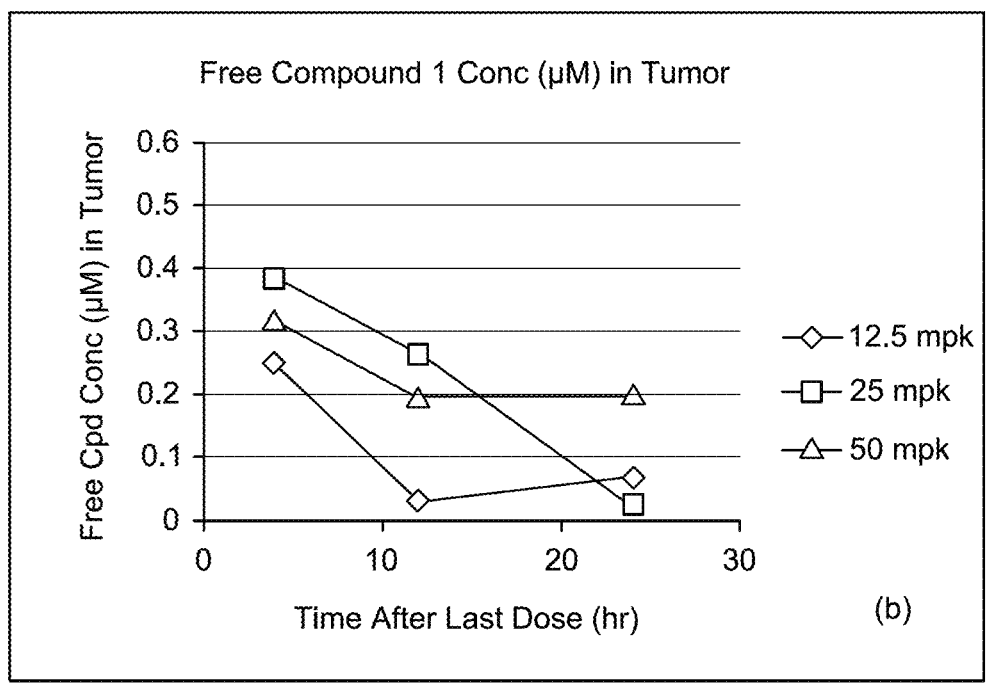
Figure 12:
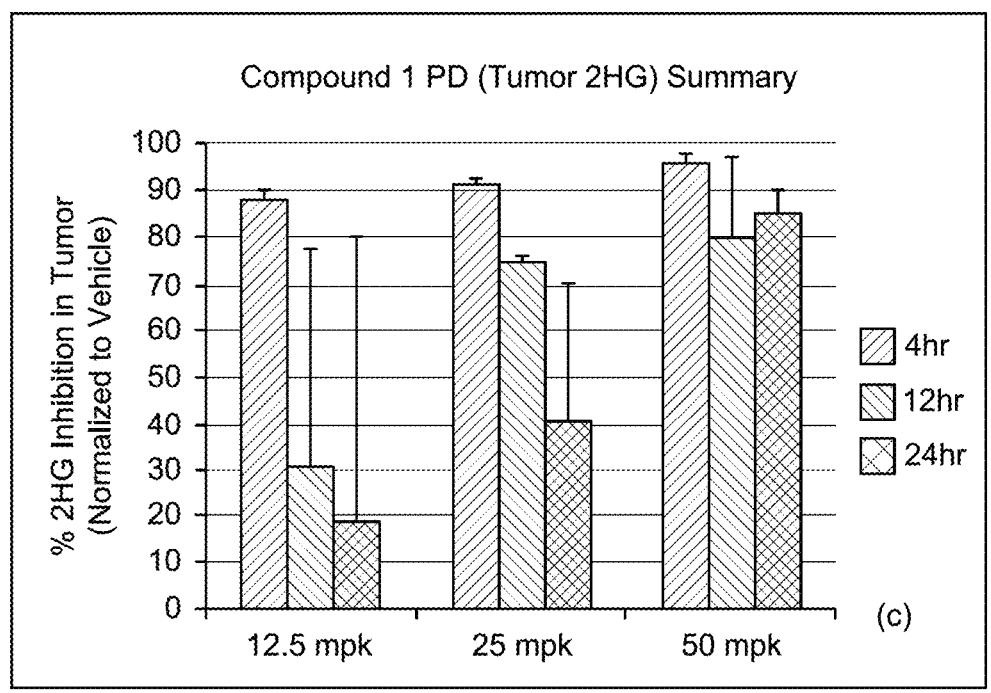
Figure 12:
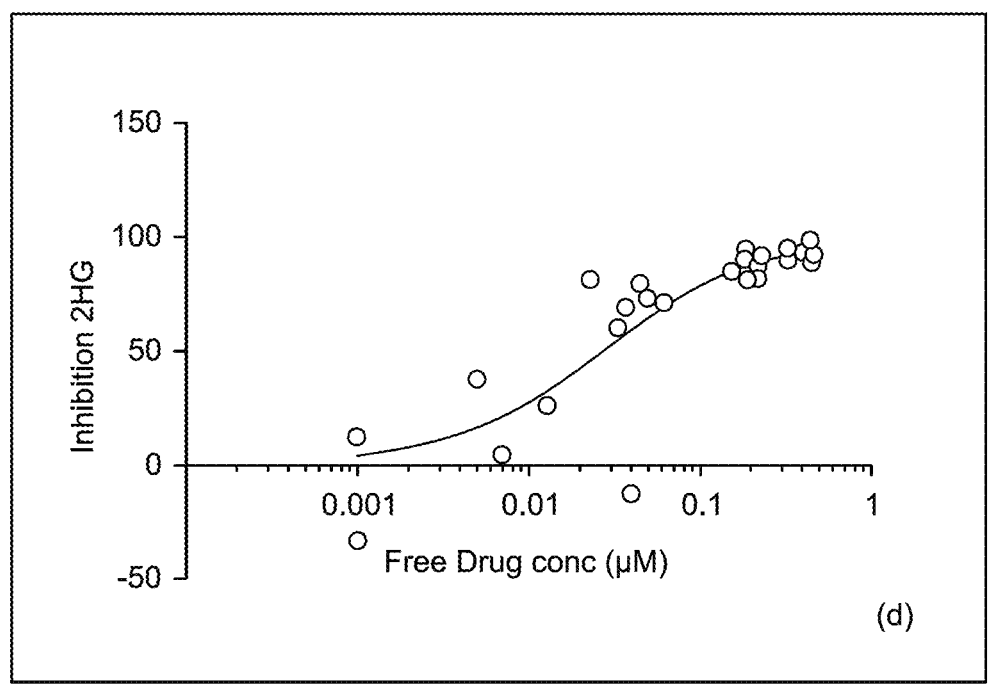

IDH1-R132H mutation resulted in elevation of 2-HG level in hematological and solid cancers. HCT-116 IDH1-R132H/+ xenograft tumor was used to assess the in vivo potency of Compound 1 to suppress 2-HG in tumor lysates. The tumor bearing mice were randomized by tumor size into twelve mice per group. The mice were treated with Compound 1 at 6.25, 12.5, 25, or 50 mg/kg for six doses with dose interval of 12 hr. The plasma and tumor samples were collected at 4, 8, and 12 hr post last dose with four mice per time point. The Compound 1 concentration in plasma and tumor samples was analyzed by LC-MS method (FIG. 12A and FIG. 12B, respectively). The 2-HG level in tumor samples was analyzed by LC-MS method. The percentage of 2-HG suppression in tumor lysate at given dose of Compound 1 was then normalized to 2-HG level in the vehicle control group (FIG. 12C). The dose and time dependent 2-HG inhibition by Compound 1 was observed in this study. The degree of 2-HG inhibition in tumor lysates was correlated with the free drug concentration in the corresponding tumor lysate. The calculated in vivo potency of Compound 1 to suppress 2-HG in tumor was 26.0 nM.

Upon correcting for unbound Compound 1 concentration, there was a good correlation between the enzymatic, cellular 2-HG, and in vivo 2-HG potencies of Compound 1 for IDH1-R132H mutant.

IDH1-R132C mutation

IDH1-R132C mutation resulted in elevation of 2-HG level in hematological and solid cancers. HCT-116 IDH1-R132C/+ xenograft tumor was used to assess the in vivo potency of Compound 1 to suppress 2-HG in tumor lysates. The tumor bearing mice were randomized by tumor size into nine mice per group. The mice were treated with Compound 1 at 12.5, 25, or 50 mg/kg for three doses with dose interval of 12 hr. The plasma and tumor samples were collected at 4, 12, and 24 hr post last dose with three mice per time point. The Compound 1 concentration in plasma and tumor samples was analyzed by LC-MS method. The 2-HG level in tumor samples was analyzed by LC-MS method. The percentage of 2-HG suppression in tumor lysate at given dose of Compound 1 was then normalized to 2-HG level in the vehicle control group. The dose and time dependent 2-HG inhibition by Compound 1 was observed in this study. The degree of 2-HG inhibition in tumor lysates was correlated with the free drug concentration in the corresponding tumor lysate. The calculated in vivo potency of Compound 1 to suppress 2-HG in tumor was 36.0 nM.

Upon correcting for unbound Compound 1 concentration, there was a good correlation between the enzymatic, cellular 2-HG, and in vivo 2-HG potencies of Compound 1 for IDH1-R132C mutant.

Results

Given the role of 2-HG in suppressing normal differentiation of mt-IDH1 cells (Figueria et al., 2010; Saha et al., 2014), it is hypothesized that in order to reverse and maintain this effect, it is necessary to achieve a very high degree of target inhibition on a continuous basis. Therefore, in order to optimize the dosing schedule of Compound 1, it is necessary to achieve sustained >90% 2-HG inhibition in mt-IDH1 in vivo. For the HCT116-IDH1$^{R132H}$ xenograft assay, the 12 and 24 hour time points were chosen to reflect the compound level and corresponding 2-HG inhibition at the $C_{trough}$ of BID and QD dosing schedules. The 48 and 72 hour time points were selected to investigate whether Compound 1 had long lasting effects on 2-HG inhibition. The free drug concentration of Compound 1 at 12 hour post final dose is above the in vivo $IC_{90}$ for all doses, and a greater than 90% reduction of 2-HG levels in tumor were achieved in each case. The free drug concentration decreased to 3-10× the in vivo $IC_{50}$ at 24 hour post final dose, and the compound showed 80-90% inhibition. There was less than 20 nM free drug concentration in tumor at 48 and 72 hours after final dose, and at that point there was less than 50% 2-HG inhibition in tumor samples, consistent with the reduced level of Compound 1. These data support the premise that constant target coverage by a significant margin is required to achieve sustained 2-HG inhibition. This experiment also suggests that a BID schedule is the preferred dosing regimen for Compound 1 in order to continuously achieve >90% 2-HG inhibition. This level of inhibition has recently been correlated to clinical efficacy with AG-221 in mt-IDH2 harboring AML patients (Fan et al., 2014)).

The present disclosure contemplates, among other things, recognition that the total concentration ($C_{eff}$) of Compound 1 must be above 1652 ng/mL in human patients in order to achieve 90% inhibition of 2-HG and above 2000 ng/mL to achieve greater than 90% inhibition of 2-HG. $C_{eff}$ was determined using assays outlined in this Example. In two separate mouse experiments, HCT-116 IDH1-R132H/+ xenografts and HCT-116 IDH1-R132C/+ xenograft tumor were used to assess the in vivo potency of Compound 1 to suppress 2-HG in tumor lysates. Compound 1 concentration in plasma and tumor samples and 2-HG level in tumor samples was measured. The degree of 2-HG inhibition in tumor lysates was correlated with the free drug concentration in the corresponding tumor lysate (see FIG. 12D). Given the role of 2-HG in suppressing normal differentiation of mt-IDH1 cells (Figueria et al., 2010; Saha et al., 2014), the present disclosure hypothesized that in order to reverse and maintain this effect, it is necessary to achieve a very high degree of target inhibition with Compound 1 on a continuous basis. It was previously proposed that >90% inhibition of 2-HG correlates to clinical efficacy in mt-IDH2 harboring AML patients (FAN, B. et al., Evaluation of the pharmacokinetic/pharmacodynamic (PK/PD) relationships of an oral, selective, first-in-class, potent IDH1 inhibitor, AG-221, from a phase 1 trial in patients with advanced IDH2 mutant positive hematologic malignancies, Blood, 124: 3737, 6 pages (2014)). Using the curve from FIG. 12D, the level of free drug concentration of Compound 1 was determined to be 0.256 µM in order to achieve 90% inhibition of 2-HG.

Using a rapid equilibrium dialysis approach, the plasma protein binding for a human patient was determined to be 94.5%. (Waters, N.J., et al. (2008)). Validation of a rapid equilibrium dialysis approach for the measurement of plasma protein binding. J Pharm Sci 97(10): 4586-95.) Accordingly, the total concentration ($C_{eff}$) can be determined: $0.256/((100-94.5)/100)=4.65$ µM=1652 ng/mL.

Example 5

Case Study of Human Clinical Trial Testing of Compound 1

Patient X is 66 y/o female, diagnosed with AML who initially received induction treatment with high dose cytarabine to which the patient was refractory. Subsequently, the patient enrolled in a clinical trial study, where she was treated with single agent (SA) Compound 1 150 mg BID and achieved a complete remission (CR) after one cycle of treatment (28 days). Patient continued treatment while in CR for 7 additional cycles. Patient then relapsed and discontinued study treatment.

Patient Y is 62 y/o male, diagnosed with FLT3-positive secondary AML (secondary to MDS). Patient received intensive chemotherapy induction with cytarabine and daunorubicin in combination with midostaurin (FLT3 inhibitor) but unfortunately was refractory. He enrolled in a clinical trial study, where he was treated with Compound 1 150 mg BID in combination with azacitidine for a total of 8 cycles (1 cycle=28 days). He achieved complete remission with IDH1 mutation clearance (CRm) by cycle 6 and discontinued study treatment after cycle 8 to undergo bone marrow transplant (HSCT).

Patient Z is a 50 year old diagnosed with grade III IDH1m glioma (anaplastic astrocytoma) previously treated with chemotherapy and radiation according to the applicable standard of care. This patient was subsequently enrolled in the clinical study and treated with Compound 1 at 150 mg twice daily (BID) each day. Following treatment with Compound 1 for 2 cycles (each cycle=28 consecutive days receiving 150 mg Compound 1 BID), by MRI, patient was determined by the investigator to have experienced a partial response by RANO criteria (≥50% decrease in tumor, no new lesions, on stable dose corticosteroids, no progression of measurable disease). After receiving 2 cycles of Compound 1 (150 mg BID), the patient remains on treatment with 150 mg BID Compound 1 per protocol.

3 Patients received a Compound 1 at 100 mg once daily (QD) each day. Blood samples were collected every 28 days for measurement of plasma concentrations of Compound 1 (single agent). Blood was collected at the following times relative to Compound 1 administration:
  Cycle 1 Day 1: predose, and postdose at 30 minutes, 1, 2, 4, and 8 hours
  Cycle 1 Days 2, 8, 15, and 22: predose
  Cycle 2 Day 1: predose, and postdose at 30 minutes, 1, 2, 4, and 8 hours
  Cycle 2 Day 2: 24 hours after C2D1 dosing (±2 hours) for patients in dose expansion
  Cycle 2 Day 4: predose [72 hours after C2D1 dosing (±4 hours)] for patients in dose expansion only
  Cycle 2 Day 15: predose
  Cycle 3 and Beyond: Predose on Day 1 of every cycle The observed $C_{min}$ associated with this case study can be found in FIG. 13.

Example 6

A Phase 1 Dose Escalation Study of the mIDH-1 Inhibitor, Compound 1, in Patients with AML or Myelodysplastic Syndrome (MDS)

Isocitrate dehydrogenase 1 mutations (mIDH-1) occur in 7-14% of AML patients ("pts.") and 3% of MDS pts. Compound 1 is a highly potent, selective small molecule inhibitor of mIDH-1 without anticipated CYP or QTc liabilities at the recommended phase 2 dose. Compound 1 was tested in a Phase 1/2 study to evaluate the safety, efficacy, PK, and PD of Compound 1 as a single agent or in combination with azacitidine or cytarabine.

FIG. 5A illustrates the summary of cohorts from a phase 1 study in IDH1m AML and MDS, described in this example. The Phase 1/2 study of Compound 1 was initiated to evaluate the safety, PK/PD, and clinical activity of Compound 1 alone or in combination with azacitidine (AZA) or cytarabine in mIDH-1 AML/MDS pts. In the phase 1 portion of the study, Compound 1 was dose escalated in a 3+3 design to define the maximum tolerated doses (MTDs) or maximum evaluated doses (MEDs) as a single-agent (SA) and in combination with azacitidine (CO) followed by expansion cohorts. Doses evaluated were 150 mg QD (SA, CO), 300 mg QD (SA), and 150 mg BID (SA, CO). Safety was assessed by incidence and severity of treatment emergent AEs (TEAEs) for all pts and efficacy derived by IWG criteria (2003 AML and 2006 MDS) based on investigator assessment for evaluable pts.

Figure 14:
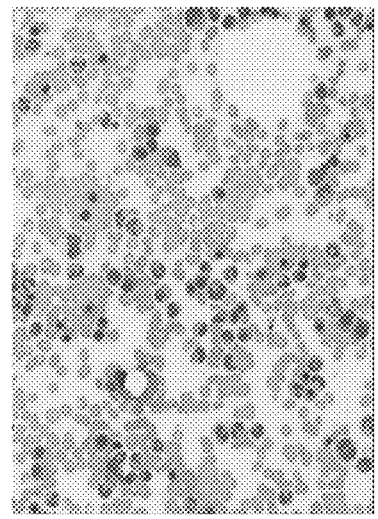
FIG. 14 is a graph showing cycle 1, grade 2 IDH-DS is resolved with dexamethasone and hydroxyurea. C2D1: CRp (1% blasts) to SCT in MLFS.
Figure 14:
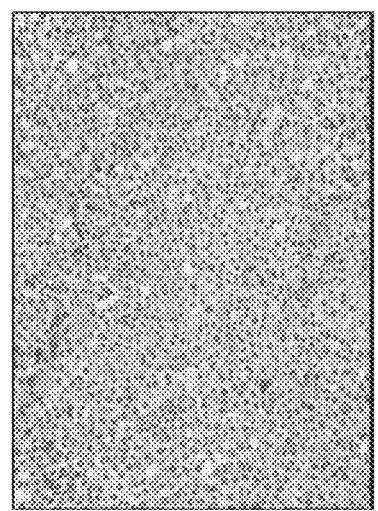

FIG. 14 illustrates cycle 1, grade 2 IDH-DS is resolved with dexamethasone and hydroxyurea. C2D1: CRp (1% blasts) to SCT in MLFS, during the clinical trial of this Example.

Subject Inclusion Criteria can include:
  1. Pathologically proven AML or intermediate, high-risk, or very high risk MDS as defined by the World Health Organization (WHO) criteria or Revised International Prognostic Scoring System (IPSS-R) which is relapsed or refractory (R/R) to standard therapy and/or for which standard therapy is contraindicated or which has not adequately responded to standard therapy, e.g. Compound 1 as a single agent: patient has received no prior IDH1 inhibitor or Compound 1 in combination with Aza: patients are treat-naïve & eligible for Aza, patients can have received IDH1m inhibitor or HMA.
  2. Patients must have documented IDH1-R132 gene-mutated disease as evaluated by the site.
  3. Good performance status.
  4. Good kidney and liver function.
  5. Baseline QTcF≤450 msec.
  6. No exclusions for concomitant medications.

Subject Exclusion Criteria can Include:
  1. Patients with symptomatic central nervous system (CNS) metastases or other tumor location (such as spinal cord compression, other compressive mass, uncontrolled painful lesion, bone fracture, etc.) necessitating an urgent therapeutic intervention, palliative care, surgery or radiation therapy.
  2. Congestive heart failure (New York Heart Association Class III or IV) or unstable angina pectoris. Previous history of myocardial infarction within 1 year prior to study entry, uncontrolled hypertension or uncontrolled arrhythmias.

3. Pulmonary disease (e.g. COPD, asthma, etc.) that is not controlled (moderate to severe symptoms) with current medication.
4. Active, uncontrolled bacterial, viral, or fungal infections, requiring systemic therapy.

Treatment/Intervention Plan

Compound 1 was administered as a single agent or in combination with azacitidine or cytarabine. Compound 1 was supplied as 50 mg or 150 mg capsules and was administered per the protocol defined frequency and dose level. Azacitidine was administered per site's standard of care. Cytarabine will be administered per site's standard of care.

The Phase 1 stage of the study was split into 2 distinct parts: a dose escalation part, which will utilize an open-label design of Compound 1 (single agent), or Compound 1+azacitidine (combination agent), or Compound 1+cytarabine (combination agent) administered via one or more intermittent dosing schedules, followed by a dose expansion part. The dose expansion part will enroll patients in up to 5 expansion cohorts, exploring single-agent Compound 1 activity as well as combination activity with azacitidine or cytarabine. Patients may receive only a single dose of study drug (single-agent arm and combination arm) on Cycle 1 Day 1. Following the completion of the relevant Phase 1 cohorts, Phase 2 begins enrollment. Patients are enrolled across 6 different cohorts, examining the effect of Compound 1 (as a single agent) and Compound 1 with azacitidine (combination) on various AML/MDS disease states. Conditions examined include acute myeloid leukemia (also known as acute myelogenous leukemia) and myelodysplastic syndrome.

TABLE 4

Arms and Interventions of Phase 1 Trial.

| Arms | Assigned Interventions |
|---|---|
| Experimental: PH1 Dose Escalation & Expansion Compound 1 | Drug: Compound 1<br>Compound 1 is supplied as 50 mg or 150 mg capsules and is administered per the protocol defined frequency and dose level |
| Experimental: PH1 Esc. and Exp. Compound 1 + Azacitidine | Drug: Compound 1<br>Compound 1 is supplied as 50 mg or 150 mg capsules and is administered per the protocol defined frequency and dose level<br>Drug: Azacitidine (Vidaza)<br>azacitidine is administered per site's standard of care |
| Experimental: PH1 Esc. and Exp. Compound 1 + Cytarabine | Drug: Compound 1<br>Compound 1 is supplied as 50 mg or 150 mg capsules and is administered per the protocol defined frequency and dose level<br>Drug: Cytarabine<br>low-dose cytarabine are administered per site's standard of care |
| Experimental: PH2 Cohort 1 Compound 1<br>Single Agent Relapsed or Refractory (R/R) AML | Drug: Compound 1<br>Compound 1 is supplied as 50 mg or 150 mg capsules and is administered per the protocol defined frequency and dose level |
| Experimental: PH2 Cohort 2 Compound 1<br>Single Agent<br>AML/MDS in morphologic complete remission or complete remission with incomplete blood count recovery (CR/CRi) after cytotoxic-containing induction therapy with residual IDH-R132 mutation | Drug: Compound 1<br>Compound 1 is supplied as 50 mg or 150 mg capsules and is administered per the protocol defined frequency and dose level |
| Experimental: PH2 Cohort 3 Compound 1<br>Single Agent<br>R/R AML/MDS, previously treated with an IDH1 inhibitor | Drug: Compound 1<br>Compound 1 is supplied as 50 mg or 150 mg capsules and is administered per the protocol defined frequency and dose level |
| Experimental: PH2 Cohort 4 Compound 1 + Azacitidine<br>R/R AML/MDS that are naïve to prior hypomethylating therapy and IDH1 inhibitor therapy | Drug: Compound 1<br>Compound 1 is supplied as 50 mg or 150 mg capsules and is administered per the protocol defined frequency and dose level<br>Drug: Azacitidine (Vidaza)<br>Azacitidine is administered per site's standard of care |
| Experimental: PH2 Cohort 5 Compound 1 + Azacitidine<br>R/R AML/MDS that have inadequately responded or have progressed immediately preceeding hypomethylating therapy | Drug: Compound 1<br>Compound 1 is supplied as 50 mg or 150 mg capsules and is administered per the protocol defined frequency and dose level<br>Drug: Azacitidine (Vidaza)<br>Azacitidine is administered per site's standard of care |
| Experimental: PH2 Cohort 6 Compound 1 + Azacitidine<br>R/R AML/MDS that have been previously treated with single-agent IDH1 inhibitor therapy as their last therapy prior to study enrollment | Drug: Compound 1<br>Compound 1 is supplied as 50 mg or 150 mg capsules and is administered per the protocol defined frequency and dose level<br>Drug: Azacitidine (Vidaza)<br>azacitidine is administered per site's standard of care |

Following the completion of Phase 1, Phase 2 enrollment began. Patients were enrolled across 6 different cohorts, examining the effect of Compound 1 (as a single agent) and Compound 1+azacitidine (combination) on various AML/MDS disease states. The Phase 2 cohorts are summarized in Table 5 below:

TABLE 5

| Cohort | Patient Population | Intervention |
|---|---|---|
| I | Patients with relapsed or refractory (R/R) AML | Recommended phase II dose ("RP2D") of Compound 1 as a single-agent |
| II | Patients with AML/MDS in morphologic complete remission or complete remission with incomplete blood count recovery (CR/CRi) after cytotoxic-containing induction therapy with residual IDH-R132 mutation | RP2D of Compound 1 as a single-agent |
| III | Patients with R/R AML/MDS, previously treated with an IDH1 inhibitor | RP2D of Compound 1 as a single-agent |
| IV | Patients with R/R AML/MDS that are naïve to prior hypomethylating therapy and IDH1 inhibitor therapy | RP2D of Compound 1 in combination with azacitidine |
| V | Patients with R/R AML/MDS that have inadequately responded or have progressed immediately preceding hypomethylating therapy | RP2D of Compound 1 in combination with azacitidine |
| VI | Patients with R/R AML/MDS that have been previously treated with single-agent IDH1 inhibitor therapy as their last therapy prior to study enrollment | RP2D of Compound 1 in combination with azacitidine |

Primary Outcome Measures

The outcome of the study can be evaluated using the following criteria:
1. Maximum Tolerated Doses (MTDs) or Maximum Evaluated Doses (MEDs) [Phase 1]. Time Frame: Within first 4 weeks of treatment.
2. Number of Participants with a Dose Limiting Toxicity (DLT) [Phase 1]. Time Frame: Within first 4 weeks of treatment. DLT Criteria can include:
   ≥Gr 3 non-hematologic toxicity or laboratory finding
   Gr 4 hematologic toxicity by Day 42 in absence of disease
   Inability to tolerate at least 75% of Cycle 1 treatment
3. Doses recommended for future studies [Phase 1]. Time Frame: Within first 4 weeks of treatment.
4. Complete Response (CR, CRi, MLFS, Marrow CR) Rate of Compound 1 as a single-agent or in combination with azacitidine in patients with AML/MDS [Phase 2]. Time Frame: As per IWG Response Assessment Guidelines for AML and MDS based on investigator's assessment through study completion, e.g. modified IWG AML 2003/MDS 2006.

Secondary Outcome Measures

The outcome of the study can also be evaluated using the following criteria:
1. Area under the plasma concentration versus time curve (AUC) [Phase 1 and Phase 2]. Time Frame: Blood samples for PK analysis collected at multiple visits during the first 60 days of treatment and on day 1 of all cycles following the first 30 days.
2. Peak Plasma Concentration (Cmax) [Phase 1 and Phase 2]. Time Frame: Blood samples for PK analysis collected at multiple visits during the first 60 days of treatment and on day 1 of all cycles following the first 30 days.
3. Time of peak plasma concentration (Tmax) [Phase 1 and Phase 2]. Time Frame: Blood samples for PK analysis collected at multiple visits during the first 60 days of treatment and on day 1 of all cycles following the first 30 days.
4. Time for half of the drug to be absent in blood stream following dose (T 1/2) [Phase 1 and Phase 2]. Time Frame: Blood samples for PK analysis collected at multiple visits during the first 60 days of treatment and on day 1 of all cycles following the first 30 days.
5. Rate at which drug is removed from blood stream (CL/F) [Phase 1 and Phase 2]. Time Frame: Blood samples for PK analysis collected at multiple visits during the first 60 days of treatment and on day 1 of all cycles following the first 30 days.
6. Rate of drug distribution within the blood stream (Vd/F) [Phase 1 and Phase 2]. Time Frame: Blood samples for PK analysis collected at multiple visits during the first 60 days of treatment and on day 1 of all cycles following the first 30 days.
7. Reduction of 2-HG levels in plasma [Phase 1 and Phase 2]. Time Frame: Blood samples for PK/PD analysis collected at multiple visits during the first 60 days of treatment and on day 1 of all cycles following the first 30 days.
8. Evidence of antileukemic or antimyelodysplastic activity of Compound 1 as determined by complete response (CR), CRi (complete remission with incomplete hematologic recovery), morphologic leukemia-free state (MLFS), Marrow CR, partial remission (PR), and stable disease (SD) as a single-agent or in combination with azacitidine or cytarabine [Phase 1]. Time Frame: As per IWG Response Assessment Guidelines for AML and MDS based on investigator's assessment through study completion.
9. Incidence and severity of adverse events, clinical laboratory abnormalities, and changes in ECG parameters as assessed by CTCAE v4.0 as a single-agent or in combination with azacitidine [Phase 2]. Time Frame: Safety will be assessed from time of first dose through 28 days post last dose.
10. Additional measures of antileukemic or antimyelodysplastic activity as determined by CRh, Overall Response (OR), and Stable Disease of Compound 1 alone or in combination with azacitidine [Phase 2]. Time Frame: As per IWG Response Assessment Guidelines for AML and MDS based on investigator's assessment through study completion.
11. Time to Response (TTR) [Phase 2]. Time Frame: From first dose of study drug through time of first response by blood recovery count.
12. Duration of Response (DOR) [Phase 2]. Time Frame: From time of first response by blood recovery count through relapse.
13. Event-Free Survival (EFS) [Phase 2]. Time Frame: From time of entry on study through progression.
14. Overall Survival (OS) [Phase 2]. Time Frame: From time of entry on study through death or date last known alive at end of follow-up.

Disease History and Baseline Characteristics of Exemplary Participants

A summary the disease history and baseline characteristics of exemplary participants is shown in Table 6.

TABLE 6

| Characteristic | Compund 1<br>n = 31 | Compund 1 +<br>Azacitidine<br>n = 41 |
|---|---|---|
| Age, median (range), years | 71 (35-87) | 66 (31-88) |
| Female, % | 52 | 51 |
| ECOG PS - 0/1/2, % | 25/65/10 | 32/51/17 |
| IDH1 mutation type R132-, n | C (13)/H (9)/S (4)/<br>G (4)/L (1) | C (22)/H (12)/S (4)/<br>G (2)/Others (1*) |
| AML, n | 25 | 35 |
| Relapsed (>12 mo) | 14 | 1 |
| Relapsed (≤12 mo) | 4 | 10 |
| Refractory | 8 | 15 |
| Treatment- naïve | 3 | 9 |
| Secondary AML | 3 | 12 |
| t-AML | 1 | 1 |
| Prior regimens, median (range) | 2 (0-10) | 3 (0-6) |
| Prior HMA/IDHm inhibitor/Both | no prior IDHm inhibitor | 6/3/1 |
| MDS, n | 6 | 6 |
| Relapsed/Refractory | 4 | 2 |
| Treatment naïve | 2 | 4 |
| Prior regimens, median (range) | 1 (0-4) | 1 (0-4) |
| Prior HMA/IDHm inhibitor/Both | no prior IDHm inhibitor | 2/0/0 |

*One patient with a different non-R132 mutation variant

Results

In the human clinical trial described in this Example, when Compound 1 was administered as a single agent, it provided a 41% overall response rate (ORR) and 27% CR/CRh in R/R AML. Combination of Compound 1 with azacitidine provided a 46% ORR and 16% CR/CRh in R/R AML.

At the data cutoff, 35 pts with a median of 2 prior regimens (range 1-9) had received Compound 1 in dose-escalation, including 31 single-agent (SA) and 41 azacitidine combination (CO) pts. Steady-state exposure that exceeded the target $IC_{90}$ for mIDH-1 was achieved at 150 mg BID, resulting in a reduction of 2-HG to normal levels in the majority of pts. Furthermore, administration of Compound 1, both as SA and in CO at 150 mg BID, enabled all pts to achieve the target Css that exceeded the $IC_{90}$ for mIDH-1 while staying below the exposures projected from the monkey toxicology studies that could be associated with QT prolongation. PK data were available through Cycle 10; steady state plasma drug levels were maintained at target Css over the evaluated period. A reduction of 2-HG was observed across all dose levels, with pts receiving 150 mg BID having a median within the normal 2-HG limits.

Figure 15A:
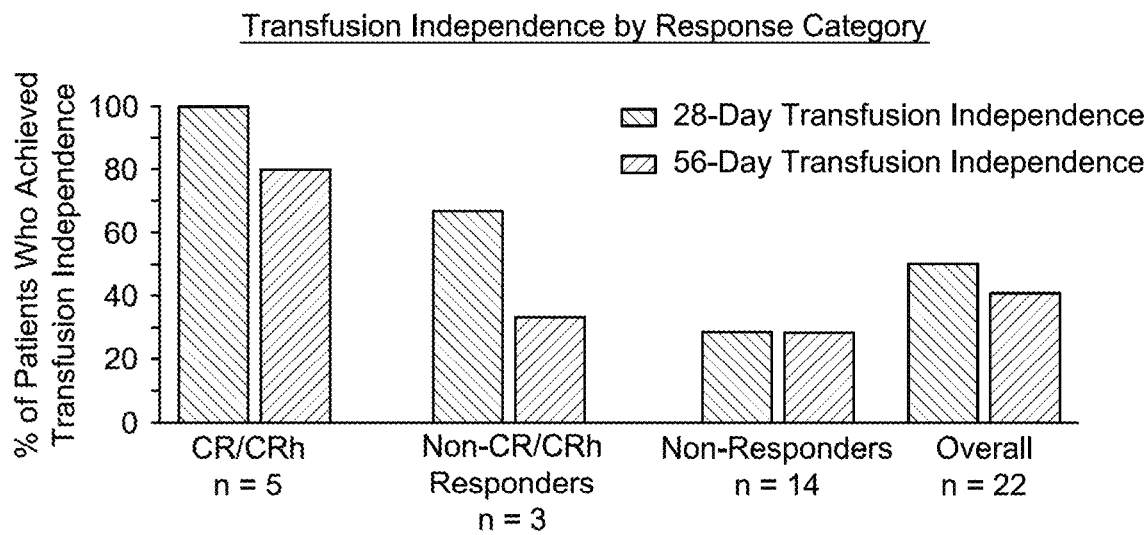
FIG. 15A is a graph of % patients who achieved transfusion independence (28- and 56-day) by category (CR/CRh, Non-CR/CRh, non-responders and overall), illustrating transfusion independence by response category for patients treated with Compound 1 as a single agent.
Figure 15B:
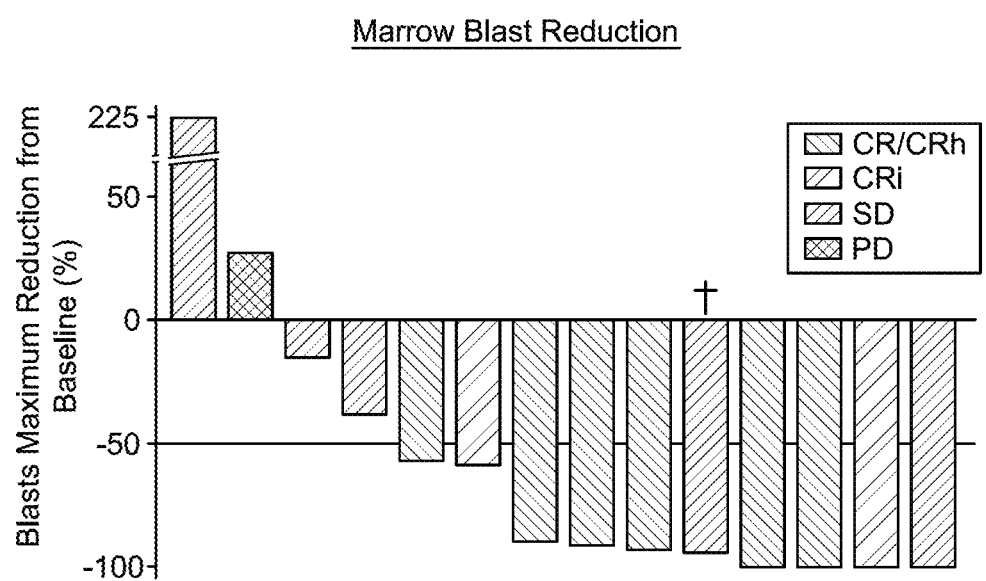
FIG. 15B is a graph showing blasts maximum reduction from baseline (%) based on category (CR/CRh, CRi, SD and PD), illustrating marrow blast reduction for patients treated with Compound 1 as a single agent.

As shown in FIG. 15A, transfusion independence (platelets and/or red blood cells) was observed in all response categories in AML patients treated with Compound 1 as a single agent who were transfusion-dependent at baseline. As shown in FIG. 15B, significant reduction in bone marrow blast content was observed in patients with a CR/CRi response per IWG response criteria. Reductions in bone marrow blast content were also observed in patients in the absence of IWG response (stable disease) including 1 subject (denoted with † in FIG. 15B) with bone marrow blast count <5% but with blasts present in peripheral blood.

The responses per Investigator assessment per modified IWG are summarized in Table 7:

TABLE 7

Responses to Compound 1 as a single agent.

| Response | R/R AML<br>N = 22 | All AML & MDS<br>N = 31 |
|---|---|---|
| ORR, n (%)* | 9 (41) | 11 (35) |
| [95% CI] | [21, 64] | [19, 55] |
| CR, n (%) | 4 (18) | 5 (16) |
| CRh, n (%) | 2 (9) | 2 (6) |
| CRi, n (%) | 3 (14) | 4 (13) |
| PR, n (%) | 0 | 0 |
| MLFS, n (%) | 0 | 0 |
| SD, n (%) | 5 (23) | 11 (35) |
| PD, n (%) | 1 (5) | 1 (3) |
| NE, n (%) | 7 (32) | 8 (26) |

Figure 16A:
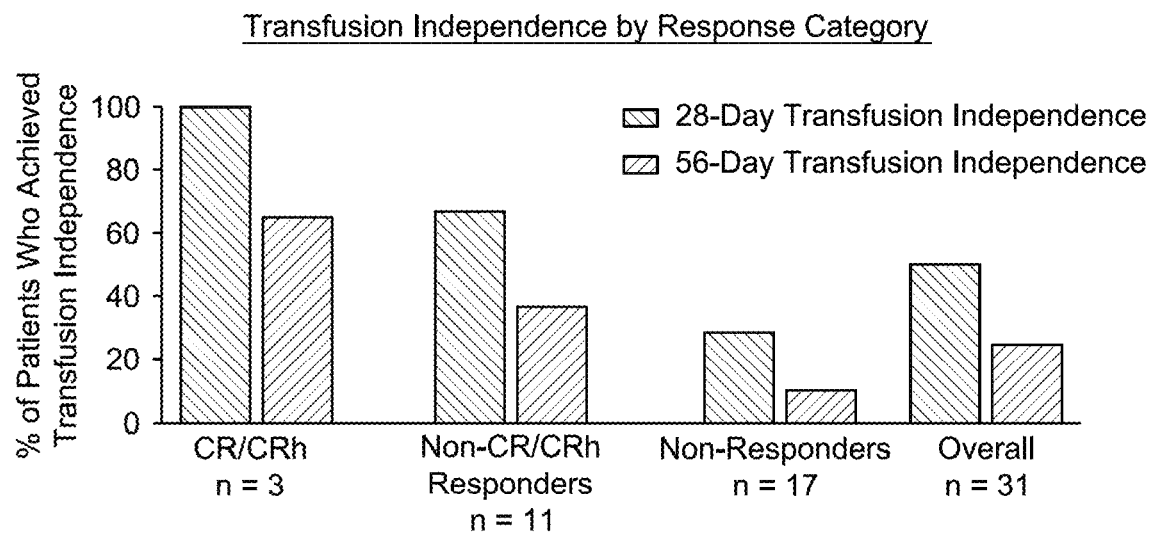
FIG. 16A is a graph of % patients who achieved transfusion independence (28- and 56-day) by category (CR/CRh, Non-CR/CRh, non-responders and overall), illustrating transfusion independence by response category for patients treated with Compound 1 in combination with azacitidine.
Figure 16B:
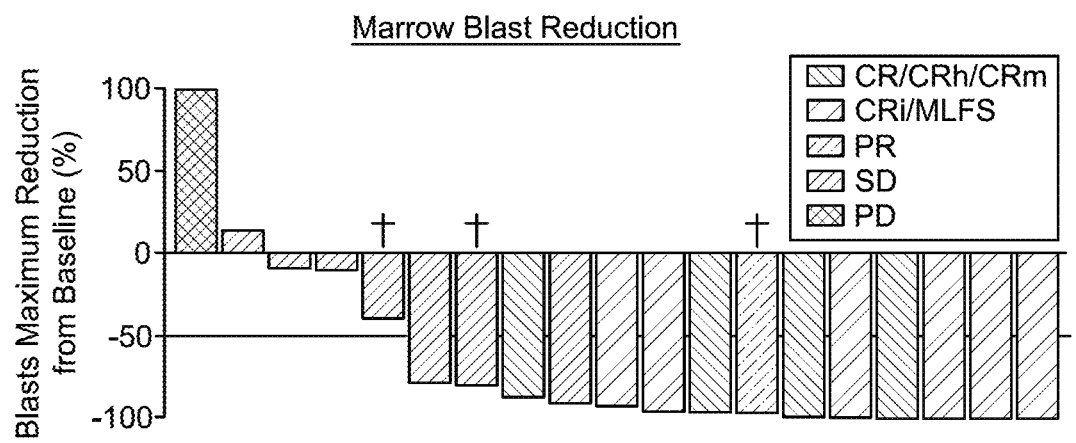
FIG. 16B is a graph showing blasts maximum reduction from baseline (%) based on category (CR/CRh, CRi, SD and PD), illustrating marrow blast reduction for patients treated with Compound 1 in combination with azacitidine.

As shown in FIG. 16A, transfusion independence (platelets and/or red blood cells) was observed in all response categories in AML patients treated with Compound 1 and azacitidine who were transfusion-dependent at baseline. As shown in FIG. 16B, reduction in bone marrow blast content was observed in patients with a CR/CRi response per IWG response criteria. Reductions in bone marrow blast content were also observed in patients in the absence of IWG response (stable disease) including 1 subject (denoted † in FIG. 16B) with bone marrow blast count <5% but with blasts present in peripheral blood. Marrow blast reduction >50% in patients with SD indicates clinical activity in the absence of IWG response.

The responses per Investigator assessment per modified IWG are summarized in Table 8.

TABLE 8

Responses to Compound 1 + azacitidine.

| Response | R/R AML<br>N = 26 | TN AML<br>N = 9 | All AML & MDS<br>N = 41 |
|---|---|---|---|
| ORR, n (%)* | 12 (46) | 7 (78) | 22 (54) |
| [95% CI] | [27, 67] | [40, 97] | [37, 69] |
| CR, n (%) | 3 (12) | 2 (22) | 8 (20) |
| CRh, n (%) | 1 (4) | 0 | 1 (2) |
| CRi, n (%) | 5 (19) | 4 (44) | 9 (22) |
| PR, n (%) | 1 (4) | 1 (11) | 2 (5) |
| MLFS, n (%) | 2 (8) | 0 | 2 (5) |
| SD, n (%) | 11 (42) | 1 (11) | 14 (34) |
| PD, n (%) | 1 (4) | 0 | 1 (2) |
| NE, n (%) | 2 (8) | 1 (11) | 4 (10) |

Exemplary Patient Disposition

A summary of the patient disposition is shown in Table 9.

TABLE 9

| Characteristic | Compound 1<br>n = 31 (%) | Compound 1 +<br>Azacitidine<br>n = 27 (%) |
|---|---|---|
| Patients enrolled, n | 31 | 27 |
| Patients treated | 31 (100) | 26 (96) |
| Median months on treatment (range) | 3 (<1-20 m) | 3 (<1-12 m) |
| Patients on treatment | 13 (42) | 13 (50) |
| Discontinued treatment | 18 (58) | 13 (50) |
| Reason for Discontinuation | | |
| Death | 6 | 4 |
| Progressive disease | 9 | 6 |

TABLE 9-continued

| Characteristic | Compound 1 n = 31 (%) | Compound 1 + Azacitidine n = 27 (%) |
|---|---|---|
| Transplant | 4 | 6 |
| Other * | 3 | 3 |
| Investigator decision | 2 | 5 |
| Withdrawal of consent | 1 | 0 |
| Adverse event | 3 | 2 |

*SA: 3 patients discontinued due to resistant disease/lack of response
Combo: 1 patient discontinued for refusal of treatment, 1 patient to enter hospice, and 1 patient with no reason for discontinuation given.

Treatment-Emergent Adverse Events (TEAEs) >15% All Grades

A summary of TEAEs can be found in Tables 10 and 11.

TABLE 10

| | Compound 1, n = 31 (Single Agent) | |
|---|---|---|
| AE Preferred Term | All Grade (%) | Grade 3/4 (%) |
| Fatigue | 13 (42) | 1 (3) |
| Nausea | 13 (42) | 0 |
| Pyrexia | 10 (32) | 2 (7) |
| Pneumonia | 7 (23) | 5 (16) |
| Vomiting | 7 (23) | 0 |
| Dyspnea | 7 (23) | 0 |
| Diarrhea | 6 (19) | 0 |
| Dizziness | 6 (19) | 1 (3) |
| Decreased Appetite | 6 (19) | 0 |
| Constipation | 6 (19) | 1 (3) |
| Hypokalemia | 6 (19) | 2 (7) |
| AST | 5 (16) | 2 (7) |
| Abdominal distention | 5 (16) | 0 |
| Epistaxis | 5 (16) | 1 (3) |
| Headache | 5 (16) | 0 |
| Thrombocytopenia[1] | 9 (29) | 9 (29) |
| Leukocytosis | 8 (26) | 4 (13) |
| Anemia | 7 (23) | 7 (23) |
| Febrile neutropenia | 7 (23) | 7 (23) |

[1]Includes preferred term of platelet count decreased

TABLE 11

| | Compound 1, n = 41 (Cpd 1 + AZA) | |
|---|---|---|
| AE Preferred Term | All Grade (%) | Grade 3/4 (%) |
| Nausea | 20 (49) | 3 (7) |
| Constipation | 20 (49) | 1 (2) |
| Hypokalemia | 15 (37) | 4 (10) |
| Fatigue | 15 (37) | 7 (17) |
| Diarrhea | 13 (32) | 2 (5) |
| Vomiting | 9 (22) | 0 |
| Headache | 9 (22) | 1 (2) |
| Decreased Appetite | 8 (20) | 1 (2) |
| Cough | 7 (17) | 1 (2) |
| Pneumonia | 7 (17) | 6 (15) |
| Pruritus | 7 (17) | 0 |
| Dysgeusia | 7 (17) | 0 |
| Creatinine increased | 7 (17) | 1 (2) |
| Dizziness | 6 (15) | 1 (2) |
| Asthenia | 6 (15) | 2 (5) |
| Abdominal Pain | 6 (15) | 1 (2) |
| Thrombocytopenia[1] | 15 (37) | 12 (29) |
| Febrile neutropenia | 12 (29) | 12 (29) |
| Neutropenia[2] | 10 (24) | 7 (17) |
| Anemia | 9 (22) | 7 (17) |
| Leukocytosis | 9 (22) | 6 (15) |
| Leukpenia | 7 (17) | 5 (12) |

[1]Includes preferred term of platelet count decreased
[2]Includes preferred term of neutrophil count decreased Adverse Events (AE) of Interest and Deaths AEs were assessed per National Cancer Institute's Common Terminology Criteria for Adverse Events (NCI CTCAE), version 4.03.

No DLTs were observed in dose escalation.

Compound 1 as Single Agent 4 (13%) patients receiving Compound 1 as a single agent exhibited IDH-DS; all resolved with treatment interruption, dexamethasone, hydroxyurea and supportive care and then resumed treatment with Compound 1.

The QTcF maximum change from baseline for patients treated with Compound 1 as a single agent is reported in Table 12.

TABLE 12

| | | Maximum Post-Baseline Value | | | |
|---|---|---|---|---|---|
| Treatment Group | Baseline Value | ≤480 msec n (%) | >480-≤500 msec n (%) | >500 msec n (%) | >60 msec Δ from BL n (%) |
| Total Compound 1 SA (N = 30) | ≤480 msec | 27 (90) | 0 | 0 | 1 (3.3)‡ |
| | >480-≤500 msec | 0 | 1 (3.3)† | 0 | 0 |
| | >500 msec | 0 | 0 | 1 (3.3) | 0 |
| | Total | 27 (90) | 1 (3.3) | 1 (3.3) | 1 (3.3) |

2 patients with BBB († in Table 12) enrolled with QTc readings above normal at baseline remained stable within the same QTc range on treatment. One patient (‡ in Table 12) had an increase of >60 msec but remained within the normal limits (<450 msec).

9 patients receiving Compound 1 as a single agent died within 30 days of last dose due to AEs unrelated to treatment with Compound 1. The AEs unrelated to treatment with Compound 1 which resulted in death are summarized below:

Progressive Disease (PD) (n=3)

Central Nervous System (CNS) Events (n=2)

Sepsis (n=1)

Cardiac Arrest (n=1)

Multiorgan failure (n=1)

toxicity to HSCT regime (n=1)

Compound 1 in Combination with Azacitidine

The QTcF maximum change from baseline (BL) for patients treated with Compound 1 and azacitidine in combination is reported in Table 13.

TABLE 13

| Treatment Group | Baseline Value | Maximum Post-Baseline Value | | | |
|---|---|---|---|---|---|
| | | ≤480 msec n (%) | >480-≤500 msec n (%) | >500 msec n (%) | >60 msec Δ from BL n (%) |
| Total Compound 1 + AZA 75 mg/m² | ≤480 msec | 37 (90.0) | 2 (5) | 2 (5) | 4 (10) |
| | >480-≤500 msec | 0 | 0 | 0 | 0 |
| | >500 msec | 0 | 0 | 0 | 0 |
| (N = 41) | Total | 37 (90.0) | 2 (5) | 2 (5) | 4 (10) |

Referring to Table 13, 4 patients with >60 msec which increased from BL included the 2 patients with suspect concomitant medications, 1 patient developed G1 prolongation and 1 patient remained within normal limits. Among the patients with QTcF<480 msec at BL, 2 had values of 480-500 msec, and 2 had values>500 msec. 1 of each group (including 1 with pacemaker) had prolonged QTcF before treatment start. The other 2 had transient prolongation that normalized once suspect concomitant medications discontinued 2 AEs of QTcF prolongation reported on study (G2 and G3). These were transient and patients resumed treatment once suspect concomitant medications discontinued.

7 patients receiving Compound 1 and azacitidine died within 30 days of last dose due to AEs unrelated to treatment with Compound 1. The AEs unrelated to treatment with Compound 1 which resulted in death are summarized below:
Progressive Disease (PD) (n=3)
Central Nervous System (CNS) Events (n=2)
Pneumonia (n=1)
Gastrointestinal fistula (n=1)

The present disclosure includes, among other things, the novel understanding that administration of 300 mg of Compound 1 (e.g., 150 mg BID or 300 mg QD) to a patient or population of patients results in a sustained therapeutically effective trough blood plasma concentration ($C_{ss}$). Such a $C_{ss}$ of Compound 1 resulted in a durable reduction in 2-HG plasma level over the course of at least 6 treatment cycles.

As outlined in this Example, the concentration total plasma concentration of Compound 1 and the plasma concentration of 2-HG was measured in the blood of patients receiving one of three different dose and dose intervals: 150 mg QD, 300 mg QD or 150 mg BID (either receiving Compound 1 as a single agent or in combination with azacitidine as described in the clinical trial of this Example, in each category). The 2-HG levels were measured prior to administration of Compound 1, and then measured after administration of Compound 1 up to cycle 2, day 1 after first receiving Compound 1 (as the solid form obtained from Example 1).

Figure 13:
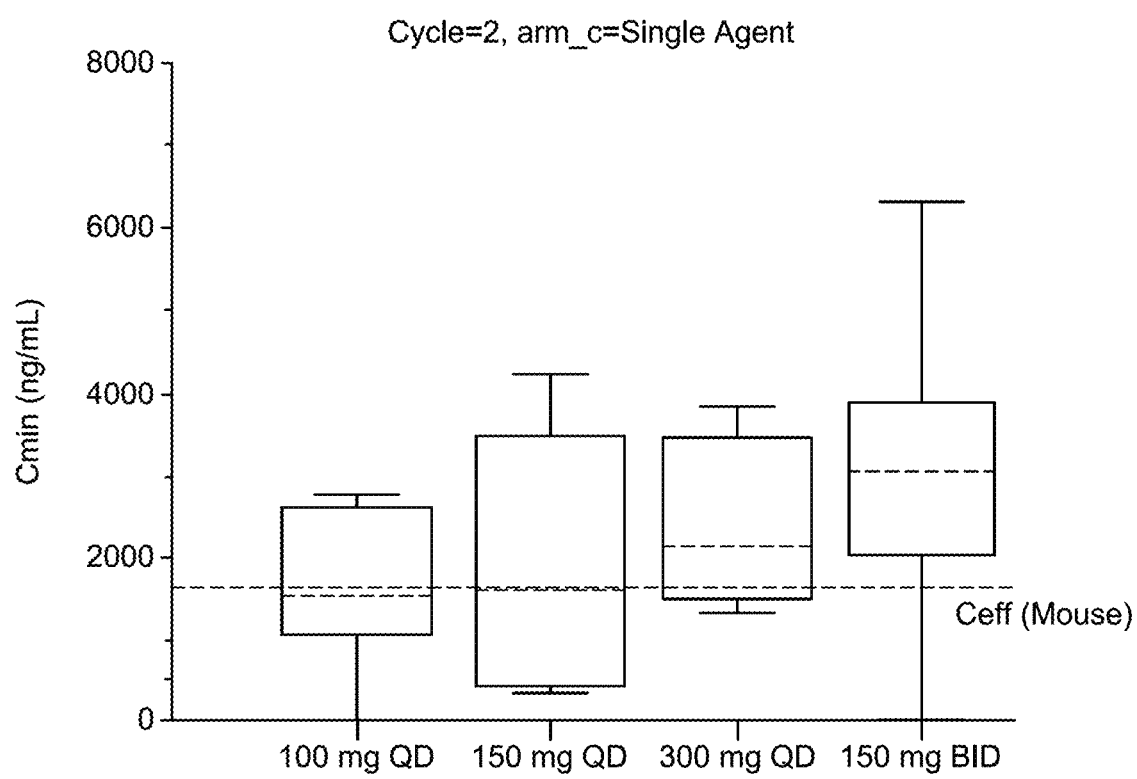
FIG. 13 is a graph of the minimum blood plasma concentration (Cmin) of Compound 1 measured in groups of human patients receiving Compound 1 as a single agent at different dose amounts and dose intervals: day 15 trough (ng/mL) of Compound 1 after administration to patients of 100 QD, 150 mg QD, 300 mg QD, and 150 mg BID Compound 1 as a single agent.
Figure 17:
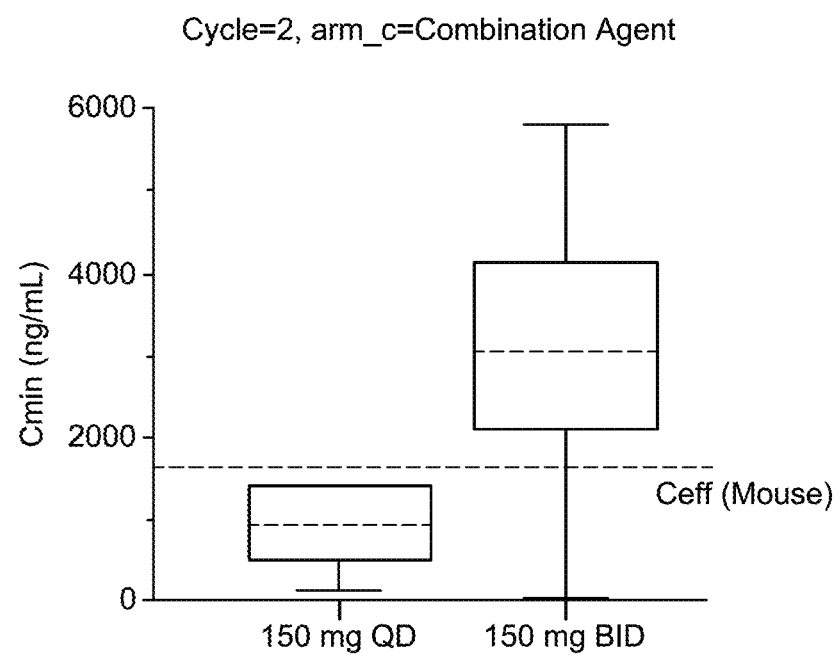
FIG. 17 is a graph of the minimum blood plasma concentration (Cmin) of Compound 1 measured in groups of human patients receiving Compound 1 at different dose amounts and dose intervals, in combination with azacitidine: day 15 trough (ng/mL) of Compound 1 after administration to patients of 150 mg QD and 150 mg BID of Compound 1 in combination with azacitidine.

As shown in FIG. 13 and FIG. 17, the administration of Compound 1 at 150 mg BID resulted in a trough blood plasma concentration above 1,652 ng/mL after cycle 2 of a 28-day treatment cycle as both a single agent and in combination with azacitidine.

As shown in FIG. 2A-2E, the plasma exposures (steady state blood plasma concentration) of Compound 1 were durable (i.e., sustained) throughout at least a 6 cycle treatment duration.

Example 7

Pharmaceutical Product Comprising Olutasidenib

This Example describes a pharmaceutical product comprising olutasidenib (i.e., Compound 1) as the only active moiety and various inactive components (e.g., excipients) ("PRODUCT") that is useful for the treatment of certain forms of cancer.

Olutasidenib (i.e., Compound 1) has a molecular formula of $C_{18}H_{15}ClN_4O_2$, a molecular weight of 354.8, and the following structure:

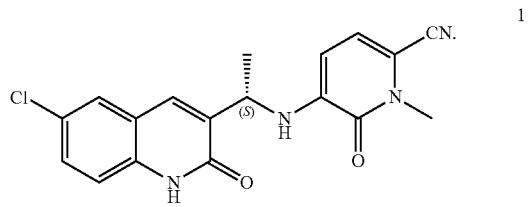

Olutasidenib can also be identified by the following chemical names:
2-Pyridinecarbonitrile, 5-[[(1S)-1-(6-chloro-1,2-dihydro-2-oxo-3-quinolinyl)ethyl]amino]-1,6-dihydro-1-methyl-6-oxo-;
5-{[(1S)-1-(6-chloro-2-oxo-1,2-dihydroquinolin-3-yl)ethyl]amino}-1-methyl-6-oxo-1,6-dihydropyridine-2-carbonitrile; and
(S)-5-((1-(6-chloro-2-oxo-1,2-dihydroquinolin-3-yl)ethyl)amino)-1-methyl-6-oxo-1,6-dihydropyridine-2-carbonitrile.

Olutasidenib also has the following identifiers:
Code designation: FT-2102
CAS Registry Number: 1887014-12-1
UNII: 0T4IMT8S5Z
WHO Number: 11036

An oral unit dosage form comprising a pharmaceutically acceptable solid form of olutasidenib (e.g., as obtained from Step 7 in Example 1) can be formulated as a drug product with various inactive components as excipients (e.g., as a tablet or capsule) (in this Example, referred to as the "PRODUCT"). Each drug product excipient in PRODUCT meets the requirements of the respective current United States Pharmacopeia (USP) or National Formulary (NF) monograph. The capsule shells can comprise gelatin and about 2.9% w/w of titanium dioxide (E171). Preferably, each oral unit dosage form comprises a total of 50 mg or 150 mg of the pharmaceutically acceptable form of olutasidenib (e.g., micronized crystalline olutasidenib) combined (e.g., at 30-50% w/w) as the only active moiety with pharmaceutically acceptable excipients such as a filler (e.g., AVICEL PH101 @50 micron, AVICEL PH102 @100 micron), a disintegrant (e.g., Ac-Di-Sol), optionally one or more compounds as a lubricant (e.g., magnesium stearate), a glidant/anti-adherent, and/or anti-static (e.g., colloidal silicon dioxide). The excipients can form about 50-70% by weight of the pharmaceutical oral unit dosage form. In one example, a capsule or tablet comprises a total of about 33% of olutasidenib, with the remaining weight of the capsule or tablet is formed from excipients and/or capsule material (e.g., a gelatin). Alternatively, the PRODUCT can be provide as tablet for oral administration. Each tablet can contain the following inactive ingredients: colloidal silicon dioxide, croscarmellose sodium, hypromellose acetate succinate, magnesium stearate, microcrystalline cellulose, and sodium lauryl sulfate. The tablet coating can include FD&C blue #2, hypromellose, lactose monohydrate, titanium dioxide, and/or triacetin.

In one example, PRODUCT is indicated for the treatment of adult patients with relapsed or refractory acute myeloid leukemia (AML) with a susceptible isocitrate dehydrogenase-1 (IDH1) mutation as detected by an FDA-approved test. The PRODUCT is indicated for the treatment of adult patients with relapsed or refractory acute myeloid leukemia (AML) with a susceptible isocitrate dehydrogenase-1 (IDH1) mutation as detected by an FDA-approved test. The PRODUCT is administered in a total of about 300 mg of Compound 1 per day to the patient, preferably 150 mg of olutasidenib twice per day. When appropriate, the dose of the PRODUCT (i.e., amount of olutasidenib) can be decreased to 150 mg once per day or 100 mg twice per day.

Optionally, patients are selected for the treatment of AML with PRODUCT based on the presence of IDH1 mutations in the blood or bone marrow. Patients without IDH1 mutations at diagnosis should be retested at relapse because a mutation in IDH1 may emerge during treatment and at relapse. Information on FDA-approved tests for the detection of IDH1 mutations in AML is available at www.fda.gov/CompanionDiagnostics.

The recommended dose of PRODUCT is 150 mg taken orally twice daily until disease progression or unacceptable toxicity, although dose reductions to 100 mg taken orally twice daily or 150 mg taken orally once daily can also be appropriate for some patients. For patients without disease progression or unacceptable toxicity, treat for a minimum of 6 months to allow time for clinical response.

Example 8

Pharmaceutical Product and Companion Diagnostic for Identifying and Treating AML Patients Having an IDH1 Mutation AML is a rapidly progressing cancer that forms in the bone marrow and results in an increased number of abnormal white blood cells in the bloodstream and bone marrow. The National Cancer Institute at the National Institutes of Health estimates that approximately 19,520 people will be diagnosed with AML this year; approximately 10,670 patients with AML will die of the disease in 2018.

Example 7 describes a pharmaceutical product comprising Compound 1 as the only active moiety and various inactive components (e.g., excipients) that is useful for the treatment of certain forms of cancer ("PRODUCT", e.g., the PRODUCT described in Example 7). PRODUCT comprises an isocitrate dehydrogenase-1 inhibitor (Compound 1) that can decrease abnormal production of the oncometabolite 2-hydroxyglutarate (2-HG), leading to differentiation of malignant cells. If an IDH1 mutation is detected in blood or bone marrow samples using an FDA-approved test, a patient may be eligible for treatment with PRODUCT. One example of such a FDA-approved test is the IDH1 Assay of this Example, a companion diagnostic that can be used to detect this mutation. The IDH1 Assay of this Example is an in vitro polymerase chain reaction (PCR) assay for the qualitative detection of single nucleotide variants (SNVs) coding five IDH1 R132 mutations (R132C, R132H, R132G, R132S, and R132L) in DNA extracted from human blood (EDTA) or bone marrow (EDTA). The IDH1 Assay of this Example is for use with a real-time PCR system.

The IDH1 Assay of this Example is indicated as an aid in identifying acute myeloid leukemia (AML) patients with an isocitrate dehydrogenase-1 (IDH1) mutation for treatment with PRODUCT (Compound 1). This test is for prescription use only.

The IDH1 Assay of this Example detects single nucleotide variants (SNVs) coding five IDH1 mutations (R132C, R132H, R132G, R132S, and R132L) by using PCR technology with homogeneous real-time fluorescence detection. The assay uses human blood or bone marrow aspirate specimens and reports a qualitative result. Table 14 lists the IDH1 mutations detected by the IDH1 Assay of this Example.

TABLE 14

Mutations Detected by the IDH1 Assay of this Example

| Codon | IDH1 Mutation | SNV |
|---|---|---|
| R132 | R132C | TGT |
|  | R132H | CAT |
|  | R132G | GGT |
|  | R132S | AGT |
|  | R132L | CTT |

The IDH1 Assay of this Example is a FDA-approved IDH1 companion diagnostic sold under the trade name Abbott RealTime IDH1 (PMA Applicant: Abbott Molecular Inc., 1300 E. Touhy Avenue, Des Plaines, Ill. 60018; FDA Approval Date: Jul. 20, 2018). It will be appreciated that further details on using IDH1 Assay of this Example are available in product literature and instruction manuals accompanying the assay and/or the real-time PCR system.

Biological Principles of the Procedure

The IDH1 Assay of this Example consists of two kits:
IDH1 amplification reagent kit
IDH1 control kit Specimens for the IDH1 Assay of this Example are processed manually using reagents (e.g., lysis buffer containing guanidine isothiocyanate, magnetic microparticles, wash buffers, and/or elution buffer) to isolate and purify sample DNA. The amplification reagents are combined into two amplification master mixes. The purified DNA sample is combined with the master mixes in a 96-well optical reaction plate, and the plate is transferred to a real-time PCR instrument for amplification and detection of IDH1 mutations. The specimen result is automatically reported on a real-time PCR workstation at run completion. Assay controls are included within each run and are processed through DNA extraction, amplification, and detection steps of the assay to assess run validity.

Software parameters specific to the IDH1 Assay of this Example are contained in an assay application specification file, which is loaded onto a real-time PCR instrument by using a CD-ROM disk.

DNA Extraction

The purpose of DNA extraction is to isolate and purify genomic DNA from EDTA preserved blood or bone marrow aspirate specimens to make it accessible for amplification and to remove potential inhibitors of amplification. This process is accomplished by using magnetic particle technology to isolate and purify DNA. During the DNA extraction procedure, cells are lysed at an elevated temperature in a lysis buffer containing guanidine isothiocyanate. DNA is captured on magnetic microparticles, and inhibitors are removed by performing a series of washes with wash buffers. The bound DNA is eluted from the microparticles with elution buffer and is ready for PCR amplification.

Reagent Preparation and Reaction Plate Assembly

IDH1 oligonucleotide reagents (Oligonucleotide Reagent 1 and Oligonucleotide Reagent 2) are each manually combined with a DNA polymerase and activation reagent to create 2 unique master mixes. These master mixes are added to 2 separate wells of a 96-well optical reaction plate along with aliquots of the extracted DNA sample. After manual application of an optical adhesive cover, the plate is transferred to a real-time PCR instrument.

Amplification/Detection

Each master mix is designed to amplify and detect 2 or 3 IDH1 amino acid mutations (codon with mutant nucleotide underlined). Oligonucleotide 1 master mix amplifies and detects R132C (TGT) and R132H (CAT). Oligonucleotide 2 master mix amplifies and detects R132G (GGT), R132S (AGT), and R132L (CTT). Refer to Table 15, In addition, both master mixes are designed to amplify and detect a region of the IDH1 gene outside of codon 132, which serves as an endogenous internal control (IC).

TABLE 15

IDH Mutation Detected by Each Master Mix

| Master Mix | IDH1 Mutation | SNV |
|---|---|---|
| Oligonucleotide 1 | R132C | TGT |
|  | R132H | CAT |
| Oligonucleotide 2 | R132G | GGT |
|  | R132S | AGT |
|  | R132L | CTT |

During the amplification reaction on a real-time PCR instrument, the target DNA is amplified by DNA polymerase in the presence of primers, deoxyribonucleoside triphosphates (dNTPs), and magnesium chloride ($MgCl_2$). The DNA polymerase used in the assay is a thermophilic enzyme that has been chemically modified, rendering it inactive (e.g., inactive at ambient temperature).

During the amplification reaction of the IDH1 Assay of this Example, DNA polymerase is first activated at a high temperature. During each subsequent round of thermal cycling, a high temperature is used to melt double-stranded DNA strands, followed by a low temperature where primers anneal to their respective targets and are extended to generate double-stranded DNA products. Exponential amplification of the products is achieved through repeated cycling between high and low temperatures. Amplification of IDH1 mutation and IC targets takes place simultaneously in the same PCR well.

IDH1 products are detected during the annealing/extension step by measuring the real-time fluorescence signals of the IDH1 mutation and IC-specific probes, respectively. The IDH1 mutation and IC-specific probes are labeled with different fluorophores, allowing their signals to be distinguishable in a single PCR well.

Assay Protocol

The IDH1 Assay protocol includes the following steps:
A. Manual preparation (i.e., DNA extraction) of samples (specimens and controls).
B. PCR assay setup using the sample eluates and an IDH1 amplification reagent kit.
C. Amplification/detection on a real-time PCR instrument.

Assay Results

For each patient sample, 2 PCR reactions are evaluated. The IDH1 Assay of this Example is a qualitative assay for which specimen interpretations are reported as "Mutation Detected" or "Not Detected." For specimens with interpretations of "Mutation Detected", the identity of the IDH1 mutation detected is reported.

Prevention of Nucleic Acid Contamination

The possibility of nucleic acid contamination is minimized because:
  IDH1 Assay of this Example performs amplification and fluorescence detection in a sealed 96-well optical reaction plate.
  Detection is carried out automatically without the need to open the 96-well optical reaction plate.
  Aerosol barrier pipette tips are used for all pipetting. The pipette tips are discarded after use.
  Separate dedicated areas are used to perform IDH1 Assay of this Example.

We claim:

1. A method of treating acute myeloid leukemia (AML) in patients with an isocitrate dehydrogenase-1 (IDH1) mutation, the method comprising steps of:
  a. isolating and purifying DNA from a sample obtained from a patient;
  b. detecting an IDH1 mutation in the DNA from the sample; and
  c. administering to the patient with the IDH1 mutation 150 mg of olutasidenib twice daily in a pharmaceutically acceptable composition.

2. The method of claim 1, wherein the IDH1 mutation is an IDH1 R132 mutation.

3. The method of claim 2, wherein the IDH1 R132 mutation is selected from the group consisting of R132C, R132H, R132S, R132G, and R132L.

4. The method of claim 1, wherein the detecting an IDH1 mutation comprises detecting a single nucleotide variant (SNV) coding the IDH1 mutation, wherein the IDH1 mutation is selected from the group consisting of R132C, R132H, R132G, R132S, and R132L.

5. The method of claim 4, wherein the IDH1 mutation is detected using polymerase chain reaction (PCR) technology with homogeneous real-time fluorescence detection.

6. The method of claim 1, wherein the detecting an IDH1 mutation comprises using an in vitro PCR assay for the qualitative detection of single nucleotide variants (SNVs) coding an IDH1 R132 mutation selected from the group consisting of R132C, R132H, R132G, R132S, and R132L in the DNA from the sample.

7. The method of claim 1, wherein the sample is obtained from patient bone marrow.

8. The method of claim 1, wherein the sample is obtained from patient blood.

9. The method of claim 1, wherein the pharmaceutically acceptable composition is formulated for oral administration.

10. The method of claim 9, wherein the pharmaceutically acceptable composition is a capsule.

11. The method of claim 5, wherein the method further comprises combining the extracted DNA sample with oligonucleotide primers designed to specifically amplify (i) R132C and R132H mutations or (ii) R132G, R132S, and R132L mutations.

12. The method of claim 11, wherein the real-time fluorescence signal of each IDH1 mutation of either (i) R132C and R132H or (ii) R132G, R132S, and R132L is distinguishable in a single well.

13. A method of treating acute myeloid leukemia (AML) in patients with an isocitrate dehydrogenase-1 (IDH1) mutation, the method comprising administering twice daily to a patient with an IDH1 mutation 150 mg of olutasidenib in a pharmaceutically acceptable composition, wherein the IDH1 mutation has been detected using an FDA-approved diagnostic test.

14. The method of claim 13, wherein the FDA-approved diagnostic test comprises detecting an IDH1 mutation in DNA from a sample obtained from the patient.

15. The method of claim 13, wherein the patient is receiving or has received therapy comprising azacitidine or cytarabine.

16. The method of claim 13, wherein the AML, is relapsed or refractory.

17. A method of treating AML in patients with an isocitrate dehydrogenase-1 (IDH1) mutation, the method comprising steps of:
 determining whether the patient has an IDH1 mutation by:
  i. obtaining a sample from the patient; and
  ii. performing an assay on the sample to determine if the patient has an IDH1 mutation; and
 if the patient has an IDH1 mutation, then administering to the patient with the IDH1 mutation 150 mg of olutasidenib twice daily in a pharmaceutically acceptable composition, and
 if the patient does not have an IDH1 mutation, then not administering to the patient with the IDH1 mutation 150 mg of olutasidenib twice daily in a pharmaceutically acceptable composition.

18. The method of claim 17, wherein the IDH1 mutation is an IDH1 R132 mutation.

19. The method of claim 18, wherein the IDH1 R132 mutation is selected from the group consisting of R132C, R132H, R132S, R132G, and R132L.

20. The method of claim 17, wherein the assay comprises detecting an IDH1 mutation in DNA from a sample obtained from the patient.

21. A method of treating an adult patient with acute myeloid leukemia (AML) with a susceptible IDH1 mutation as detected by an FDA-approved test, the method comprising administering to the patient in need thereof 150 mg of olutasidenib twice daily in a pharmaceutically acceptable composition.

22. The method of claim 21, wherein the AML is relapsed or refractory acute myeloid leukemia.

23. The method of claim 22, further comprising selecting the patient for the treatment of AML prior to the administration of olutasidenib based on the presence of an IDH1 mutation in the blood or bone marrow.

24. The method of claim 22, wherein the patient is identified as harboring an IDH1 mutation selected from the group consisting of R132C, R132H, R132S, R132G, and R132L.

* * * * *